(12) United States Patent
Fakhoury et al.

(10) Patent No.: US 8,383,887 B2
(45) Date of Patent: Feb. 26, 2013

(54) METHODS OF USING PLANTS CONTAINING THE GDHA GENE

(75) Inventors: Ahmad M. Fakhoury, Carbondale, IL (US); David A. Lightfoot, Carbondale, IL (US)

(73) Assignee: Southern Illinois University Carbondale, Carbondale, IL (US)

( * ) Notice: Subject to any disclaimer, the term of this patent is extended or adjusted under 35 U.S.C. 154(b) by 303 days.

(21) Appl. No.: 12/708,174

(22) Filed: Feb. 18, 2010

(65) Prior Publication Data

US 2010/0223693 A1    Sep. 2, 2010

Related U.S. Application Data

(60) Provisional application No. 61/153,576, filed on Feb. 18, 2009.

(51) Int. Cl.
| | |
|---|---|
| C12N 15/09 | (2006.01) |
| C12N 15/82 | (2006.01) |
| C12N 15/31 | (2006.01) |
| A01H 5/00 | (2006.01) |

(52) U.S. Cl. ........ 800/279; 800/278; 800/298; 800/320; 800/288; 800/301; 435/69.1

(58) Field of Classification Search .................. None
See application file for complete search history.

(56) References Cited

U.S. PATENT DOCUMENTS

| | | | |
|---|---|---|---|
| 5,177,010 A | 1/1993 | Goldman et al. | |
| 5,302,523 A | 4/1994 | Coffee et al. | |
| 5,464,765 A | 11/1995 | Coffee et al. | |
| 5,484,956 A | 1/1996 | Lundquist et al. | |
| 5,489,520 A | 2/1996 | Adams et al. | |
| 5,998,700 A | 12/1999 | Lightfoot et al. | |
| 6,329,573 B1 | 12/2001 | Lightfoot et al. | |

OTHER PUBLICATIONS

Zummo, N. et al, Interaction of *Fusarium moniliforme* and *Aspergillus flavus* on Kernel Infection and Aflatoxin Contamination in Maize Ears, Plant Disease, 1992, pp. 771-773, vol. 76.
An, G. et al, New cloning vehicles for transformation of higher plants, The EMBO Journal, 1985, pp. 277-284, vol. 4, No. 2.
Giedt, C.D. et al, The maize LAG1-0 mutant suggests that reproductive cell lineages show unique gene expression patterns early in vegetative development, The Plant Journal, 2000, pp. 815-823, vol. 24, No. 6.
Ishida, Y. et al, High efficiency transformation of maize (*Zea mays* L.) mediated by *Agrobacterium tumefaciens*, Nature Biotechnology, 1996, pp. 745-750, vol. 14.
Schmittgen, T.D. and Livak, K.J., Analyzing real-time PCR data by the comparative CT method, Nature Protocols, 2008, pp. 1101-1108, vol. 3, No. 6.
Lutcke, H.A. et al, Selection of AUG initiation codons differs in plants and animals, The EMBO Journal, 1987, pp. 43-48, vol. 6, No. 1.
Pfaffl, M.W., A new mathematical model for relative quantification in real-time RT-PCR, Nucleic Acids Research, 2001, pp. 2002-2007, vol. 29, No. 9.
Tsitsigiannis, D.I. et al, *Aspergillus* Infection Inhibits the Expression of Peanut 13S-HPODE-Forming Seed Lipoxygenases, MPMI, 2005, pp. 1081-1089, vol. 18, No. 10.
Wootton, J.C., Reassessment of ammonium-ion affinities of NADP-specific glutamate dehydrogenases, Biochem. j., 1983, pp. 527-530, vol. 205.
Cock, J.M., et al, A nuclear gene with many introns encoding ammonium-inducible chloroplastic NADP-specific glutamate dehydrogenase(s) in *Chlorella sorokiniana*, Plant Nol. Biol., 1991, pp. 1023-1044, vol. 17.
Miller, P.W., et al, Alternative splicing of a precursor-mRNA encoded by the *Chlorella sorokiniana* NADP-specific glutamate dehydrogenase gene yields mRNA for precursor proteins of isozyme subunits with different ammonium affinities, Plant Mol. Biol., 1998, pp. 243-263, vol. 37.
Andersson, J.O., et al., "Evolution of glutamate dehydrogenase genes: evidence for lateral gene transfer within and between prokaryotes and eukaryotes" BMC Evolutionary Biology 3:14-24 (2003).
Asakura, Y., et al., "Altered Metabolic Flux due to Deletion of odhA causes L-Glutamate Overproduction in *Corynebacterium glutamicum*" Applied and Environmental Microbiology 73(4):1308-1319, (2007).
Benachenhou-Lahfa, N., et al., "Evolution of Glutamate Dehydrogenase Genes: Evidence for Two Paralogous Protein Families and Unusual Branching Patterns of the Archaebacteria in the Universal Tree of Life" J. Mol. Evol. 36:335-346 (1993).
Hashim, S., et al., "The Arginine Regulatory Protein Mediates Repression by Arginine of the Operons Encoding Glutamate Synthetase and Anabolic Glutamate Dehydrogenase in *Pseudomonas aeruginosa*" J. Bacteriol. 186 (12):3848-3854 (2004).
Monaco, C., et al., "Indentification of Meningococcal L-Glutamate ABC Transporter Operon Essential for Growth in Low-Sodium Environments" Infection and Immunity 74(3):1725-1740 (2006).
Rosario, C.J., et al., "Importance of Tetramer Formation by the Nitrogen Assimilation Control Protein for Strong Repression of Glutamate Dehydrogenase Formation in *Klebsiella pneumoniae*" J. Bacteriol. 187(24):8291-8299 (2005).
Saum, S.H., et al., "Biochemical and Molecular Characterization of the Biosynthesis of Glutamine and Glutamate, Two Major Compatible Solutes in the Moderately Halophilic Bacterium *Halobacillus halophilus*" J. Bacteriol. 188 (19):6808-6815 (2006).
Syn, C.K.C., et al., "Characterization of *Pseudomonas putida* genes responsive to nutrient limitation" Microbiology 50:1661-1669 (2004).
Tanous, C., et al., "Glutamate Dehydrogenase Activity Can be Transmitted Naturally to *Lactococcus lactis* Strains to Stimulate Amino Acid Conversion to Aroma Compounds" Applied and Environmental Micorbiology 72(2):1402-1409, (2006).

(Continued)

*Primary Examiner* — Medina A Ibrahim
(74) *Attorney, Agent, or Firm* — Polsinelli Shughart PC

(57) ABSTRACT

Disclosed are new effects of increased gdhA gene expression on plants that are susceptible to *Aspergillus* and *Fusarium virguliforme* infection. Plants transformed with the gdhA gene are resistant to aflatoxin accumulation following *Aspergillus* infection, and to root rot following *F. virguliforme* infection. The resistance to aflatoxin accumulation and root rot in gdhA$^+$ plants is coincident with drought tolerance and resistance of the plants to certain herbicides. Methods for controlling aflatoxin contamination and root rot in crop plants, and for screening plants putatively transformed with gdhA, are described.

55 Claims, 21 Drawing Sheets

OTHER PUBLICATIONS

Ticehurst, J.R., et al., "Effective Detection of Toxigenic *Clostridum difficile* by a Two-Step Algorithm Including Tests for Antigen and Cytotoxin" J. Clin. Micro. 44(3):1145-1149 (2006).

Wemekamp-Kamphuis, H.H., et al., "Identification of Sigma Factor σB-Controlled Genes Their Impact on Acid Stress, High Hydrostatic Pressure, and Freeze Survival in *Listeria monocytogenes* EGD-e" Applied and Environmental Microbiology 70(6):3457-3466, (2004).

Williams, A.G., et al., "Glutamate dehydrogenase activity in *Lactobacilli* and the use of glutamate dehydrogenase-producing adjunct *Lctobacillus* spp. Cultures in the manufacture of cheddar cheese" J. Applied Micro. 101:1062-1075 (2006).

E.coli gdhA

TCGAAACTGAAAAGCACATAAACAACATGACATAAGCACAATCGTATTAATATATAAGGGTTTTATA

TCTATGGATCAGACATATTCTCTGGAGTCATTCCTCCTCAACCATGTCCAAAAG

CGGGACCCGAATCAAACCGAGTTGCGCCAAGCCGTTCGTGAAGTAATGACCACACTCTGGCCTTTCTT

GAACAAAATCCAAATATGCCAGATGTCATTACTGGAGCGGTCTCGGTTGAA

CCGGAGCGGGTGATCCAGTTTCGCGTGGTTATGGGTGATGATCGCAACCAGATACAGGTCAACCGTGCAT

GGCGTGTGCAGTTCAGCTCTGCGCCCATGGCCCGTACAAAGGCGGTATGCGC

TTCCATCGTCAGTTAACCTTTCCATTCTCAAATTCCTGGCTTTGAACAAACTTCAAAAATGCCCTGA

CTACTCTGCCGATGGGCGGTGTAAGGCGGCAGCGATTTCGATCCGAAA

GGAAAAAGGCGAGGTGAAGTAGTGATGGGTTTTGCCAGGCGTGATGACTGAACTGTATGCCACTGGGCG

CGGATACCGAGTTCCGGGCAGGTGATATCGGGGTTGGTTCGTTGAAGTC

*Fig. 1A*

GGCTTTATGGCGGGATGATGAAAAGCTCTCCAACAATACCCCTGGTCTTCACCGGTAAGGCCTTT

CATTTGGCGGGAGTCTTATTCGCCCGGAAGCTACCGGCTACCGGTCTGGTT

TATTTCACAGAAGCAATGCTAAAACGCCACGGTATGGGTTTTGAAGGGATGCGCGTTTCGTTTCTGGCT

CCGGCAACGTCGCCCAGTACGCTATCGAAAAAGCGATGGAATTTGGTGCT

CGTGTGATCACTGGTCAGACTCCAGCGCCACTGTAGTTGATGAAAGCCGATTCAGCGAAAGAGAAACTGGC

AGGTCTTATCGAAATCAAAGCCATGGTCGACTGGCAGATTAC

GCCAAAGAATTGGTCTGTCTATCTCGAAGCCAACAGCCGTGGTCTACCGGTTGATATCGCCCTGCCT

TGGCGCCACCCAGAATGAACTGGATGTTGACGCGGCCATCAGCTTATC

GCTAAATGGCGGTTAAAGCCGTCGCCGAAGGGCAAATATGCCGACCACCATGAAGGACTGAACTGTTCCAG

CAGGCAGGCGTACTATTTGCACCGGGTAAAGCGGCTAATGCTGGTGGC

Fig. 1B

GTCGCTACATCGGGCCTGAAATGGCACAAAAACGCTGCGGCTGGGCTGGAAAGCCGAGAAAGTTGACCGCA

CGTTTGCATCACATCATGCTGGATATCCACCATGCCCTGTGTTGACCAT

GGTGGGTGAAGGTGAGCAAACCAACTAGTGCAGGGCGGAACATTGCCGGTTTGTGAAGGTTGCCGATGCG

ATGCTGGCGCAGGGGTGTGATTTAAGTTGTAAATGCCTGATGGCGCTAC

GCTTATCAGGCCTACAAATGGCACAATTCATTGCAGTTACGCTCTAATGTAGGCCAAGCGCAAGCGCAGCGCC

CCCGGCAAAATTTCAGGGGTTTATGAGTATTTAACGGATGATGCTCCC

CACGGAACATTTCTTACTGGCCAATTCTTACTGTAGTGCTCCCAAAACTGCTTGTCGTAACGATAA

CACGCTTCAAGTTCAGCATCCGTTAAC

Fig. 1C

Forward primer at 5'

<u>XbaI</u>   <u>Kozak</u>
5'-...G GGT TCT AGA ACA ATG GAT CAG ACA TAT TCT CTG GAG...3'
                         start
                         codon 5'-...G GGT TTT ATA TCT ATG GAT CAG ACA TAT TCT CTG GAG TCA TTC CTC AAC-gdhA
3'-...C CCA AAA TAT AGA TAC CTA GTC TGT ATA AGA GAC CAC AGT AAG GAG TTC-gene
        .........  M   D   Q   T   Y   S   L   E   S   F   L   N

Fig. 2A

Reverse primer at 3' stop       mRNA
                                    codon    destabilizer
gdhA--T GCG ATG CTG GCG CAG GGT GAG ATT TAA GTT GTA AAT G...-3'
gene--C CGC TAC GAC CGC GTC CCA CTC TAA ATT CAA CAT TTA C...-5'
........A   M   L   A   Q   G   V   I 3'...C TAC GAC CGC GTC CCA CAC TAA ATT <u>CTC GAG</u> TTA C...5'
                                         SacI

```
METAspGlnThrTyrSerLeuGluSerPheLeuAsnHisValGlnLysArgAspProAsn
GlnThrGluPheAlaGlnAlaAlaValArgGluValMETThrThrLeuTrpProPheLeuGlu
GlnAsnProLysTyrArgGlnMETSerLeuLeuGluArgLeuValGluProGluArgVal
IleGlnPheArgValValTrpValAspAspArgAsnIleGlnValAsnArgAlaTrp
ArgValGlnPheSerSerAlaIleGlyProTyrLysGlyGlyMETArgPheHisProSer
ValAsnLeuSerIleLeuLysPheLeuGlyPheGluGlnThrPheLysAsnAlaLeuThr
ThrLeuProMETGlyGlyLysGlyLysSerAspPheAspProLysGlyLysSerGlu
GlyGluValMETArgPheCysGlnAlaLeuMETThrGluLeuTyrArgHisLeuGlyAla
AspThrAspValProAlaGlyValGlyAspIleGlyValGlyArgGluValGlyPheMETAla
GlyMETMETLysLysGlyLeuSerAsnAsnThrAlaCysValPheThrGlyLysGlyLeuSer
PheGlyGlySerLeuIleArgProGluAlaThrGlyTyrLeuValTyrPheThrGlu
AlaMETLeuLysArgHisGlyMETGlyPheGluGlyMETArgValSerValSerGlySer
GlyAsnValAlaGlnTyrAlaIleGluLysAlaMETGluPheGlyAlaArgValIleThr
AlaSerAspSerSerGlyThrValValAspGluSerGlyPheThrLysGluLysLeuAla
ArgLeuIleGluIleLysAlaSerArgAspGlyArgValAlaAlaAspTyrAlaLysGluPhe
GlyLeuValTyrLeuGluGlyGlnProTrpSerLeuProValAspIleAlaLeuPro
CysAlaThrGlnAsnGluLeuAspValAspAlaAlaHisGlnLeuIleAlaAsnGlyVal
LysAlaValAlaGlyValAlaAsnMETProThrThrIleGluAlaThrGluLeuPheGln
GlnAlaGlyValLeuPheAlaProGlyLysAlaAsnAlaAlaGlyValAlaThrSer
GlyLeuMETAlaGlnAsnAlaAsnAlaAlaArgLeuGlyTrpLysAlaCysValAspHisGlyGlyGly (?)
ArgLeuHisHisIleMETLeuAspIleHisAlaCysValAspIleHisGlyGlyGlyGly
GluThrAsnTyrValGlnGlyAlaAsnIleAlaGlyPheValLysAspAspAla
METLeuAlaGlnGlyValIle
```

Mutagenized gdhA for Plant expression (tobacco and corn)

1
XbaI Kozak
5'- TCTAGAACAATGGATCAGACATATTCTCTGGAGTCATTCCTCAACCATGTCCAAAAG

CGCGACCCGAATCAAACCGAGTTCGCGCAAGCCGTTCGTGAAGTAATGACCACACTCTGGCCTTTTCTT

GAACAAAATCCAAAATATCGCCAGATGTCATTACTGGAGCGTCTGGTTGAA

CCGGAGCGCGTGATCCAGTTTCGCGTGGTATGGGTTGATGATCGCAACCAGATACAGGTCAACCGTGCAT

GGCGTGTGCAGTTCAGCTCTGCCATCGGCCCGTACAAAGGCGGTATGCGC

TTCCATCCGTCAGTTAACCTTTCCATTCTCAAATTCCTCGGCTTTGAACAAACCTTCAAAAATGCCCTGA

CTACTCTGCCGATGGGCGGTGGTAAAGGCGGCAGCGATTTCGATCCGAAA

GGAAAAAGCGAAGGTGAAGTGATGCGTTTTTGCCAGGCGCTGATGACTGAACTGTATCGCCACCTGGGCG

CGGATACCGACGTTCCGGCAGGTGATATCGGGGTTGGTGGTCGTGAAGTC

Fig. 6AI

```
GGCTTTATGGCGGGATGATGAAAAGCTCTCCAACAATACCGCCTGGTCTTCACCGGTAAGGCCTTT

CATTTGGGCGGCAGTCTTATTCGCCCGGAAGCTACCGGCTACGGTCTGGTT

TATTTCACAGAAGCAATGCTAAAACGCCACGGTATGGGTTTTGAAGGGATGCGGGTTTCGTTCTGGCT

CGGCAACGTCGCCCAGTAGCTATCGAAAAGCGATGAATTGGTGCT

CGGTGATCACTGGTGTCAGACTCCAGGCGCACTGTAGTTGAAGCGGATTCACGAAAGAGAAACTGGC

ACGTCTTATCGAAATCAAGCCAGCGTCGAGTGGCAGATTAC

GCCAAGAATTGTCTGGTCTATCTGAAGGCCAACAGCCGTGTCTCTACCGGTTGATATCGCCCTGCCT

TCGGCCACCCAGAATGAACTGGATGTTGACGCGGGCATCAGCTTATC

GCTAATGGCGTTAAAGCCGTCGCCGAAGGGCAAATATGCCGACCATCGAAGCGACTGAACTGTTCCAG

CAGGCAGGGTACTATTTGCACCGGGTAAAGCGGTAATGCTGGTGGC

GTCGCTACATCGGGCCTGGAAATGGCCACAAACGCTGCGGCCCTGGAAAGCCGAGAAGTTGACGCA
```

Fig. 6A2

CGTTTGCATCACATCATGCTGGATATCCACCATGCCTGTGTTGACCAT

GGTGGTGAAGGTGAGCAAACCAACTAGTGCAGGGCGCGAACATTGCCGGTTTGTGAAGGTTGCCGATGCG

ATGCTGGCGCAGGGTGTGATTTAAGTTGTAAATGCCTGATGGCGCTAC

GCTTATCAGGCCTACAAATGGGCCACAATTCATTGCAGTTACGCTCTAATGTAGCCGGGCAAGCGCAGCGCC

CCCGGCAAAATTTCAGGCGTTTATGAGTATTTAAGAGCTC
SacI

Fig. 6A3

Mutagenized gdhA for chloroplast targetting (tobacco and corn)

1
SphI
------
gCATgCATCAGACATATTCTCGAGTCATTCCTCAACCATGTCCAAAAG

CGGGACCCGAATCAAACCGAGTTCGCGGCAAGCCGTTCGTGAAGTAATGACCACACTCTCGGCCTTTCTT

GAACAAAATCCAAATATCGCCAGATGTCATTACTGGAGGCTCTGGTTGAA

CCGGAGCGGTCAGTTTCGGATCCAGTTCGCGTGGTATGGGTTCATGATCGCAACCAGATACAGTCAACCGTGCAT

GGCGTGTGCAGTTCAGTCTCGCGCCCTGTAACAAAGCGGGTATGGC

TTCCATCCGTCAGTTAACCTTTCCATTCTCAAATTCCTCGGCTTGAACAACCTTCAAAAATGCCCTGA

CTACTCTGCCGATGGGCGGGTGTAAAGCGGGCAGCGATTCGATCCGAAA

GGAAAAAGCGAAGGTGAAGTGATGCGTTTTTGCCAGGCGTGATGACTGAACTGTATGCCACCTGGGGCG

CGGATACCGACGTTCCGGCAGGTGATATCGGGGTTGGTGTTGTGAAGTC

*Fig. 6B1*

GGCTTTATGGGGGGATGATGAAAAAGCTCTCCAACAATACCGCCCTGCGTCTTCACCGGTAAGGGCCTTT

CATTTGCGGCAGTCTTATTCGCCCGGAAGCTACGGCTACGGTCTGGTT

TATTTCACAGAAGCAATGCTAAAACGCCAAGGGTATGGGTTTGAAGGATGCGGTTTCCGTTTCTGGCT

CCGGCAACGTCGCCCAGTAGCTATCGAAAAGCCATGCGAATTGATGAATTTGGTGCT

CGTGTGATCACTGGTCAGACTCCAGGGGCCACTGTAGTGATCGAAAGGCGATTCACGAAAGAGAAACTGGC

ACGTCTTATCGAAATCAAAGCCAGCCGCGATGGTCGAGTGGCAGATTAC

GCCAAAGATTTGGTGCTGTCTATCTCGAAGGCCAACACCGGTCTCTACGGTGTGATATCGCCCTGCCT

TGCCCCACCCAGAATGAACTGGATGTTGACGCCGGCCATCAGCTTATC

GCTAATGGGGTTAAAGCCGTTCCGCCGAAGGGCAAATATGCCGACCACCATGAAGGACTGAACTGTTCCAG

CAGGCAGGCGTACTATTTGCACGGGGTAAAGCGGCTAATGCTGGTGGC

Fig. 6B2

GTCGGCTACAATCGGGGCCTGAAATGGCACAAAACGTCGGGCCGCCTGGGCTGAAAGCCGAGAAGTTGACGCA

CGTTTGCATCACATCATGCTCGGATATCCACCATGCCCTGTTGACCAT

GGTGGTGAAGGTGAGCAAACCAACTACTGCAGGGCGGGAACATTGCCGGTTTTGTGAAGGTTGCCGATGCG

ATGCTGGGCGAGGGTGATTTAAGTGTAAATGCCTGATGGCGCTAC

GCTTATCAGGCCTACAAATGGCACAATTCATTGCAGTTACGTCTAATGTAGGCCCGGGCAAGCCGCAGCGCC

CCCGGCAAATTTCAGGCGTTTATGAGTATTTAAGAGCTC
                                  SacI

*Fig. 6B3*

Mutagenized gdhA for Plant expression with added linker restriction sites (corn)

PstI SalI XbaI Kozak
ctgcaggtcgactCTAGAACAATGGATCAGACATATTCTCTGAGTCATTCCTCAACCATGTCCAAAAG

CGCGACCCGAATCAAACCGAGTTCGCGCAAGCCGTTCGTGAAGTAATGACCACACTCTGGCCTTTTCTT

GAACAAAATCCAAATATCGCCAGATGTCATTATCGGAGCGTCTGGTTGAA

CCGGAGCGGGTGATCAGTTCGGTGTATGGTTGATGATCGAACCAGATACAGGTCAACCGTGCAT

GGCGTGTGCAGTTCAGCTCGCCATGGCCCGTACAAAGGCGTATGCGC

TTCCATCCGGTAACCTTCAAATTCCCGGCTTGAACAAACCTTCAAAATGCCCTGA

CTACTCTGCCGATGGGCCGGTGTAAAGGCGGGCCAGCCGATTTCGATCCGAAA

GGAAAAGCGAAGTGATGGTTTTTGCCAGCGCTGATGACTGAACTGTATGCCACCTGGGCG

CGGATACCGAGTTCCGGCTGATATCGGGGTTGGTGGTGTGAAGTC

*Fig. 7AI*

GGCTTTATGGCGGGATGATGAAAAGCTCTCCAACAATACCGCTGCGTCTTCACCGGTAAGGGCCTTT

CATTTGGGCGGCAGTCTTATTCGCCCGGAAGCTACCGGCTACGGTCTGGTT

TATTTCACAGAAGCAATGCTAAAACGCCACGGTATGGGTTTGAAGGATGCGGCGTTTCCGTTTCTGGCT

CGGCAACGTCGCCCAGTACGCTATCGAAAAAGCGATGGAATTTGGTGCT

CGTGTGATCACTGGGTCAGACTCCAGGGCCACTGTAGTTGATGAAGGGATTCACGAAAGAGAAACTGGC

ACGTCTTATCGAAATCAAAGCCAGCCGATGGTCGAGTGGCAGATTAC

GCCAAAGAATTGGTCTGTATCTCGAAGGCCAACACCGTGTCTACCGGTGATATCGCCCTGCCT

TGCGCCACCCAGAATGAACTGGATGTTGACGCGGCATCAGCTTATC

GCTAATGGCGTTAAAGCCGTTGCCGAAGGGCAAATATGCCGACCATCGAAGGACTGAACTGTTCCAG

CAGGCAGGGCGTACTATTTGCACCGGGTAAAGCGGCTAATGCTGGTGGC

*Fig. 7A2*

GTCGCTACACATGGGCCTGGAAATGGCACAAAACGTGCCGCCTGGGCTGGAAAGCCCGAGAAAGTTGACGCA

CGTTTGCATCACATCATGCTGGATATCCACCATGCCTGTGTTGACCAT

GGTGGTGAAGGTGAGCAAACCAACTACGTGCAGGGCGGGAACATTGCCGGTTTTGTGAAGGTTGCCGATGCG

ATGCTGGGCGCAGGGTGTGATTTAAGTTGTAAATGCCCTGATGGCGCTAC

GCTTATCAGGCCTACAACATGGGCACAATTCATTGCAGTTACGCTCTAATGTAGGCCGGGCAAGCGCCAGCGCC

CCCGGCAAATTTCAGGCGTTTATGAGTATTTAAGAGCTC
SacI

*Fig. 7A3*

```
EcoRI        SphI
5' aattcgaacccctcgcatg 3'
3'     gcttggggaagc 5'

3' EcoRI SphI adapter - between nosT and plasmid for corn transformation
```

Fig. 8

SEQUENCE LISTING

<160> NUMBER OF SEQ ID NOS: 15

<210> SEQ ID NO 1
<211> LENGTH: 1659
<212> TYPE: DNA
<213> ORGANISM: Escherichia coli

<400> SEQUENCE: 1

```
tcgaaaactg caaaagcaca tgacataaac aacataagca caatcgtatt aatatataag    60
ggttttatat ctatggatca gacatattct ctggagtcat tcctcaacca tgtccaaaag   120
cgcgacccga atcaaaccga gttcgcgcaa gccgttcgtg aagtaatgac cacactctgg   180
ccttttcttg aacaaaatcc aaaatatcgc cagatgtcat tactggagcg tctggttgaa   240
ccggagcgcg tgatccagtt tcgcgtggta tgggttgatg atcgcaacca gatacaggtc   300
aaccgtgcat ggcgtgtgca gttcagctct gccatcggcc cgtacaaagg cggtatgcgc   360
ttccatccgt cagttaacct ttccattctc aaattcctcg gctttgaaca aaccttcaaa   420
aatgccctga ctactctgcc gatgggcggt ggtaaaggcg gcagcgattt cgatccgaaa   480
ggaaaaagcg aaggtgaagt gatgcgtttt tgccaggcgc tgatgactga actgtatcgc   540
cacctgggcg cggataccga cgttccggca ggtgatatcg gggttggtgg tcgtgaagtc   600
ggctttatgg cggggatgat gaaaaagctc tccaacaata ccgcctgcgt cttcaccggt   660
aagggccttt catttggcgg cagtcttatt cgcccggaag ctaccggcta cggtctggtt   720
tatttcacag aagcaatgct aaaacgccac ggtatgggtt ttgaagggat gcgcgtttcc   780
gtttctggct ccggcaacgt cgcccagtac gctatcgaaa aagcgatgga atttggtgct   840
cgtgtgatca ctgcgtcaga ctccagcggc actgtagttg atgaaagcgg attcacgaaa   900
gagaaactgg cacgtcttat cgaaatcaaa gccagccgcg atggtcgagt ggcagattac   960
gccaaagaat ttggtctggt ctatctcgaa ggccaacagc cgtggtctct accggttgat  1020
atcgccctgc cttgcgccac ccagaatgaa ctggatgttg acgccgcgca tcagcttatc  1080
gctaatggcg ttaaagccgt cgccgaaggg gcaaatatgc cgaccaccat cgaagcgact  1140
gaactgttcc agcaggcagg cgtactattt gcacccggta agcggctaa tgctggtggc  1200
gtcgctacat cgggcctgga aatggcacaa aacgctgcgc gcctgggctg gaaagccgag  1260
```

-continued

```
aaagttgacg cacgtttgca tcacatcatg ctggatatcc accatgcctg tgttgaccat    1320
ggtggtgaag gtgagcaaac caactacgtg cagggcgcga acattgccgg ttttgtgaag    1380
gttgccgatg cgatgctggc gcagggtgtg atttaagttg taaatgcctg atggcgctac    1440
gcttatcagg cctacaaatg gcacaattc attgcagtta cgctctaatg taggccgggc     1500
aagcgcagcg cccccggcaa aatttcaggc gtttatgagt atttaacgga tgatgctccc    1560
cacggaacat tcttatggg ccaacggcat tcttactgt agtgctccca aaactgcttg      1620
tcgtaacgat aacacgcttc aagttcagca tccgttaac                           1659

<210> SEQ ID NO 2
<211> LENGTH: 37
<212> TYPE: DNA
<213> ORGANISM: Artificial Sequence
<220> FEATURE:
<223> OTHER INFORMATION: DERIVED FROM ESCHERICHIA COLI

<400> SEQUENCE: 2
gggttctaga acaatggatc agacatattc tctggag                              37

<210> SEQ ID NO 3
<211> LENGTH: 35
<212> TYPE: DNA
<213> ORGANISM: Escherichia coli

<400> SEQUENCE: 3
ctacgaccgc gtcccacact aaattctcga gttac                                35

<210> SEQ ID NO 4
<211> LENGTH: 49
<212> TYPE: DNA
<213> ORGANISM: Escherichia coli

<400> SEQUENCE: 4
gggttttata tctatggatc agacatattc tctggagtca ttcctcaac                 49

<210> SEQ ID NO 5
<211> LENGTH: 49
<212> TYPE: DNA
<213> ORGANISM: Escherichia coli

<400> SEQUENCE: 5
cccaaaatat agatacctag tctgtataag agaccacagt aaggagttc                 49

<210> SEQ ID NO 6
<211> LENGTH: 12
<212> TYPE: PRT
<213> ORGANISM: Escherichia coli

<400> SEQUENCE: 6

Met Asp Gln Thr Tyr Ser Leu Glu Ser Phe Leu Asn
1               5                   10

<210> SEQ ID NO 7
<211> LENGTH: 38
<212> TYPE: DNA
<213> ORGANISM: Escherichia coli

<400> SEQUENCE: 7
tgcgatgctg gcgcagggtg agatttaagt tgtaaatg                             38

<210> SEQ ID NO 8
<211> LENGTH: 38
```

-continued

```
<212> TYPE: DNA
<213> ORGANISM: Artificial Sequence
<220> FEATURE:
<223> OTHER INFORMATION: DERIVED FROM ESCHERICHIA COLI

<400> SEQUENCE: 8
ccgctacgac cgcgtcccac tctaaattca acatttac                              38

<210> SEQ ID NO 9
<211> LENGTH: 8
<212> TYPE: PRT
<213> ORGANISM: Escherichia coli

<400> SEQUENCE: 9

Ala Met Leu Ala Gln Gly Val Ile
1               5

<210> SEQ ID NO 10
<211> LENGTH: 447
<212> TYPE: PRT
<213> ORGANISM: Escherichia coli

<400> SEQUENCE: 10
```

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser

```
                    275                 280                 285
Arg Asp Gly Arg Val Ala Asp Tyr Ala Lys Glu Phe Gly Leu Val Tyr
            290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Asp His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445

<210> SEQ ID NO 11
<211> LENGTH: 1489
<212> TYPE: DNA
<213> ORGANISM: Artificial Sequence
<220> FEATURE:
<223> OTHER INFORMATION: DERVIED FROM ESCHERICHIA COLI

<400> SEQUENCE: 11
tctagaacaa tggatcagac atattctctg gagtcattcc tcaaccatgt ccaaaagcgc      60
gacccgaatc aaaccgagtt cgcgcaagcc gttcgtgaag taatgaccac actctggcct    120
tttcttgaac aaaatccaaa atatcgccag atgtcattac tggagcgtct ggttgaaccg    180
gagcgcgtga tccagtttcg cgtggtatgg gttgatgatc gcaaccagat acaggtcaac    240
cgtgcatggc gtgtgcagtt cagctctgcc atcggcccgt acaaaggcgg tatgcgcttc    300
catccgtcag ttaacctttc cattctcaaa ttcctcggct tgaacaaac  cttcaaaaat    360 gccctgacta ctctgccgat gggcggtggt aaaggcggca gcgatttcga tccgaaagga    420
aaaagcgaag gtgaagtgat gcgttttgc caggcgctga tgactgaact gtatcgccac    480
ctgggcgcgg ataccgacgt tccggcaggt gatatcgggg ttggtggtcg tgaagtcggc    540
tttatggcgg ggatgatgaa aaagctctcc aacaataccg cctgcgtctt caccggtaag    600 ggccttcat  ttggcggcag tcttattcgc ccggaagcta ccggctacgg tctggttat     660 ttcacagaag caatgctaaa acgccacggt atgggttttg aagggatgcg cgtttccgtt    720
tctggctccg gcaacgtcgc ccagtacgct atcgaaaaag cgatggaatt tggtgctcgt    780
gtgatcactg cgtcagactc cagcggcact gtagttgatg aaagcggatt cacgaaagag    840
aaactggcac gtcttatcga aatcaaagcc agccgcgatg gtcgagtggc agattacgcc    900
aaagaatttg gtctggtcta tctcgaaggc aacagccgt  ggtctctacc ggttgatatc    960
gccctgcctt gcgccaccca gaatgaactg gatgttgacg ccgcgcatca gcttatcgct   1020
aatggcgtta agccgtcgc  cgaaggggca aatatgccga ccaccatcga agcgactgaa   1080
ctgttccagc aggcaggcgt actatttgca ccgggtaaag cggctaatgc tgtggcgtc    1140
```

```
gctacatcgg gcctggaaat ggcacaaaac gctgcgcgcc tgggctggaa agccgagaaa    1200
gttgacgcac gtttgcatca catcatgctg gatatccacc atgcctgtgt tgaccatggt    1260
ggtgaaggtg agcaaaccaa ctacgtgcag ggcgcgaaca ttgccggttt tgtgaaggtt    1320
gccgatgcga tgctggcgca gggtgtgatt taagttgtaa atgcctgatg cgctacgct    1380 tatcaggcct acaaatgggc acaattcatt gcagttacgc tctaatgtag gccgggcaag    1440
cgcagcgccc ccggcaaaat ttcaggcgtt tatgagtatt taagagctc               1489
```

```
<210> SEQ ID NO 12
<211> LENGTH: 1482
<212> TYPE: DNA
<213> ORGANISM: Artificial Sequence
<220> FEATURE:
<223> OTHER INFORMATION: DERIVED FROM ESCHERICHIA COLI

<400> SEQUENCE: 12
gcatgcatca gacatattct ctggagtcat tcctcaacca tgtccaaaag cgcgacccga      60
atcaaaccga gttcgcgcaa gccgttcgtg aagtaatgac cacactctgg ccttttcttg     120
aacaaaatcc aaaatatcgc cagatgtcat tactggagcg tctggttgaa ccggagcgcg     180
tgatccagtt tcgcgtggta tgggttgatg atcgcaacca gatacaggtc aaccgtgcat     240
ggcgtgtgca gttcagctct gccatcggcc cgtacaaagg cggtatgcgc ttccatccgt     300 cagttaaccct ttccattctc aaattcctcg gctttgaaca aaccttcaaa aatgccctga    360
ctactctgcc gatgggcggt ggtaaaggcg gcagcgattt cgatccgaaa ggaaaaagcg     420
aaggtgaagt gatgcgtttt tgccaggcgc tgatgactga actgtatcgc cacctgggcg     480
cggataccga cgttccggca ggtgatatcg gggttggtgg tcgtgaagtc ggctttatgg     540
cggggatgat gaaaaagctc tccaacaata ccgcctgcgt cttcaccggt aagggccttt     600
catttggcgg cagtcttatt cgcccggaag ctaccggcta cggtctggtt tatttcacag     660
aagcaatgct aaaacgccac ggtatgggtt ttgaagggat gcgcgtttcc gtttctggct     720
ccggcaacgt cgcccagtac gctatcgaaa aagcgatgga atttggtgct cgtgtgatca     780
ctgcgtcaga ctccagcggc actgtagttg atgaaagcgg attcacgaaa gagaaactgg     840
cacgtcttat cgaaatcaaa gccagccgcg atggtcgagt ggcagattac gccaaagaat     900
ttggtctggt ctatctcgaa ggccaacagc cgtggtctct accggttgat atcgccctgc     960
cttgcgccac ccagaatgaa ctggatgttg acgccgcgca tcagcttatc gctaatggcg    1020
ttaaagccgt cgccgaaggg gcaaatatgc cgaccaccat cgaagcgact gaactgttcc    1080
agcaggcagg cgtactattt gcaccgggta aagcggctaa tgctggtggc gtcgctacat    1140
cgggcctgga aatggcacaa aacgctgcgc gcctgggctg gaaagccgag aaagttgacg    1200
cacgtttgca tcacatcatg ctggatatcc accatgcctg tgttgaccat ggtggtgaag    1260
gtgagcaaac caactacgtg cagggcgcga acattgccgg ttttgtgaag gttgccgatg    1320
cgatgctggc gcagggtgtg atttaagttg taaatgcctg atgcgctac gcttatcagg     1380 cctacaaatg ggcacaattc attgcagtta cgctctaatg taggccgggc aagcgcagcg    1440
cccccggcaa aatttcaggc gtttatgagt atttaagagc tc                       1482
```

```
<210> SEQ ID NO 13
<211> LENGTH: 1501
<212> TYPE: DNA
<213> ORGANISM: Artificial Sequence
<220> FEATURE:
<223> OTHER INFORMATION: DERIVED FROM ESCHERICHIA COLI
```

<400> SEQUENCE: 13

```
ctgcaggtcg actctagaac aatggatcag acatattctc tggagtcatt cctcaaccat    60
gtccaaaagc gcgacccgaa tcaaaccgag ttcgcgcaag ccgttcgtga agtaatgacc   120
acactctggc cttttcttga acaaaatcca aatatcgcc agatgtcatt actggagcgt    180
ctggttgaac cggagcgcgt gatccagttt cgcgtggtat gggttgatga tcgcaaccag   240
atacaggtca accgtgcatg gcgtgtgcag ttcagctctg ccatcggccc gtacaaaggc   300
ggtatgcgct ccatccgtc agttaacctt tccattctca aattcctcgg ctttgaacaa    360
accttcaaaa atgccctgac tactctgccg atgggcggtg gtaaaggcgg cagcgatttc   420
gatccgaaag gaaaaagcga aggtgaagtg atgcgttttt gccaggcgct gatgactgaa   480
ctgtatcgcc acctgggcgc ggataccgac gttccggcag gtgatatcgg ggttggtggt   540
cgtgaagtcg gctttatggc ggggatgatg aaaaagctct ccaacaatac cgcctgcgtc   600
ttcaccggta agggcctttc atttggcggc agtcttattc gcccggaagc taccggctac   660
ggtctggttt atttcacaga agcaatgcta aaacgccacg gtatgggttt tgaagggatg   720
cgcgtttccg tttctggctc cggcaacgtc gcccagtacg ctatcgaaaa agcgatggaa   780
tttggtgctc gtgtgatcac tgcgtcagac tccagcggca ctgtagttga tgaaagcgga   840
ttcacgaaag agaaactggc acgtcttatc gaaatcaaag ccagccgcga tggtcgagtg   900
gcagattacg ccaaagaatt tggtctggtc tatctcgaag ccaacagcc gtggtctcta    960
ccggttgata tcgccctgcc ttgcgccacc cagaatgaac tggatgttga cgccgcgcat  1020
cagcttatcg ctaatggcgt taaagccgtc gccgaagggg caaatatgcc gaccaccatc  1080
gaagcgactg aactgttcca gcaggcaggc gtactatttg caccgggtaa agcggctaat  1140
gctggtggcg tcgctacatc gggcctggaa atggcacaaa acgctgcgcg cctgggctgg  1200
aaagccgaga agttgacgc acgtttgcat cacatcatgc tggatatcca ccatgcctgt  1260
gttgaccatg gtggtgaagg tgagcaaacc aactacgtgc agggcgcgaa cattgccggt  1320
tttgtgaagg ttgccgatgc gatgctggcc cagggtgtga tttaagttgt aaatgcctga  1380
tggcgctacg cttatcaggc ctacaaatgg gcacaattca ttgcagttac gctctaatgt  1440
aggccgggca agcgcagcgc ccccggcaaa atttcaggcg tttatgagta tttaagagct  1500
c                                                                  1501
```

<210> SEQ ID NO 14
<211> LENGTH: 20
<212> TYPE: DNA
<213> ORGANISM: Artificial Sequence
<220> FEATURE:
<223> OTHER INFORMATION: DERIVED FROM ESCHERICHIA COLI AND STREPTOMYCES
PHAEOCHROMOGENES

<400> SEQUENCE: 14

```
aattcgaacc ccttcgcatg                                                20
```

<210> SEQ ID NO 15
<211> LENGTH: 12
<212> TYPE: DNA
<213> ORGANISM: Artificial Sequence
<220> FEATURE:
<223> OTHER INFORMATION: DERIVED FROM ESCHERICHIA COLI AND STREPTOMYCES
PHAEOCHROMOGENES

<400> SEQUENCE: 15

```
gcttggggaa gc                                                        12
```

METHODS OF USING PLANTS CONTAINING THE GDHA GENE

CROSS REFERENCE TO A RELATED APPLICATION

This application claims priority from U.S. Provisional Application Ser. No. 61/153,576 filed on Feb. 18, 2009, the disclosure of which is hereby incorporated by reference in its entirety.

INCORPORATION OF SEQUENCE LISTING

The entire contents of a paper copy of the "Sequence Listing" and a computer readable form of the sequence listing on diskette, containing the file named 408204_SequenceListing_ST25.txt, which is 15 kilobytes in size and was created on May 6, 2010, are herein incorporated by reference.

BACKGROUND OF THE INVENTION

The present disclosure relates generally to genetically modified plants, and more particularly to methods of using genetically modified crop plants to control the negative effects of certain disease-causing organisms in crop plants.

Members of the saprophytic fungus genus *Aspergillus* produce aflatoxin, a strictly regulated and highly carcinogenic metabolite in plants. Alfatoxin-producing members of *Aspergillus* include *A. flavus*, which commonly afflicts many important food crops including the cereal crops maize, sorghum, pearl millet, rice, wheat, and oilseeds including peanut, soybean, sunflower and cotton. *A. flavus* causes ear rot on corn that results in aflatoxin contamination and the presence of aflatoxin results in a large loss of marketable crop by farmers each year.

The native habitat of *Aspergillus* is in soil, decaying vegetation, hay, and grains undergoing organic decay. It commonly invades all types of organic substrates whenever favorable growth conditions exits. Favorable conditions include a relatively high (7% or higher) moisture content and higher ambient temperatures. Thus, *A. flavus* is widely present under common crop field and storage conditions, and can threaten significant contamination of a crop before harvest or in storage. Moreover, host crops are more susceptible to *Aspergillus* infection and resulting aflatoxin contamination under stressful growing conditions, including drought. At this time, few options are available for effective control of this pathogen. Breeding programs to generate aflatoxin-resistant cultivars of agricultural significance have not met much success. A need remains for methods to prevent and control aflatoxin contamination in the field.

BRIEF SUMMARY OF THE INVENTION

In one aspect, the present disclosure provides a method for reducing aflatoxin accumulation in a crop plant, the method comprising: selecting a crop plant line susceptible to infection with *Aspergillus flavus*; and transforming a plant from the selected plant line with a DNA sequence encoding a bacterial NADP-specific glutamate dehydrogenase enzyme so that the plant expresses the bacterial NADP-specific glutamate dehydrogenase enzyme in an amount sufficient to reduce aflatoxin accumulation in comparison to an amount of aflatoxin accumulation in an untransformed plant from the *A. flavus* susceptible plant line. The method can further comprise growing the plant in conditions associated with *A. flavus* infection of the plant.

In another aspect, the present disclosure provides a method of using a transgenic gdhA+ plant line, the method comprising: controlling aflatoxin contamination of a food crop, wherein the transgenic gdhA+ plant line is a food crop plant line susceptible to *A. flavus* infection, by growing a plant of the transgenic gdhA+ plant line in conditions associated with *A. flavus* infection; measuring the amount of aflatoxin accumulation in the plant; and comparing the amount of aflatoxin accumulation in the plant to the amount of aflatoxin accumulation in a gdhA− plant from the food crop plant line susceptible to *A. flavus* infection.

In another aspect, the present disclosure provides a method of controlling aflatoxin contamination of a crop comprising: selecting an *A. flavus* susceptible crop plant line; transforming a plant from the selected plant line with a DNA sequence encoding a bacterial NADP-specific glutamate dehydrogenase enzyme to produce a transgenic gdhA+ plant line; and growing a plant of the transgenic gdhA+ plant line in conditions associated with *A. flavus* infection.

In another aspect, the present disclosure provides a method of controlling root rot in plants infected with *Fusarium virguliforme*, the method comprising: selecting a *F. virguliforme* susceptible plant line; and transforming a plant from the selected plant line with a DNA sequence encoding a bacterial NADP-specific glutamate dehydrogenase enzyme so that the plant expresses the bacterial NADP-specific glutamate dehydrogenase enzyme in an amount sufficient to reduce root rot in comparison to root rot in an untransformed plant from the *F. virguliforme* susceptible plant line. The method may further comprise growing the plant in conditions associated with *F. virguliforme* infection of the plant.

In another aspect, the present disclosure provides method of using a transgenic gdhA+ plant line, the method comprising: controlling root rot in a crop plant, wherein the transgenic gdhA+ plant line is derived from a crop plant line susceptible to *Fusarium virguliforme* infection, by growing a plant of the transgenic gdhA+ plant line in conditions associated with *F. virguliforme* infection; measuring the amount of root rot in the plant; and comparing the amount of root rot in the plant to the amount of root rot in a gdhA− plant from the *F. virguliforme* susceptible crop plant line.

In another aspect, the present disclosure provides method of controlling root rot in a crop comprising: selecting a *Fusarium virguliforme* susceptible crop plant line; transforming a plant from the selected plant line with a DNA sequence encoding a bacterial NADP-specific glutamate dehydrogenase enzyme to produce a transgenic gdhA+ plant line; and growing a plant of the transgenic gdhA+ plant line in conditions associated with *F. virguliforme* infection.

In another aspect, the present disclosure provides method of screening a crop for plants transformed with a gdhA gene, the method comprising: exposing a plurality of putatively transformed plants to *Aspergillus flavus* or to *Fusarium. virguliforme;* and selecting the plants that show resistance to the effects of the *A. flavus* or *F. virguliforme*. In the method, when the plurality of plants are exposed to *A. flavus*, selecting the plants that show resistance to the effects of the *A. flavus* can comprise selecting plants that show a decreased level of aflatoxin accumulation relative to a reference plant untransformed with the gdhA gene, or can comprise selecting plants that show a decreased level of ear rot relative to a reference plant untransformed with the gdhA gene. In the method, when the plurality of plants are exposed to *F. virguliforme*, selecting the plants that show resistance to the effects of the *F.*

*virguliforme* can comprises selecting plants that show a decreased level of root rot relative to a reference plant untransformed with the gdhA gene.

In any of the above methods, a food crop plant line can be a cereal plant line, including for example a maize, sorghum, pearl millet, rice, or wheat plant line, or an oilseeds plant line, such as a peanut, soybean, sunflower, or cotton plant line. Alternatively, the plant line can be a tobacco plant line. In ay of the above methods, the DNA sequence may comprise the Kozac consensus sequences.

BRIEF DESCRIPTION OF THE DRAWINGS

FIGS. 1A-1C show the DNA sequence of the gdhA gene (SEQ ID NO:1) of *E. coli*.

FIGS. 2A and 2B show the forward primer (panel A, SEQ ID NO:3) at 5' and the reverse primer (panel B, SEQ ID NO:4) at 3' of the non-coding regions (panel A, SEQ ID NOS:5-7, panel B, SEQ ID NOS:8-10) of the gdhA gene. SacI and XbaI restriction enzyme sites are indicated as is the sequence modification to introduce Kozac's consensus sequence (double underline). The bold portion was eliminated as an in RNA destabilizing sequence.

FIG. 3 shows the amino acid sequence (SEQ ID NO:11) of *E. coli* gdhA enzyme expressed in corn.

FIGS. 6A1, 6A2 and 6A3 show the DNA (SEQ ID NO:12) sequence of the mutagenized gdhA gene used for plant expression in corn.

FIGS. 6B1, 6B2 and 6B3 show the DNA sequence (SEQ ID NO:13) including the SphI site of the mutagenized gdhA gene used for plant expression in corn.

FIGS. 7A1, 7A2 and 7A3 shows the mutagenized gdhA gene (SEQ ID NO:14) with the added restriction sites for use in *Zea mays*.

FIG. 8 shows the 3' EcoRI SphI adapter (SEQ ID NOS:15-16) between nosT and plasmid for corn transformation.

DETAILED DESCRIPTION OF THE INVENTION

Figure 4:
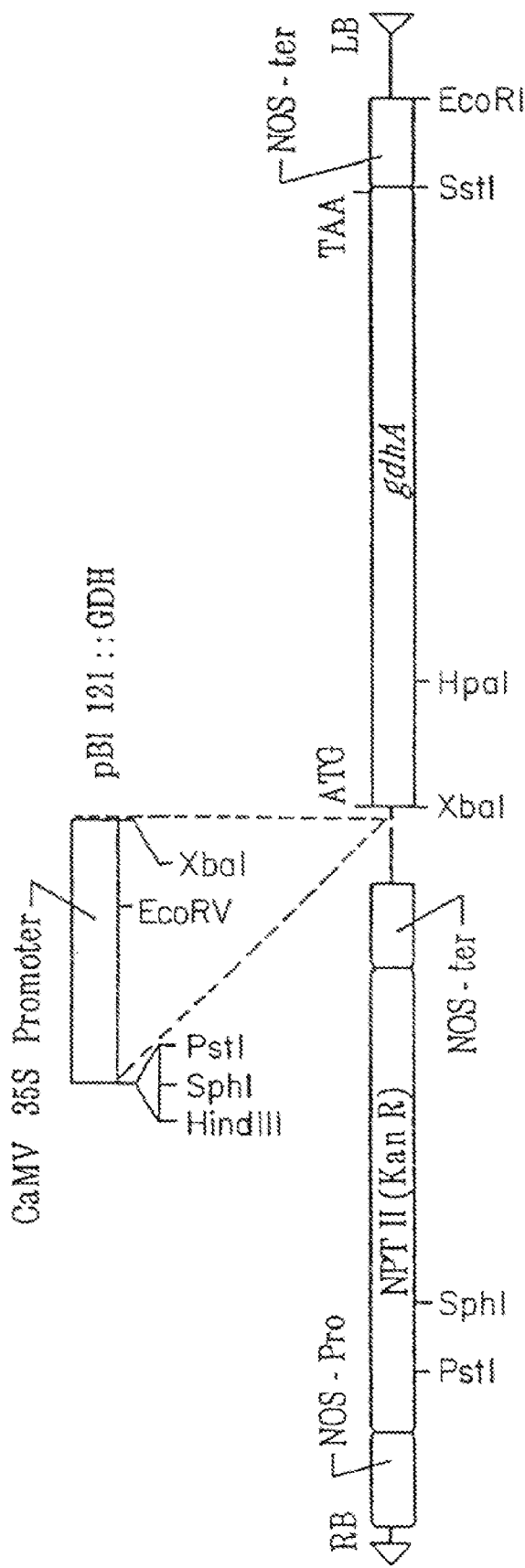
FIG. 4 shows a linear map of the plasmid vector pBI121: GDH1 developed in Example I. The plasmid has the uidA gene removed and the gdhA gene inserted.
Figure 5:
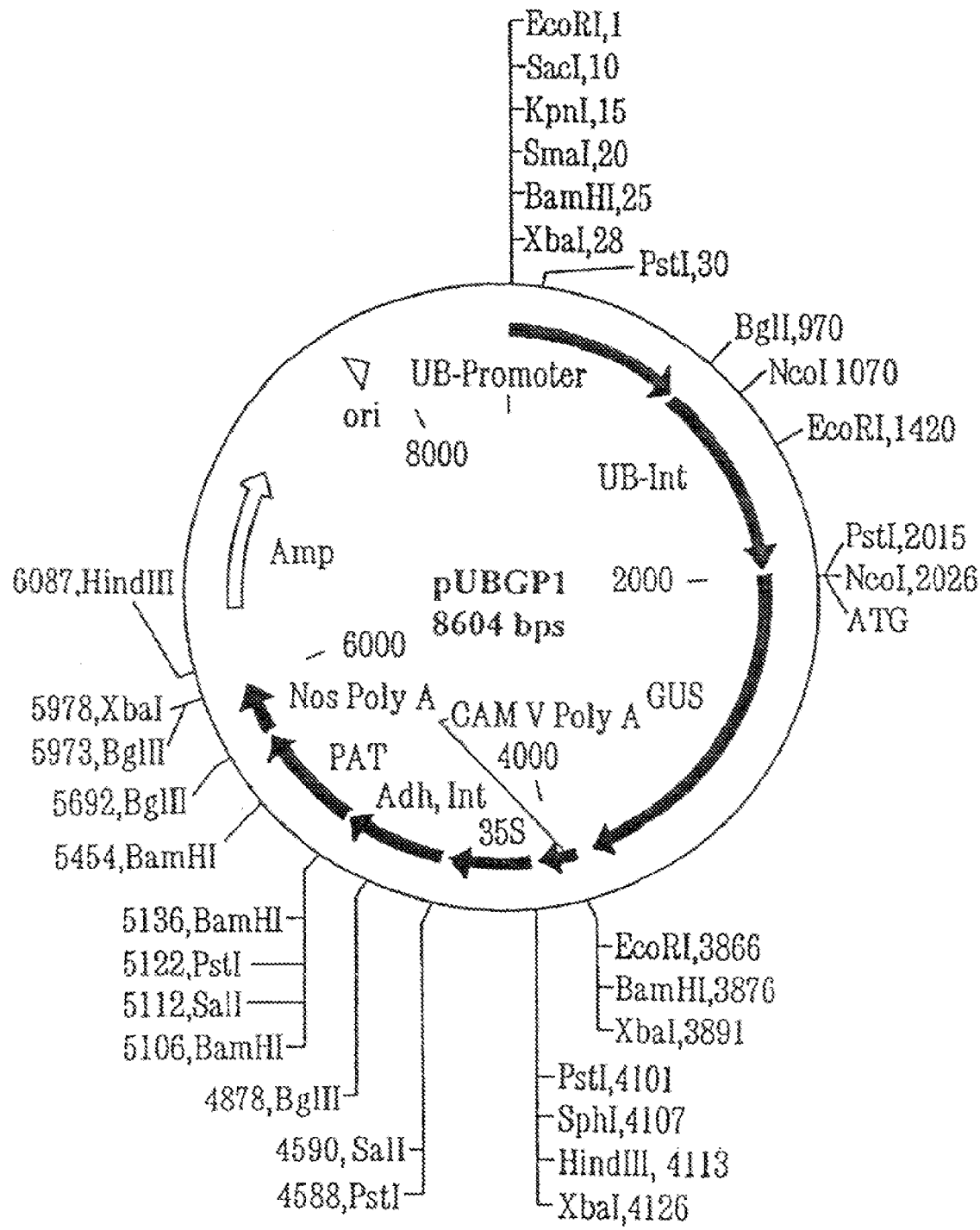
FIG. 5 shows a circular map of the plasmid vector pUBGP1 used in the examples as starting material and a control for plasmids useful in *Zea mays*.
Figure 7B:
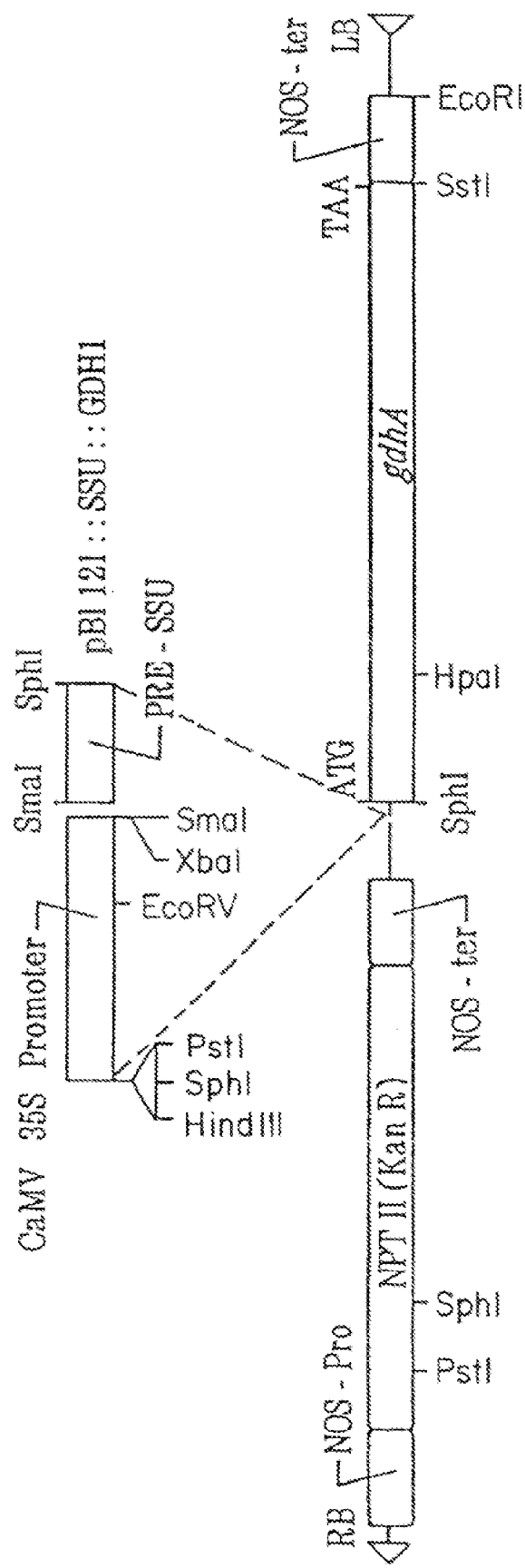
FIG. 7B shows a linear plasmid map of pBI121::SSU:: GDH1.
Figure 9:
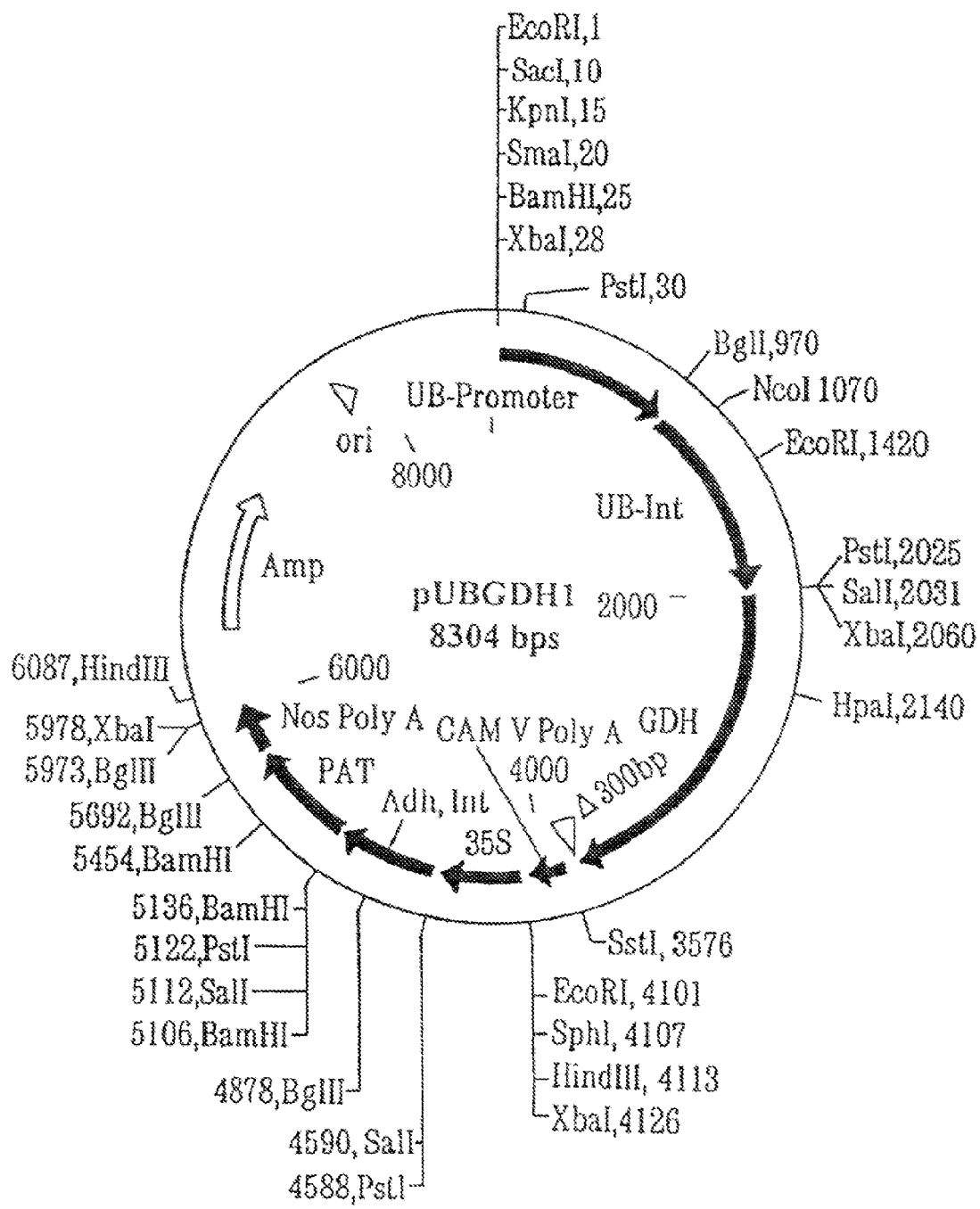
FIG. 9 shows a circular map of the plasmid pUBGDH1 wherein UB is ubiquitin.

Described herein are the results of successful experiments that show for the first time that corn plants transformed with the gdhA gene (gdhA+ corn) are resistant to aflatoxin accumulation. Additionally, results described herein show that corn and tobacco plants transformed with the gdhA gene (gdhA+ plant) are also resistant to root rot following infection with *Fusarium virguliforme*. These surprising findings provide the basis in part for various methods described herein. Additionally, the discovery provides the basis for the development of new markers for novel sources of resistance to ear rot, aflatoxin accumulation and root rot, and establishes the gdhA gene as an important tool for marker-assisted breeding programs.

More specifically, laboratory assays show that kernels from corn plants with the gdhA gene exhibit a reduction in the conidiation of *A. flavus*. The findings indicate that the fungus produces significantly less conidia on the embryos of gdhA+ corn kernels than on those of gdhA− kernels. As a further advantage, the aflatoxin resistance conferred on plants expressing the gdhA gene is coincident with other desirable characteristics of the plants, including higher tolerance to stressful environmental conditions, resistance to certain herbicides, and resistance to root rot, together with nutritional equivalence to unaltered corn.

Methods of Producing Transgenic Plants Containing the gdhA Gene

Plants containing a bacterial gdhA gene and their use in growing a transgenic crop that is resistant to herbicides of the phosphinothricin class have previously been described in U.S. Pat. Nos. 5,998,700 and 6,329,573 both under the title "Plants Containing a Bacterial gdhA Gene and Methods of Use Thereof." Described herein are methods for controlling alfatoxin contamination in plants susceptible to *Aspergillus*. The findings disclosed herein also establish that the gdhA gene can be used as a specific marker in plant breeding programs seeking to reduce aflatoxin accumulation in plants infected by *Aspergillus*.

As used herein, the term transgenic plant refers to plants having exogenous genetic sequences that are introduced into the genome of a plant by a transformation method and the progeny thereof.

As used herein, the term transformation methods refers to means for integrating new genetic coding sequences by the incorporation of these sequences into a plant of new genetic sequences through man's assistance. Though there are a large number of known methods to transform plants, certain types of plants are more amenable to transformation than are others. For example, corn is a readily transformable monocot and tobacco is a readily transformable dicot. The basic steps of transforming plants are known in the art. These steps are concisely outlined for example in U.S. Pat. No. 5,484,956 "Fertile Transgenic *Zea mays* Plants Comprising Heterologous DNA Encoding Bacillus Thuringiensis Endotoxin" and U.S. Pat. No. 5,489,520 "Process of Producing Fertile *Zea mays* Plants and Progeny Comprising a Gene Encoding Phosphinothricin Acetyl Transferase". A description of a method for transforming tobacco (*Nicotiana tabacum* var. *Petite Havana*) and *Zea mays* plants with the gdhA gene is provided in U.S. Pat. No. 6,329,573 "Plants Containing the gdhA Gene and Methods of Use Thereof".

Tobacco and corn lines that express a bacterial NADP-dependent glutamate dehydogenase have been shown to have a high tolerance to glucosinate-type herbicides, and the altered corn lines provide increased grain biomass production in dry environments while retaining nutritional equivalence to unaltered corn. (See U.S. Pat Nos. 5,998,700 and 6,329, 573).

Plant cells such as maize can be transformed by a number of different techniques. Some of these techniques have been described and are known in the art including maize pollen transformation (see University of Toledo 1993 U.S. Pat. No. 5,177,010); biolistic gun technology (see U.S. Pat. No. 5,484, 956); Whiskers technology (see U.S. Pat. Nos. 5,464,765 and 5,302,523); electroporation; *Agrobacterium* (see 1996 article on transformation of maize cells in Nature Biotechnology, Volume 14, June 1996) along with numerous other methods which may have slightly lower efficiency rates then those listed. Some of these methods require specific types of cells and other methods can be practiced on any number of cell types.

The use of pollen, cotyledons, meristems and ovum as the target issue can eliminate the need for extensive tissue culture work. However, the present state of the technology does not provide very efficient use of this material.

Generally, cells derived from meristematic tissue are useful. Zygotic embryos can also be used. Additionally, the method of transformation of meristematic cells of cereal is also taught in PCT application WO96/04392. Any of the various cell lines, tissues, plants and plant parts can and have been transformed by those having knowledge in the art. Methods of preparing callus from various plants are well known in the art and specific methods are detailed in patents and references used by those skilled in the art.

Cultures can be initiated from most of the above identified tissue. The material used herein was zygotic embryos. The embryos are harvested and then either transformed or placed in media. Osmotic cell treatments may be given to enhance particle penetration, cell survival, etc.

The only true requirement of the transformed material is that it can form a fertile transformed plant. The gene can be used to transform plants including both monocots and dicots. Plants that are produced as field crops are of particular interest and particularly those crops susceptible to mycotoxin-producing fungi such as the aflatoxin-producing fungus *Aspergillus*. These crops include for example the cereal crops maize, sorghum, pearl millet, rice, wheat, and the oilseeds peanut, soybean, sunflower and cotton, among others. Also of interest are plants susceptible to or *Fusarium virguliforme*, including tobacco plants including but not limited to *Nicotiana tabacum*. The gdhA gene can come from various non-plant genes (such as bacteria, yeast, animals, and viruses). The gdhA gene can also come from plants. The gene insert used herein was either an *E. coli* glutamate dehydrogenase gene or a mutagenized version thereof. Another gdhA gene of particular interest is from *Chlorella*.

The DNA used for transformation of these plants clearly may be circular, linear, double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

The regulatory promoters employed in the present disclosure can be constitutive such as CaMv35S for dicots and polyubiquitin for monocots or tissue specific promoters such as CAB promoters, etc. Promoters may include but are not limited to octopine synthase, nopaline synthase, CaMv19S, and mannopine synthase. These regulatory sequences can be combined with introns, terminators, enhancers, leader sequences and the like in the material used for transformation.

The isolated DNA is then transformed into the plant. Many dicots can easily be transformed with *Agrobacterium*. Some monocots are more difficult to transform. As previously noted, there are a number of useful transformation processes. The improvements in transformation technology are beginning to eliminate the need to regenerate plants from cells. Since 1986, the transformation of pollen has been published and recently the transformation of plant meristems has been published. The transformation of ovum, pollen, and seedlings meristem greatly reduce the difficulties associated with cell regeneration of different plants or genotypes within a plant can be present.

The most common method of transformation is referred to as gunning or microprojectile bombardment. This biolistic process has small gold-coated particles coated with DNA shot into the transformable material. Techniques for gunning DNA into cells, tissue, callus, embryos, and the like are well known in the prior art.

After the transformation of the plant material is complete, the next step is identifying the cells or material that has been transformed. In some cases, a screenable marker can be employed, such as the beta-glucuronidase gene of the uidA locus of *E. coli*. Thus, the cells expressing the colored protein are selected for either regeneration or further use. In many cases, the transformed material is identified by a selectable marker. The putatively transformed material is exposed to a toxic agent, such as *A. flavus* or *Fusarium virguliforme*, in varying amounts. The cells that are not transformed with the selectable marker that provides resistance to the toxic agent die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. The present disclosure thus provides a selectable marker for identifying transformed plant materials in the presence of *Aspergillus flavus* or *Fusarium virguliforme*. In fact, when combined with the PAT or bar gene which is known to give resistance to phosphinothricin, the cells or plants after exposure to the herbicide often evidence increased growth by weight, and appear more vigorous and healthy.

If the transformed material consists of cell lines then these lines are regenerated into plants. The cell lines are treated to induce tissue differentiation. Methods of regeneration of cellular material have been well known in the art since early 1982. The plants resulting from either the transformation process or the regeneration process are transgenic plants.

To evaluate various plant lines for susceptibility to *A. flavus* or *Fusarium virguliforme*, and the effect of gdhA expression in transformed lines, various lines and hybrids can be tested as provided in the Examples. For example, various gdhA− corn lines can be tested as described in Example 4 to select lines that demonstrate at least a moderate level of ear rot following exposure to *Aspergillus*. Such lines can then be used to evaluate, as described in the Examples, the effect of transformation with gdhA on aflatoxin resistance in each line. Exemplary corn lines are listed in Table 1, which is an exemplary seed inventory at Southern Illinois University at Carbondale (Carbondale, Ill.).

TABLE 1

| Name | Number |
|---|---|
| SN 3-3 1-9 | 182 |
| SN 4 | 160 |
| 5 6-5 | 3 |
| SN 14-5 1-9 | 123 |
| SN 2-3 G | 102 |
| SN 12-5 G | 56 |
| BDxLL3-272 S-42 #18 | 300/197 |
| H99 | 140 |
| SN 3-1 1-9 | 162 |
| H99 + Pat + GDH = LL3xS | 118 |
| SN 12-4 G | 125 |
| SN 12-6 1-9 | 46 |
| SN 12-7 | 9 |
| SN 14-6 1-9 | 113 |
| SN 14-7 1-9 | 83 |
| SN 14-8 1-9 | 40 |
| SN 3-3 1-9 | 185 |
| SN 14-10 1-9 | Medium Amount |

TABLE 1-continued

| Name | Number |
| --- | --- |
| SN 12-8 | 9 |
| SN 2A-1 1-9 | 206 |
| SN 7-3 1-9 | 172 |
| SN 2-4 | 165 |
| SN 14-9 1-9 | 20 |
| SN 14-4 1-9 | 142 |
| SN 2A-2 1-9 | 145 |
| SN 12-3 | 153 |
| SN 2A-3 1-9 | 140 |
| SN 14-3 1-9 | 241 |
| SN 10 | 2 |
| GDH Inbred 5-05 | Large Amount |
| LL3xS | 370 |
| SN 15 | 526 |
| H99 | 19 |
| LL3xS | 556 |
| LL3xS | 472 |
| SN 4 | 91 |
| 10 | 70 |
| SN 3 | 18 |
| SN 3 | 3 |
| SN 7-4 | 140 |
| SN 6 | 1 |
| 3 | 1 |
| H99 | 56 |
| SN 3 | 2 |
| SN 4 | 17 |
| 10 | 6 |
| 10 | 50 |
| DLxS 5-8 | 0 |
| SN 2-2 | 217 |
| SN 14-2 | 238 |
| SN 14-1 1-9 | 213 |
| SN 12-1 | 208 |
| SN 7-2 | 191 |
| SN 12-2 1-9 | 277 |
| SN 2-1 | Medium Amount |
| SN 7-1 1-9 | 112 |
| Self LL3-7755 | 0 |
| LL9-37ASelf172 | 0 |
| LL9-37ASelf127 | 0 |
| LL9-37ASelf121 | 0 |
| BD195 LL2-63-Self12 | 0 |
| LL9-37ASelf124 | 0 |
| LL2-63-Self-1 | 0 |
| LL2-63-Self-12 | 0 |
| LL3-240xSelf-11 | 128 |
| BDxLL32725-425 | 300/199 |
| BD141 LL9-37A | 0 |
| LL2-63-Self-12 | 0 |
| LL9-37A-Self-122 | 0 |
| LL9-37A-Self-124 | 0 |
| LL9-37A-Self-132 | 0 |
| BDxLL3-2725-42-4x5 | 437/206 |
| LL3-7755-130x5-6 | 1 |
| BD195 LL2-63-Self12 | 0 |
| BD141 LL9-37A | 0 |
| LL3-240-Self-14 | 10 |
| LL3-7755-130xS-4 | 1 |
| LL3-7755-130xS-9 | 0 |
| LL3-2405 | 0 |
| LL3-240 Self 20 | 0 |
| LL3-240 Self 21 | 0 |
| LL3-240 Self 1 | 0 |
| LL3-7755-130xS-3 | 0 |
| LL3-7755-130xS-5 | 0 |
| LL4-6828-9-5 | 0 |
| LL4-6825-10xS-10 | 0 |
| LL4-6825-2x5-10 | 0 |
| LL4-6825-20xS-2 | 0 |
| LL4-6825-8-5 | 0 |
| LL4-6825-2xS-6 | 0 |
| LL4-6825-5xS-8 | 0 |
| LL4-6825-22S-1 | 0 |
| LL8-67xH-6xS-8 | 1 |
| LL8-67xH-2x5-11 | 10 |
| LL8-67xH-6xS-8 | 10 |
| LL4-6825Self-22xS-2 | 10 |
| LL8-67xH-5xS-19 | 20 |
| LL8-67xH-6xS-6 | 5 |
| LL8-67xH-2xS-18 | 20 |
| LL3-240xSelf-8 | 100 |
| LL3-240xSelf-18 | 100 |
| LL9-37A-Self-125 | 230/130 |
| LL8-67xH99-11-1 | 5 |
| LL3-240xSelf-22 | 5 |
| LL3-240xSelf-24 | 50 |
| LL17-463-Self-133 | 0 |
| LL17-463-S-132 | 0 |
| LL8-67xH-6-S-3 | 5 |
| LL8-67xH-6xS-5 | 10 |
| LL9-37A-Self-118 | 231/200 |
| LL9-37A-Self-120 | 220/120 |
| LL8-67xH-2xS-6 | 10 |
| LL9-37A-Self-119 | 227/100 |
| LL8-67xH-2xS-7 | 20 |
| LL9-37A-Self-126 | 100/100 |
| Self LL8-67xH-6x5-1 | 100 |
| LL4-6825-2 | 0 |
| LL4-6825-8xS-3 | 0 |
| LL8-67xH-2xS-15 | 0 |
| LL8-67xH-2-5-16 | 0 |
| LL8-67xH-S-2 | 0 |
| LL8-67xH-2xS-19 | 0 |
| LL8-67xH-2xS-10 | 0 |

\* = more than one sample;
SN = Scott Nolte

Similarly, various gdhA− plant lines, such as a tobacco plant line, can be tested as described in Example 8 to select lines that demonstrate at least a moderate level of root rot following exposure to *Fusarium virguliforme*. Untransformed and transformed plants from such lines can be used to evaluate, as described in the Examples, the effect of transformation with gdhA on root rot resistance in each line. Any plant from the known wide host range in which *F. virguliforme* causes root rot can be used, including for example legumes such as soybean, pea, snap bean, alfalfa, and green bean.

Expression of gdhA in transformed plants impacts certain metabolic pathways. The levels of plant metabolites in gdhA+ and gdhA− plants can be compared to help establish the impact of gdhA expression on plant function. Tissue from gdhA+ plants is extracted, analyzed for the levels of selected metabolites and those levels compared to those in unaltered plants (gdhA$^-$).

According to the methods disclosed herein, expression of the bacterial NADP-specific glutamate dehydrogenase in transformed plants is in an amount sufficient to reduce or eliminate the effects of *Aspergillus flavus* or *Fusarium virguliforme* in comparison to the effects of these infectious agents observed in an untransformed plant from the susceptible plant line. That a sufficient amount of expression has been achieved is readily determined, for example, by methods described herein. For example, a sufficient amount of bacterial NADP-specific glutamate dehydrogenase expression in transformed plants is achieved when plants demonstrate a reduced severity of ear rot following exposure to *A. flavus*, in comparison to untransformed plants also exposed to *A. flavus*. Alternatively or in addition, a sufficient amount of bacterial NADP-specific glutamate dehydrogenase expression in transformed plants is achieved when plants demonstrate a reduction in aflatoxin accumulation following exposure to *A. flavus*, in comparison to untransformed plants also exposed to *A. flavus*. Measures of ear rot severity and aflatoxin accumulation are readily obtained using methods described herein or as otherwise well-known in the art. For example, positive or negative reference or cut-off values for ear rot severity or may be established using the prior established effects of *A. flavus* on transformed or untransformed plants. Similarly, a sufficient amount of bacterial NADP-specific glutamate dehydrogenase expression in transformed plants is achieved when plants demonstrate a reduction in severity of root rot following exposure to *F. virguliforme*, in comparison to untransformed plants also exposed to *F. virguliforme*. Measures of root rot severity are readily obtained using methods described herein or as otherwise well-known in the art.

Figure 10:
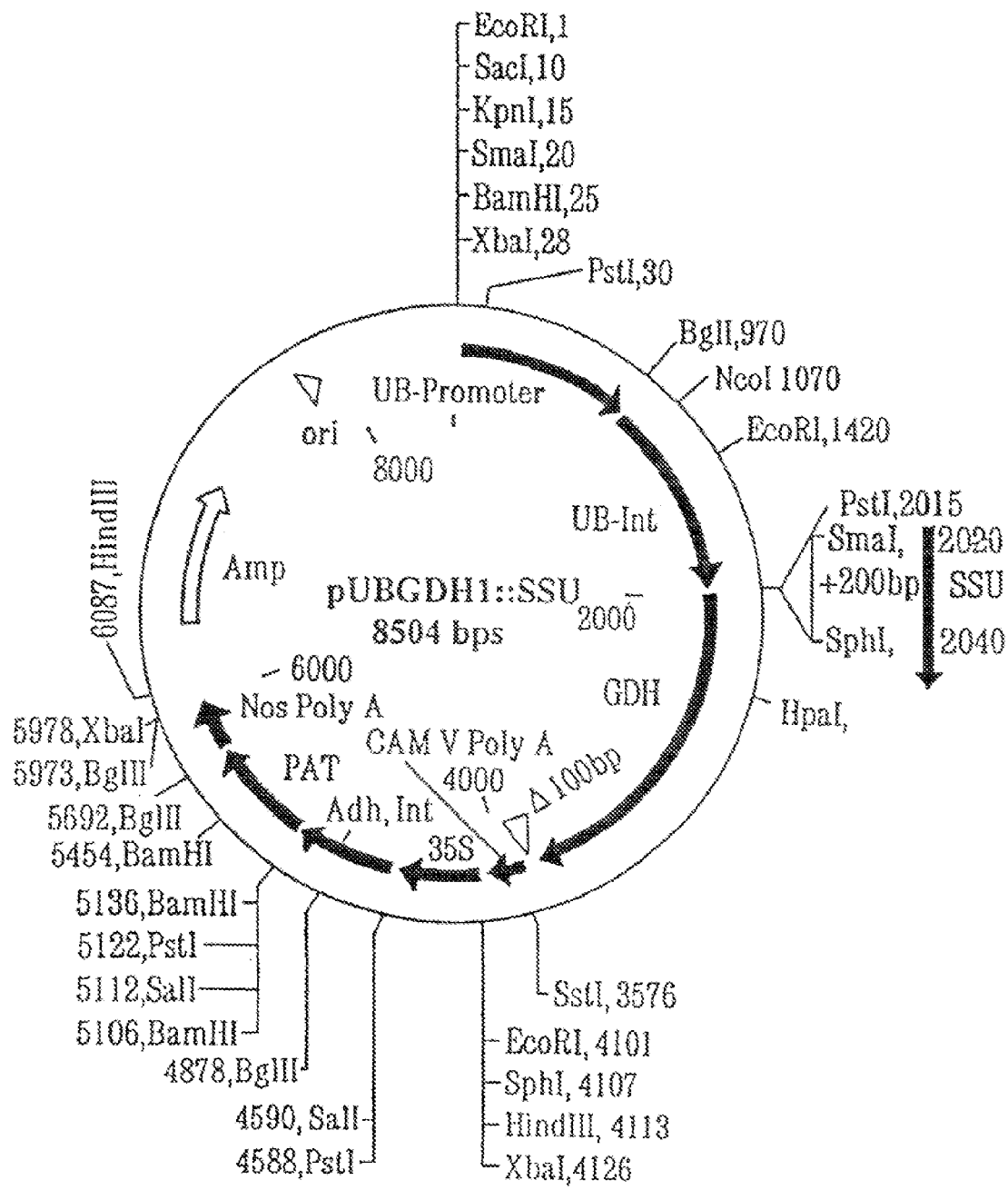
FIG. 10 shows a circular map of the plasmid vector PUB-GDHI with the pre SS unit.
Figure 11:
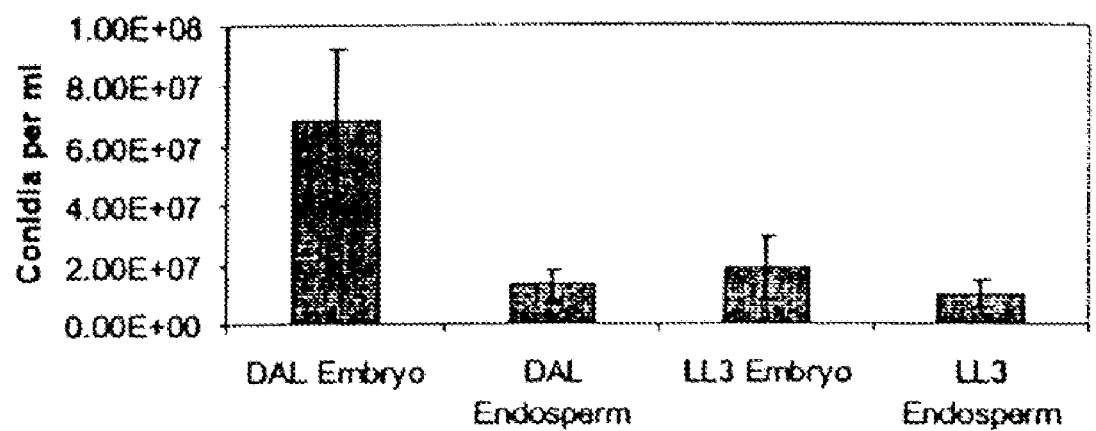
FIG. 11 shows a bar graph comparing conidia production by *A. flavus* in LL3 corn kernels (gdhA+) and in DAL corn kernels (gdhA−).

The following examples are thus included to demonstrate various aspects and iterations of the present disclosure. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

In the examples set forth herein below, the gdhA gene refers to the DNA sequence of the gdhA gene of *Escherichia coli*, which encodes a 447 amino acid polypeptide subunit of NADP-specific glutamate dehydrogenase as presented in 1982 in *Nucleic Acids Research*, Volume II, Number 15, 1983. The present examples will illustrate the gdhA gene transformed into a monocot (corn) plant, and a dicot (tobacco) plant. A complete description of a method for transforming a dicot plant (the tobacco *Nicotiana tabacum* var. Petite Havana) with the gdhA gene is also provided for example in U.S. Pat. No. 6,329,573, "Plants Containing the gdhA Gene and Methods of Use Thereof".

Example 1

Plasmids

A. Sequences and Formation of Plasmid

A bacterial glutamate dehydrogenase (gdhA) gene, shown in FIG. 1 (SEQ ID NO: 1), derived from *E. coli*, was altered for expression in plant cells by polymerase chain reaction. The 5' non-coding region was modified by the introduction of an XbaI restriction enzyme site. Kozac's consensus sequence (Lutcke et. al. 1987) was also added to the 5' region (SEQ ID NOS: 4-6) to allow high levels of expression in plant cells. The 3' non-coding region (SEQ ID NOS: 7-9) was altered to stabilize the mRNA and ensure appropriate polyadenylation and a SacI restriction site was added. These primer sequences, shown in FIG. 2 (SEQ ID NOS: 2-3), are the introduction of the restriction sites and the Kozac's consensus sequence along with the destabilizing portions. The amino acid sequence of the gdhA gene was retained. PCR was carried out in an automated thermal cycler (MJ Research, St. Louis, Mo.) for 25 cycles (each cycle consisting of 1 min. at 92.degree. C., 1 min. at 60.degree. C. and 3 min. at 72.degree. C.). Reactions contained 200 ng of pBG1 (Mattaj et. al. 1981), 0.9 mM) MgCL.sub.2, dNTPs, 1 unit of Taq polymerase (Promega, Madison, Wis.) and 1 nM of each primer. The PCR products were gel purified and DNA bands recovered from agarose gels using GeneClean (Bio101, Hercules, Calif.). XbaI and SacI were used with the band which was digested. This process provided single strand complementary end for ligation into a vector.

The uidA gene from pBI121.1 (pBI121 plasmid is commercially available from Clontech Laboratories, Palo Alto, Calif.), (Jefferson, 1987) was removed by restriction digest with XbaI and SacI and the gel eluted PCR products were ligated into the resulting 9.7 kb fragment of pBI121.1. The amino acid sequence of the GDH enzyme produced by the gdhA gene is shown in (SEQ ID NO:10) FIG. 3. The plasmids were then transformed into competent *E. coli* cells (Top10 Invitrogen, San Diego, Calif.) via electroporation. Colony hybridization was used to detect colonies with the modified gdhA inserts (FIG. 3). Plasmids from the hybridizing colonies were used to transform competent *Agrobacterium tumefaciens* (Sambrook et. al. 1989) strains LBA4404 (Hooykas 1981) and EHA101 (Nester 1984).

B. Construction of Plasmids to Transfer *E. Coli* gdhA to *Zea mays*

The pBI121::GDH plasmid (shown in FIG. 4) was not particularly suitable for use in *Zea mays*. Thus, the plasmid pUBGPI (shown in FIG. 5) which is a vector suitable for transformation of *Zea mays* and foreign gene expression was employed.

The modified *E. coli* gdhA gene (shown in FIG. 6A, SEQ ID NO:11) was readily transferred to pUBGP1 to replace the GUS (uidA) gene by restriction digestion, gel purification of appropriate fragments and ligation as follows. Digestion of pBI121::GDH (shown in FIG. 4) with XbaI and EcoRI allowed recovery of gdhA::nosT as a 1.6 kbp fragment. Ligation with EcoRI XbaI digested pUC18 produced the plasmid pUCGDH1 which was amplified in *E. coli* DH5. Digestion of pUCGDH1 with PstI and EcoRII allowed recovery of the gdhA::nosT as a 1.6 kbp fragment. This mutagenized gdhA gene with the added linker restriction sites is shown in FIG. 7A (SEQ ID NO:13). Digestion of pUBGP1 with NcoI and SphI allowed recovery of the vector minus GUS::nosT as the 1.0 and 5.6 kbp fragments. Digestion of the 1.0 kbp fragment with PstI removed one NcoI site (and an inappropriate ATG codon). The 1.0 and 5.6 kbp pUBGPI fragments were ligated with the 1.6 kbp fragment from pBI121::GDH1 and an EcoRI/SphI adapter (shown in FIG. 8 as SEQ ID NOS:14-15).

The 3' EcoRI SphI adapter is between nosT and the plasmid for corn transformation. This gives pUBGDH1 (shown in FIG. 9) which was amplified in *E. coli* DH5.

The plasmid pUBGDH1 (shown in FIG. 9) was purified as DNA from *E. coli*, and 1 μg were used for transformation of *Zea mays* inbred line H99 by biolistics.

Example 2

Construction of Plasmid to Target the *E. coli* gdhA to Chloroplasts in Corn Because the pBI121::GDH plasmid was not suitable for *Zea mays* transformation or gene expression, another plasmid vector was used to achieve gdhA gene transfer and expression. The 1.8 kbp SmaI to EcoRI fragment of pBI121::SSU::GDH1 was isolated and ligated with an EcoRI/SmaI adapter and SmaI digested pUC18. This produced the plasmid pUCSSUGDH1 which was amplified in *E. coli* DH5. Digestion of pUCSSUGDH1 with SmaI allowed recovery of the SSU::gdhA::nosT as a 1.8 kbp fragment (FIG. 7B). Digestion of pUBGP1 with NcoI and SphI allowed recovery of the vector minus GUS::nosT as the 1.0 and 5.6 kbp fragments. Digestion of the 1.0 kbp fragment with PstI removed the NcoI site (and an inappropriate ATG codon). The 1.0 and 5.6 kbp pUBGPI fragments were ligated with the 1.8 kbp fragment from pUC-SSUGDH1 and an PstI/SmaI adapter to give pUBSSUGDH1 (FIG. 10) which was amplified in *E. coli* DH5. The plasmid pUBSSUGDH1 was purified as DNA from *E. coli*, and 1 μg used for transformation of the *Zea mays* inbred line by biolistics.

Example 3

Effect of gdhA+ Corn on Levels of Selected Metabolites

Corn kernels from the gdhA⁻ and gdhA⁺ corn lines were analyzed for levels of a variety metabolites and those levels compared. Table 2 lists the names and molecular formulae (in comparable form) of seven metabolites that were present at different levels in gdhA⁺ corn compared to gdhA⁻ corn. The third column lists the factor for relative level of the metabolite in gdhA⁺ corn as compared to the level observed in gdhA-⁻ corn.

TABLE 2

| Metabolite | Molecular formula in comparable form | Factor for relative level in gdhA⁺ vs. gdhA corn |
|---|---|---|
| DL-malic acid; Threonate | $C_4H_6N_0O_5P_0S_0Cl_0$ | 2.4 |
| 4-Chloro-2-methylthiopyrimidine | $C_5H_5N_2O_0P_0S_1Cl_1$ | 0.4 |
| 4-hydroxybutyl phosphate | $C_4H_{11}N_0O_5P_1S_0Cl_0$ | 0.4 |
| Linolenic acid | $C_{18}H_{30}N_0O_2P_0S_0Cl_0$ | 2 |
| Chlorogenic acid | $C_{16}H18N_0O_9P_0S_0Cl_0$ | 2 |
| Linoleic acid | $C_{18}H_{32}N_0O_2P_0S_0Cl_0$ | 0.8 |
| D-glucose | $C_6H_{12}N_0O_6P_0S_0Cl_0$ | 1.9 |

Example 4

Effect of gdhA+ Corn on Conidiation of *Aspergillus flavus*

Corn kernels from the corn lines DAL (gdhA⁻) and LL3 (gdhA⁺) were inoculated with conidia from the aflatoxin B1 (AFB1) producing *A. flavus* isolate NRLL3357. Endosperms and embryos of corn kernels differ substantially in their chemical composition; endosperms are composed mainly of starch and other carbohydrates, whereas embryos are richer in lipids and proteins. Either the endosperms or the embryos of kernels were wounded by inserting a 26 G hypodermic needle to a depth of 1 mi. The endosperm-wounded kernels were dissected, separating the embryo and endosperm tissues, prior to inoculation. Wounded kernels were surface sterilized with 5% sodium hypochlorite, inoculated with 103 conidia of *A. flavus* to the wound site, and incubated at 28° C. in a moist chamber to enhance fungal growth. Innoculation of corn kernels with conidia was performed on either embryos or endosperms of corn kernels. Each experimental unit consisted of three kernels placed in a Petri-plate. Three-kernel samples were collected 14 days after inoculation, and fungal growth was assessed by counting the produced conidia using a hemacytometer. FIG. 11 is a bar graph comparing production of conidia by *A. flavus* on the embryos of LL3 corn kernels (gdhA+) and on DAL corn kernels (ghdA$^-$). Conidiation was reduced by 73% compared to the conidiation on DAL corn kernels (ghdA$^-$). Conidiation on DAL and LL3 endosperm was not however significantly different. These findings indicate that the expression of gdhA in transgenic corn alters the lipid composition of the kernels. Such a change in lipid compositions is expected to be more substantial in the lipid rich embryos than in the starch/carbohydrate rich endosperm.

Given the well-established link between conidation and toxin biosynthesis, the reduction of *A. flavus* conidiation in transgenic (gdhA+) corn plants was expected to produce a reduction in accumulation of the mycotoxin (aflatoxin B1).

Example 5

Assessment of Resistance of Planted gdhA+ Corn to Colonization by *A. flavus* and Accumulation of AFB1)

Several corn lines were assessed for *A. flavus* colonization and AFB1 accumulation during the 2006 and 2007 growing seasons (Table 3). Corn lines used in field studies were the inbreds LL3-272, LL3-775 and DL1-005, all of which are transgenic lines developed at Southern Illinois University at Carbondale. LL3-272 and LL3-775 express gdhA whereas DL1-005 does not. The hybrid line B73xLL3-272 was developed at SIU by crossing B73 with LL3-272 (gdhA+). The corn line M182 was known to be resistant to *A. flavus* whereas the inbred B73 was known to be susceptible to the fungus.

TABLE 3

| Genotype | Presence of gdh | Susceptibility to *A. flavus* |
|---|---|---|
| B73xLL3-271 | Yes | Unknown |
| LL3-272 | Yes | Unknown |
| LL3-775 | Yes | Unknown |
| DL1-005 | No | Unknown |
| M182 | No | No |
| B73 | No | Yes |

Hybrids were planted in single-row plots with 12 plants per row. Plots were arranged in a randomized complete block design with 3 replications. Primary ears of each plant were inoculated 20 days following the mid-silk growth stage with a conidial suspension of *A. flavus* isolate NRLL3357 using the pinbar method (see Zummo and Scott, Plant Disease, 1992, 76:771-773). Ears were harvested 60 days after midsilk and visually rated for rotting. Ears were harvested 60 days after mid-silk and visually rated for rotting on a scale of 1 to 10, where 1 corresponded to 10% of inoculated area rotted, and 10 indicated 100% of inoculated area rotted. All ears tested were at least minimally susceptible, i.e. showed at least some sign of infection. However, gdhA+ lines showed significantly less rot.

Example 6

Assessment of Resistance of Planted gdhA+ Corn to Colonization by *A. flavus* and Accumulation of Aflatoxin B1 (AFB1)

A total of fourteen corn lines were assessed for *A. flavus* colonization and AFB1 accumulation during the 2006 and 2007 growing seasons. All lines were previously shown to be susceptible to *A. flavus*. Six of these lines, four hybrids and two isolines, were transgenic expressing the gdhA gene (gdhA+). The plants were planted in single-row plots with twelve plants per row. Plots were arranged in a randomized complete block design with two replications. Primary ears of each plant were inoculated twenty days following the midsilk growth stage with a conidial suspension of *A. flavus* isolate NRLL3357 using the pinbar method (Zummo and Scott 1992). Ears were harvested 60 days after midsilk and visually rated for rotting on a scale of 1 to 10, where 1 corresponded to 10% of inoculated area rotted, and 10 indicated 100% of inoculated area rotted. Wounded kernels from the inoculated area of the ear and the surrounding two rows were manually collected and analyzed for aflatoxin B1 using High Pressure Liquid Chromatography (HPLC).

Results are reported in Table 4. Inbred line LL3-272 is a transgenic line developed at Southern Illinois University at Carbondale. LL-3, LL3-2, LL3-7, LL200, LL3-272 are lines from different event transformations (selfed at least three times). DL5 is a line from corn transformed with an empty vector. Controls included Mp420, Pioneer, B73, H99 and DL5. H99 is the parent line used in the original transformation.

Results revealed up to 56% reduction in fungal colonization in transgenic, gdhA+ expressing lines. HPLC analysis showed that gdhA+ expressing lines had up to 70% less accumulated aflatoxin compared to lines not expressing the gdhA gene.

TABLE 4

| | Presence of gdh | Aflatoxin (ng/g)[a] | Ear rot[b] |
|---|---|---|---|
| LL-3xB73 | Yes | 623[c] | 2.1 |
| DL5xB73 | No | 2506[b] | 4.4 |
| B73 | No | 3342[ab] | 4.8 |
| BDxLL3-2 | Yes | 264[d] | 3.1 |
| BDxLL3-7 | Yes | 347[cd] | 2.23 |
| PIONEER | No | 2205[bc] | 5.1 |
| LL2000 | Yes | 535[c] | 3.2 |
| B73xH99 | No | 3237[b] | 5.3 |
| MP420 | No | 537[c] | 2.4 |
| B73xDL5 | No | 2640[ab] | 4.8 |
| B73xLL3-272 | Yes | 393[c] | 1.2 |
| H99 | No | 6060[a] | 6.2 |
| LL3 | Yes | 508[c] | 2.2 |
| DL5 | No | 3520[ab] | 5.1 |

[a]Means followed by different letters are significantly different at the 0.05 probability level by the least significant ratio test.
[b]Ratings on 1 to 10 scale: 1 = 10%, TO 10 = 100% of inoculated area rotted.
LL-3, LL3-2, LL3-7, LL200, LL3-272 are lines from different transformation events (selfed at least 3 times).
DL5 is a line from corn transformed with an empty vector.
Controls include MP420, Pioneer, B73, H99, DL5.
H99 is the parent line used in the original transformation.

Example 7

Correlating the Resistance of the gdhA+ Plants to Colonization by *A. flavus* and the Accumulation of AFB1 to the Expression Pattern of Lipoxygenase Genes in the Transgenic Plants Real-time PCR was used to assess expression levels of a corn lipoxygenase gene in transgenic corn plants. No significant differences were found in expression levels of the gene in transgenic plants (gdhA+) as compared to unaltered plants.

To assess expression of the corn lipoxygenase gene, embryos of corn kernels from corn lines of interest can be inoculated with *A. flavus* as described in previous examples. Ten days after inoculation, total RNA is extracted from the embryos of the corn kernels. The RNA from each experimental unit (three kernels in a Petri-plate) is pooled. Real-Time PCR is used to assess the expression levels of corn lipoxygenase genes. Primers used in the Real-Time PCR experiment are designed based on the published sequences of lipoxygenase genes identified in corn (GenBank accession numbers: AF465643, and AF329371). Primers specific to the constitutively expressed α-tubulin genes are used as an internal standard (Giedt and Weil, 2000, Plant Journal, 24:815-823). The previously extracted RNA will contain both plant and fungal RNA if the corn kernels harbor any fungal growth. Real-Time PCR is also used to quantify the extent of colonization of the kernels by *A. flavus* by assessing the expression level of a constitutively expressed actin gene from *A. flavus*. Accumulation of AFB1 is assessed by quantifying the expression levels of the gene verA, one of the genes involed in AFB1 biosynthesis. Expression data is analyzed as described by (Tsitsigiannis et al., 2005, Molecular Plant-Microbe Interactions, 18:1081-1089). The expression level of the genes is determined by first normalizing the target RNA to the internal RNA (actin) using the 2(Ct actin)-(Ct target) formula (Livak and Schmittgen, 2001, Methods, 25:402-408; Pfaffl, 2001, Nucleic Acids Research, 29:2002-2007). The same approach is also used to validate expression data in the field. The results reveal differences in the expression patterns of the lipoxygenase genes amongst the different tested corn lines and whether challenging the different corn lines with *A. flavus* affects the expression level of these genes.

Example 8

Resistance to Necrotrophic Root Rotting Fungus

In this example the gdhA gene was shown to provide resistance to root rot and protected root growth in corn and tobacco plants when *Fusarium virguliforme* was present. Root weight was higher in gdhA+ plants than in gdhA− plants (Table 5). Root rot was much less in gdhA+ plants than in gdhA− plants (Table 5). Additionally, the root health depended on the amount of gdhA expression. Metabolites found altered in the roots of gdhA+ plants are believed to cause the observed resistance (Tables 6A-6J).

Methods were as follows: seed of *Zea mays* (Zm) and *Nicotiana tabacum* (Nt), either with or without the gdhA gene were germinated in a sand soil mix for 14 days. The plants were transferred to *F. virguliforme* infested media prepared as follows: *Fusarium virguliforme* strain Monticello 1, maintained on 5× Bilays medium at 19° C., was transferred onto PDA plates at 28° C. for inoculum preparation.

Cornmeal Sand Assay: The cornmeal method of inoculation was used with a few modifications. Two 1 cm×1 cm square pieces of the infested agar was transferred into a 50 ml volume of cornmeal and silica mix (1:1) and moistened with sterile water. This was kept in an incubator for 14 days. At the same time, seeds were sown on steamed sand. After 14 days, the inoculum was mixed with steamed sand/soil (1:1 v/v) in a 1:40 proportion. Pots with 0.5 L of media were filled and 14 day old seedlings were transferred into the filled pots. These were set in water-filled basins with enough water to keep the lower 1-2 inches flooded and the rest of the root zone moist. An equal number of non-inoculated plants were kept under identical conditions. Root infection was rated at day at 28 days after inoculation, using a 1 to 5 scale for describing root rot, with 1 healthy and 5 completely rotted.

TABLE 5

Tobacco and maize plants expressing the gdhA gene are resistant to *Fusarium virguliforme* root rots.

| Genotype | Fv* (

TABLE 6C

Fatty acids in root extracts with altered abundance (percentage change)
in gdhA+ plants compared to gdhA− plants.

Lipids

| Common Name | Systematic Name | Empirical Formula | Degree of saturation | Molecular Mass | Percent Change |
|---|---|---|---|---|---|
| 26) Pelargonic acid | n-Nonanoic acid | C9H18O2 | 9:0 | 158.1380 | 13 |
| 27) Capric acid | n-Decanoic acid | C10H20O2 | 10:0 | 172.1463 | 13 |
| 28) Undecanoic acid | n-Hendecanoic Acid | C11H22O2 | 11:0 | 186.1620 | 21 |
| 29) Lauric acid | Dodecanoic acid | C12H24O2 | 12:0 | 200.1776 | 14 |
| 30) | trans-2-Tridecenoic acid | C13H24O2 | 13:1 | 212.1776 | 50 |
| 31) | Tridecanoic acid | C13H26O2 | 13:0 | 214.1933 | 22 |
| 32) Undecanedioic acid | | C11H20O4 | 11:2 | 216.1362 | 14 |
| 33) Pentadecanoic Acid | n-Pentadecanoic Acid | C15H30O2 | 15:0 | 242.2246 | 6 |
| 34) Palmitoleic Acid | Hexadecenoic acid | C16H30O2 | 16:1 | 254.2246 | 29 |
| 35) Palmitic acid | Hexadecanoic acid | C16H32O2 | 16:0 | 256.2402 | 4 |
| 36) | Tetradecanedioic acid | C14H26O4 | 14:2 | 258.1831 | 13 |
| 37) n-Heptadecanoic Acid | | C17H34O2 | 17:0 | 270.2559 | 19 |
| 38) Oleic acid | 9,12-Octadecanedioic acid | C18H32O2 | 18:1 | 282.2559 | 32 |
| 39) Stearic acid | Octadecenoic acid | C18H34O2 | 18:0 | 284.2715 | 11 |
| 40) | n-Nonadecanoic Acid | C19H38O2 | 19:0 | 298.2872 | 10 |
| 41) DL-12-Hydroxystearic acid | | C18H36O3 | 18:0 | 300.2664 | 196 |
| 42) | Tricosanoic acid | C23H46O2 | 23:0 | 354.3498 | 13 |
| 43) Lignoceric acid | Tetracosanoic acid | C24H48O2 | 24:0 | 368.3654 | 5 |

Fatty acids, fatty acid derivatives and conjugates in root extracts with
altered abundance (percentage change) in gdhA+ plants compared to gdhA− plants.

Lipids
Leaf
Extracts

| Common Name | Systematic Name | Empirical Formula | Molecular Mass | Degree of saturation | % Change |
|---|---|---|---|---|---|
| Pentadecanoic acid | n-Pentadecanoic acid | C15H30O2 | 242.2246 | 15:0 | 23 |
| Palmitoleic Acid | Hexadecenoic acid | C16H30O2 | 254.2246 | 16:1 | 12 |
| Palmitic acid | Hexadecanoic acid | C16H32O2 | 256.2402 | 16:0 | 30 |
| Linoleic acid | 9,12-Octadecanedioic acid | C18H32O2 | 280.2402 | 18:2 | 36 |
| Oleic acid | 9-Octadecenoic acid | C18H34O2 | 282.2559 | 18:1 | 14 |
| Lignoceric acid | Tetracosanoic acid | C24H48O2 | 368.3654 | 24:0 | 15 |
| Ethyl tetracosanoate | | C26H52O2 | 396.3967 | | 30 |

Lipid Derivatives
Root Extracts

| Systematic Name | Empirical Formula | Molecular Mass | Percent Change |
|---|---|---|---|
| 44) Tetradecanoic acid, 7-oxo-, methyl ester | C15H28O | 224.2140 | 43 |
| 45) (9Z)-(13S)-12,13-Epoxyoctadeca-9,11-dienoate | C18H30O3 | 294.2195 | 192 |

TABLE 6C-continued

| | | | | |
|---|---|---|---|---|
| 46) 9-Octadecenoic acid, methyl ester | C19H36O2 | 296.2715 | 23 | |
| 47) Ethyl linoleate | C20H36O2 | 308.2715 | 31 | |
| 48) (9Z,11E,14Z)-(13S)-Hydroperoxyoctadeca-(9,11,14)-trienoate | C18H30O4 | 310.2144 | 238 | 386 |
| 49) Methyl 12-oxo-trans-10-octadecenoate | C19H34O3 | 310.2508 | 25 | |
| 50) Octadecanoic acid, ethenyl ester | C20H38O2 | 310.2872 | 17 | |
| 51) (9Z,11E)-(13S)-13-Hydroperoxyoctadeca-9,11-dienoate | C18H32O4 | 312.2301 | 194 | |
| 52) Octadecanoic acid, 12-oxo-, methyl ester | C19H36O3 | 312.2664 | 14 | |
| 53) Diethyl tetradecanedioate | C18H34O4 | 314.2457 | 19 | |
| 54) Propyl stearate | C21H32O2 | 326.3185 | 18 | |
| 55) 5(S)-hydroperoxy-arachidonate | C20H32O4 | 336.2301 | 714 | 238 |
| 56) Octadecanoic acid, 9,10-epoxy-, allyl ester | C21H38O3 | 338.2821 | 10 | |
| 57) Ethyl tricosanoate | C25H50O2 | 382.3811 | 7 | |
| 58) Ethyl tetracosanate | C26H52O2 | 396.3967 | 8 | |
| 59) 4,4'-Dimethylcholestatrienol | C29H46O | 410.3549 | 16 | |

Lipids

| Common Name | Systematic Name | Empirical Formula | Degree of saturation | Mass | % Change |
|---|---|---|---|---|---|
| Pelargonic acid | n-Nonanoic acid | | 9:0 | 158.1380 | |
| Capric acid | n-Decanoic acid | | 10:0 | 172.1463 | 13 |
| Undecanoic acid | n-Hendecanoic Acid | C11H2O2 | 11:0 | 186.1620 | 13 |
| Lauric acid | Dodecanoic acid | | 12:0 | 200.1776 | 21 |
| | trans-2-Tridecenoic acid | | 13:1 | 212.1776 | 14 |
| | Tridecanoic acid | | 13:0 | 214.1933 | 50 |
| Oleic acid | 9,12-Octadecanedioic acid | C18H32O2 | 18:1 | 282.2559 | 19 |
| Stearic acid | Octadecanoic acid | C18H34O2 | 18:0 | 284.2715 | 32 |
| DL-12-Hydroxystearic acid | | | 18:0 | 300.2664 | 11 |
| | n-Nonadecanoic Acid | | 19:0 | 298.2872 | 196 |
| | Tricosanoic acid | | 23:0 | 354.3498 | 10 |
| Lignoceric acid | Tetracosanoic acid | | 24:0 | 368.3654 | 13 5 |

[a] mass is ±1 ppm, or 0.0002-0.00001 d
[b] % changes are ±2%

TABLE 6D

Compounds of special nitrogen metabolism in root extracts with altered abundance (percentage change) in gdhA+ plants compared to gdhA− plants.

Special Nitrogen Metabolism
Leaf Extracts

| Amines | Empirical Formula | Molecular Mass | Percent Change |
|---|---|---|---|
| N-caffeoylputrescine | C13H18N2O3 | 250.1317 | 196 |
| Alkaloids | | | |
| 8-acetyl quinoline | C11H0NO2 | 187.0633 | 227 |
| Scopoletin | C10H8O4 | 192.0423 | 244 |
| Phenolics | | | |
| 4-hydroxycoumarin | C9H6O3 | 162.0317 | 270 |
| N,N-dimethyl-5-methoxytryptamine | C13H18N2O | 218.1419 | 294 |
| Acetophenone | C8H8O | 120.0575 | 238 |

TABLE 6D-continued

Compounds of special nitrogen metabolism in root extracts with altered abundance (percentage change) in gdhA+ plants compared to gdhA− plants.

Root Extracts

| Class | Empirical Formula | Molecular Mass | Percent Change | | |
|---|---|---|---|---|---|
| Amines | | | | | |
| 66) Epinine | C9H13NO2 | 167.0946 | 222 | | |
| 67) N-Caffeoylputrescine | C13H18N2O3 | 250.1317 | 19 | 26 | 25 |
| Alkaloids | | | | | |
| 68) Coumarin | C9H6O2 | 146.0368 | 10 | | |
| 69) Indole-5,6-quinone | C8H5NO2 | 147.0393 | 40 | | |
| 70) 2-methyl cinnamic acid | C10H20O2 | 162.0681 | 59 | | |
| 71) 3-acetylaminoquinoline | C11H10N2O | 186.0793 | 34 | | |
| 72) 7-Ethoxy-4-methylcoumarin | C12H12O3 | 204.0786 | 36 | | |

TABLE 6D-continued

Compounds of special nitrogen metabolism in root extracts with altered abundance (percentage change) in gdhA+ plants compared to gdhA− plants.

| | | | |
|---|---|---|---|
| 73) 4,6-Dimethyl-8-tert-butylcoumarin | C15H18O2 | 230.1307 | 27 |
| 74) 1-O-Hexyl-2,3,5-trimethylhydroquinone | C15H24O2 | 236.1776 | 179 |
| Phenolics | | | |
| 75) Acetophenone | C8H8O | 120.0575 | 54 |
| 76) alpha-Hydroxyacetophenone | C8H8O2 | 136.0524 | 49 |
| 77) Nicotine | C10H14N2 | 162.1157 | 270 |
| 78) Swainsonine | C8H15N2 | 173.1052 | 500 |
| 79) (S)-6-Hydroxynicotine | C10H14N2O | 178.1106 | 263 |
| Isoprenoid | | | |
| 80) Nopinone | C9H14O | 138.1045 | 20 |

$^a$mass is ±1 ppm, or 0.0002-0.00001 d
$^b$% changes are ±2%

TABLE 6E

Nucleic Acids in Root Extracts with altered abundance (percentage change) in gdhA+ plants compared to gdhA− plants.

Nucleic Acids in Leaf Extracts

| | Empirical formula | Molecular Weight | % Change |
|---|---|---|---|
| 2,3-cyclopentenopyridine | C8H9N | 119.0735 | 278 |
| Dihydro-thymine | C6H5N2O2 | 128.0586 | 227 |

Nucleic Acids in Root Extracts

| | Empirical Formula | Molecular Mass | Percent Change | |
|---|---|---|---|---|
| 84) Dihydro-thymine | C6H5N2O2 | 128.0586 | 238 | 278 |
| 85) Uridine | C9H12N2O6 | 244.0695 | 400 | |

Nucleic Acids in Leaf Extracts

| | Empirical formula | Molecular Weight | % Change |
|---|---|---|---|
| 2,3-cyclopentenopyridine | C8H9N | 137.0437 | 176 |
| Dihydro-thymine | C6H5N2O3 | 146.0288 | 125 |

Nucleic Acids in Root Extracts $^a$: mass is ±1 ppm, or 0.0002-0.00001 d
$^b$: % changes are ±2%

TABLE 6F

TCA cycle intermediates and derivatives root extracts with altered abundance (percentage change) in gdhA+ plants compared to gdhA− plants.

| | Empirical Formula | Molecular Weight | % Change |
|---|---|---|---|
| Sugars and Derivatives in Leaf Extracts | | | |
| Bis-D-fructose 2′,1:2,1′-dianhydride | C12H20O10 | 324.1056 | 208 |
| 3-Deoxy-D-glycero-D-galacto-2-nonulosonic Acid | C9H16O9 | 268.0794 | 159 |
| Sugars and Derivatives in Root Extracts | | | |
| 1,6-Anhydro-beta-D-glucopyranose | | 162.0528 | 263 |
| 2-amino-2-deoxy-D-glucose | | 179.0794 | 276 |
| Sedoheptulose anhydride | | 192.0634 | 909 |

TABLE 6F-continued

TCA cycle intermediates and derivatives root extracts with altered abundance (percentage change) in gdhA+ plants compared to gdhA− plants.

| | | |
|---|---|---|
| 3-Deoxy-D-glycero-D-galacto-2-nonulosonic Acid | 268.0794 | 233 |
| 1,6-Anhydro-beta-D-glucopyranose 2,3,4-Triacetate | 288.0845 | 588 |
| Bis-D-fructose 2′,1:2,1′-dianhydride | 324.1056 | 1250 |

TCA Cycle Intermediates and Derivatives in Leaf Extracts

| | Empirical Formula | Molecular Mass | % Change |
|---|---|---|---|
| Fumaric acid, monoethyl ester | C6H8O4 | 144.0423 | 56 |

TCA Cycle Intermediates and Derivatives in Root Extracts

| | Empirical Formula | Molecular Mass | Percent Change |
|---|---|---|---|
| 87) Fumaric acid | C4H4O4 | 116.0110 | 270 |
| 88) DL-malic acid | C4H6O5 | 134.0215 | 270 |
| 89) Citric acid | C6H8O7 | 192.0270 | 385 |
| 90) Fumaric acid monoethyl ester | C6H8O4 | 144.0423 | 345 |

$^a$: mass is ±1 ppm, or 0.0002-0.00001 d
$^b$: % changes are ±2%

TABLE 6G

Metabolites involved in stress tolerance in root extracts with altered abundance (percentage change) in gdhA+ plants compared to gdhA− plants.

Nucleic Acids in Leaf Extracts

| | Empirical formula | Molecular Weight | % Change |
|---|---|---|---|
| 2,3-cyclopentenopyridine | C8H9N | 119.0735 | 278 |
| Dihydro-thymine | C6H5N2O2 | 128.0586 | 227 |

Nucleic Acids in Root Extracts

| | Empirical formula | Molecular Weight | % Change | |
|---|---|---|---|---|
| Dihydro-thymine | | 128.0586 | 238 | 278 |
| Uridine | | 244.0695 | 400 | |

Stress and Proline Metabolism in Leaf Extracts

| | Empirical Formula | Molecular Mass | Percent Change |
|---|---|---|---|
| 91) 3-hydroxy-1-pyrroline-delta-carboxylate | C5H7NO3 | 129.0426 | 133 |

Stress and Proline Metabolism in Root Extracts

| | Empirical formula | Molecular Weight | % Change |
|---|---|---|---|
| 3-hydroxy-1-pyrroline-gamma-carboxylate | | 129.0426 | 244 |
| delta1-Pyrroline 2-carboxylate | | 113.0477 | 217 |

Nucleic Acids in Leaf Extracts

| | Empirical formula | Molecular Weight | % Change |
|---|---|---|---|
| 2,3-cyclopentenopyridine | C8H9N | 119.0735 | 278 |
| Dihydro-thymine | C6H5N2O2 | 128.0586 | 227 |

TABLE 6G-continued

Metabolites involved in stress tolerance in root extracts with altered abundance (percentage change) in gdhA+ plants compared to gdhA− plants.

Nucleic Acids in Root Extracts

| | Empirical formula | Molecular Weight | % Change | |
|---|---|---|---|---|
| Dihydro-thymine | | 128.0586 | 238 | 278 |
| Uridine | | 244.0695 | 400 | |

Stress and Proline Metabolism in Leaf Extracts

| | Empirical formula | Molecular Weight | % Change |
|---|---|---|---|
| 3-hydroxy-1-pyrroline-delta-carboxylate | C5H7NO3 | 129.0426 | 133 |

Stress and Proline Metabolism in Root Extracts

| | Empirical Formula | Molecular Mass | Percent Change |
|---|---|---|---|
| 92) delta1-Pyrroline 2-carboxylate | C5H7NO2 | 113.0477 | 217 |
| 93) 3-hydroxy-1-pyrroline-gamma-carboxylate | C5H7NO3 | 129.0426 | 244 |

[a]: mass is ±1 ppm, or 0.0002-0.00001 d
[b]: % changes are ±2%

TABLE 6H

Miscellaneous metabolites in root extracts with altered abundance (percentage change) in gdhA+ plants compared to gdhA− plants—Part 1
Miscellaneous Compounds Root Extracts

| | Empirical Formula | Molecular Weight | % Change | |
|---|---|---|---|---|
| N-Nitrosopyrrolidine | | 100.0637 | 714 | |
| 3-Methoxy-1,2-propanediol | | 106.0630 | 40 | |
| cis-2-hexenoic acid amide* | | 113.0841 | 26 | |
| 7-Oxabicyclo[2.2.1]hept-5-ene-2,3-dione | | 124.0160 | 41 | |
| 2-methoxy-3-methyl-pyrazine | | 124.0637 | 51 | |
| Phthalic anhydride | | 148.0160 | 24 | |
| Gamma-Nonanolactone | | 156.1150 | 43 | |
| 1,5-diaatricyclo[4.2.2.2(2,5)]dodecane | | 166.0994 | 625 | |
| 2-Decenoic Acid | | 170.1307 | 56 | |
| 2,2,6,6-tetramethyl-N-nitrosopiperidine | | 170.1419 | 29 | |
| 1-Acetyl-4-piperidinecarboxylic acid | | 171.0895 | 270 | |
| Decanamide[‡] | | 171.1623 | 435 | |
| Sulfuric acid dipropyl ester | | 182.0613 | 56 | |
| o,o'-Iminostilbene[†] | | 193.0892 | 13 | 417 |
| Cyclohexanepropionic acid, 4-oxo-, ethyl ester | | 198.1256 | 25 | |
| Cyclooctyl-1,1-dimethylurea | | 198.1732 | 24 | |
| Sebacic Acid | | 202.1205 | 16 | |
| cis-2,6-Di-tert-butylcyclohexanone | | 210.1984 | 35 | |
| 6-[2-(5-nitrofuranyl)ethenyl]-2-pyridinemethanol | | 224.0797 | 213 | |
| 5-allyl-5-butylbarbituric acid | | 224.1161 | 22 | |
| Isothiocyanic acid 1,4-cyclohexylene-dimethylene ester[†] | | 226.0598 | 31 | |
| Tetradecanamide | | 227.2249 | 2 | |

TABLE 6H-continued

Miscellaneous metabolites in root extracts with altered abundance (percentage change) in gdhA+ plants compared to gdhA− plants—Part 1
Miscellaneous Compounds Root Extracts

| | Empirical Formula | Molecular Weight | % Change | |
|---|---|---|---|---|
| Cedrol methyl ether* | | 236.2140 | 21 | |
| Cyclohexadecanone | | 238.2297 | 18 | |
| 1,3-Di-o-tolylguanidine | | 239.1422 | 400 | |
| Menthyl acetoacetate* | | 240.1725 | 13 | |
| Methocarbamol* | | 241.0950 | 244 | |
| N-[2,6-bis(isopropyl)phenyl]-2-imidazolidineimine | | 245.1892 | 345 | |
| (−)-Ptilocaulin[‡] | | 247.2048 | 294 | |
| 1-Lauryl-2-pyrrolidone | | 253.2406 | 29 | 769 |
| Hexadecanamide | | 255.2562 | 12 | 556 |
| Dodecylmalonic acid | | 272.1988 | 46 | |
| 4-amino-N-(6-methoxy-4-pyrimidyl)-benzenesulfonamide | | 280.0630 | 20 | |
| Rocastine | | 281.1198 | 276 | |
| Palmoxiric acid | | 284.2351 | 35 | |
| Propionic acid, 3-dodecyloxy-2-ethoxy-, methyl ester | | 316.2614 | 556 | |
| Benzenesulfonic acid dodecylester | | 326.1916 | 63 | |
| Di(2-ethylhexyl) itaconate | | 354.2770 | 40 | |
| 2,2'-ethyledene bis(4,6-di-t-butyl | | 438.3498 | 12 | |

*Cigarette component
[†]Pesticide or Herbicide
[‡]Drug

TABLE 6I

Miscellaneous metabolites in root extracts with altered abundance (percentage change) gdhA+ plants compared to gdhA− plants. - Part 1

| Empirical Formul | Degree of Saturation | Molecular Mass | Percent Change |
|---|---|---|---|
| | | 300.2664 | 196 |
| | 9:0 | 158.1380 | 13 |
| | 10:0 | 172.1463 | 13 |
| C11H2O2 | 11:0 | 186.1620 | 21 |
| | 12:0 | 200.1776 | 14 |
| | 13:1 | 212.1776 | 50 |
| | 13:0 | 214.1933 | 22 |
| | | 216.1362 | 14 |
| | 15:0 | 242.2246 | 6 |
| | 16:1 | 254.2246 | 29 |
| | 16:0 | 256.2402 | 4 |
| | 14:0 | 258.1831 | 13 |
| | 17:0 | 270.2559 | 19 |
| 1 | 18:1 | 282.2559 | 32 |
| | 18:0 | 284.2715 | 11 |
| | 19:0 | 298.2872 | 10 |
| | 23:0 | 354.3498 | 13 |
| | 24:0 | 368.3654 | 5 |

TABLE 6Ia

| | Compound | C | H | N | O | P | S | Molecular Mass Neutral | Mode+ | Mode− |
|---|---|---|---|---|---|---|---|---|---|---|
| | Glu | 5 | 9 | 1 | 4 | | | 147.0532 | 148.0604 | 146.0459 |
| | Gln | 5 | 10 | 2 | 3 | | | 146.0691 | 147.0764 | 145.0619 |
| | His | 6 | 9 | 3 | 2 | | | 155.0695 | 156.0768 | 154.0622 |
| | Pro | 5 | 9 | 1 | 2 | | | 115.0633 | 116.0706 | 114.0561 |
| | Arg | 6 | 15 | 4 | 2 | | | 175.1195 | 176.1268 | 174.1122 |
| | Asp | 4 | 7 | 1 | 4 | | | 133.0375 | 134.0448 | 132.0302 |
| | Asn | 4 | 8 | 2 | 3 | | | 132.0535 | 133.0608 | 131.0462 |
| | Thr | 5 | 11 | 1 | 3 | | | 133.0739 | 134.0812 | 132.0666 |
| | Iso | 6 | 13 | 1 | 2 | | | 131.0946 | 132.1019 | 130.0874 |
| | Met | 5 | 11 | 1 | 2 | | 1 | 149.0511 | 150.0583 | 148.0438 |
| | Lys | 6 | 14 | 2 | 2 | | | 146.1055 | 147.1128 | 145.0983 |
| | Ser | 3 | 7 | 1 | 3 | | | 105.0426 | 106.0499 | 104.0353 |
| | Gly | 2 | 5 | 1 | 2 | | | 75.0320 | 76.0393 | 74.0248 |
| | Cys | 3 | 7 | 1 | 2 | | 1 | 121.0198 | 122.0270 | 120.0125 |
| | Trp | 11 | 12 | 2 | 2 | | | 204.0899 | 205.0972 | 203.0826 |
| | Tyr | 9 | 11 | 1 | 3 | | | 181.0739 | 182.0812 | 180.0666 |
| | Phe | 9 | 11 | 1 | 2 | | | 165.0790 | 166.0863 | 164.0717 |
| | Ala | 3 | 7 | 1 | 2 | | | 89.0477 | 90.0550 | 88.0404 |
| | Leu | 6 | 13 | 1 | 2 | | | 131.0946 | 132.1019 | 130.0874 |
| | Val | 5 | 11 | 1 | 2 | | | 117.0790 | 118.0863 | 116.0717 |
| Voet2 | Glucose | 6 | 12 | | 6 | | | 180.0634 | 181.0707 | 179.0561 |
| p446 | Glu-6-P | 6 | 11 | | 9 | 1 | | 258.0141 | 259.0213 | 257.0068 |
| | Fru-6-P | 6 | 11 | | 9 | 1 | | 258.0141 | 259.0213 | 257.0068 |
| | FBP | 6 | 10 | | 12 | 2 | | 335.9648 | 336.9720 | 334.9575 |
| | GAP/DHAP | 3 | 5 | | 6 | 1 | | 167.9824 | 168.9897 | 166.9751 |
| | 1,3 BPG | 3 | 4 | | 10 | 2 | | 261.9280 | 262.9353 | 260.9207 |
| | 3PG | 3 | 4 | | 7 | 1 | | 182.9695 | 183.9767 | 181.9622 |
| | 2PG | 3 | 4 | | 6 | 1 | | 166.9746 | 167.9818 | 165.9673 |
| | PEP | 3 | 2 | | 6 | 1 | | 164.9589 | 165.9662 | 163.9516 |
| | Pyruvate | 3 | 3 | | 3 | | | 87.0082 | 88.0155 | 86.0009 |
| p381 | Erythrose-4-P | 4 | 7 | | 7 | 1 | | 197.9929 | 199.0002 | 196.9857 |
| | DAHP | 7 | 9 | | 7 | 1 | | 236.0086 | 237.0159 | 235.0013 |
| | 3-dehydroquinate | 7 | 6 | | 6 | | | 186.0164 | 187.0237 | 185.0092 |
| | 3-dehydroshikimate | 7 | 6 | | 5 | | | 170.0215 | 171.0288 | 169.0142 |
| | Shikimate | 7 | 9 | | 5 | | | 173.0450 | 174.0523 | 172.0377 |
| | Shikimate-3-P | 7 | 8 | | 5 | 1 | | 203.0109 | 204.0182 | 202.0037 |
| | EPSP | 10 | 9 | | 7 | 1 | | 272.0086 | 273.0159 | 271.0013 |
| | Chorismate | 10 | 8 | | 6 | | | 224.0321 | 225.0394 | 223.0248 |
| p384 | Prephenate | 10 | 8 | | 6 | | | 224.0321 | 225.0394 | 223.0248 |
| | Arogenate | 10 | 12 | 1 | 5 | | | 226.0715 | 227.0788 | 225.0643 |
| p387 | Anthranilate | 7 | 7 | 1 | 2 | | | 137.0477 | 138.0550 | 136.0404 |
| | 5-phosphoribosyl-anthranilate | 12 | 13 | | 6 | 1 | | 284.0450 | 285.0523 | 283.0377 |
| | 1-(o-carboxy-phenyl amino)-1-deoxy ribulose-5-P | 12 | 13 | | 6 | 1 | | 284.0450 | 285.0523 | 283.0377 |
| | Indole-3-glycerol-P | 11 | 14 | 1 | 3 | 1 | | 239.0711 | 240.0784 | 238.0639 |
| | Indole | 8 | 7 | 1 | | | | 117.0578 | 118.0651 | 116.0506 |
| p398 | Asp-4-P | 4 | 6 | 1 | 6 | 1 | | 194.9933 | 196.0006 | 193.9860 |
| | Asp-4-semialdehyde | 4 | 7 | 1 | 3 | | | 117.0426 | 118.0499 | 116.0353 |
| | Homoserine | 4 | 9 | 1 | 3 | | | 119.0582 | 120.0655 | 118.0510 |
| | Homoserine-4-P | 4 | 8 | 1 | 3 | 1 | | 149.0242 | 150.0315 | 148.0169 |
| p399 | 2,3-dihydrodipiconilate | 7 | 5 | 1 | 4 | | | 167.0219 | 168.0291 | 166.0146 |
| | Diaminopimelate | 7 | 14 | 2 | 4 | | | 190.0954 | 191.1026 | 189.0881 |
| | Cystathionine | 7 | 14 | 2 | 4 | | 1 | 222.0674 | 223.0747 | 221.0602 |
| | Homocysteine | 4 | 9 | 1 | 2 | | 1 | 135.0354 | 136.0427 | 134.0281 |
| p403 | alpha-ketoglutarate | 5 | 4 | | 5 | | | 144.0059 | 145.0132 | 142.9986 |
| | Saccharopine | 11 | 17 | 1 | 6 | | | 259.1056 | 260.1129 | 258.0983 |
| | alpha-aminoadipic delta-semialdehyde | 6 | 11 | 1 | 2 | | | 129.0790 | 130.0863 | 128.0717 |
| p405 | 2-ketobutyrate | 4 | 5 | | 3 | | | 101.0239 | 102.0311 | 100.0166 |
| | 2-acetohydroxybutyrate or 2-ketoisocaproate or 2-keto-3-methylvalerate | 6 | 9 | | 3 | | | 129.0552 | 130.0624 | 128.0479 |
| | 2-acetolactate | 5 | 7 | | 4 | | | 131.0344 | 132.0417 | 130.0272 |
| | 2,3-dihydroxy-3-methylvalerate | 6 | 10 | | 4 | | | 146.0579 | 147.0652 | 145.0506 |
| | 2,3-dihydroxyiso-valerate | 5 | 9 | | 4 | | | 133.0501 | 134.0574 | 132.0428 |
| | 2-ketoisovalerate | 5 | 7 | | 3 | | | 115.0395 | 116.0468 | 114.0322 |
| | 3-carboxy-3-hydroxy-isocaproate OR 3-carboxy-2-hydroxy-isocaproate | 7 | 10 | | 5 | | | 174.0528 | 175.0601 | 173.0455 |
| p408 | L-glutamyl-gamma-P | 5 | 8 | 1 | 4 | 1 | | 177.0191 | 178.0264 | 176.0118 |
| | Glutamic-gamma-semialdehyde | 5 | 9 | 1 | 3 | | | 131.0582 | 132.0655 | 130.0510 |

TABLE 6Ia-continued

| | Compound | C | H | N | O | P | S | Molecular Mass Neutral | Mode+ | Mode− |
|---|---|---|---|---|---|---|---|---|---|---|
| | delta1-pyrroline-5-carboxylate (P5C) OR delta1-pyrroline-2-carboxylate (P2C) | 5 | 7 | 1 | 2 | | | 113.0477 | 114.0550 | 112.0404 |
| | L-ornithine | 5 | 12 | 2 | 2 | | | 132.0899 | 133.0972 | 131.0826 |
| | alpha-keto-delta-aminovalerate | 5 | 9 | 1 | 3 | | | 131.0582 | 132.0655 | 130.0510 |
| p1209 | Cinnamic acid or p-coumaraldehyde | 9 | 8 | | 2 | | | 148.0524 | 149.0597 | 147.0452 |
| | p-coumaric acid | 9 | 8 | | 3 | | | 164.0473 | 165.0546 | 163.0401 |
| | p-coumaryl alcohol | 9 | 9 | | 2 | | | 149.0603 | 150.0675 | 148.0530 |
| | coumarins or caffeic acid | 9 | 8 | | 4 | | | 180.0423 | 181.0495 | 179.0350 |
| | ferulic acid | 10 | 1 | | 4 | | | 184.9875 | 185.9948 | 183.9802 |
| | coniferaldehyde | 10 | 10 | | 3 | | | 178.0630 | 179.0703 | 177.0557 |
| | coniferyl alcohol | 10 | 11 | | 3 | | | 179.0708 | 180.0781 | 178.0635 |
| | 5-hydroxyferulic acid | 10 | 11 | | 5 | | | 211.0607 | 212.0679 | 210.0534 |
| | 5-hydroxy coniferaldehyde | 9 | 10 | | 4 | | | 182.0579 | 183.0652 | 181.0506 |
| | sinapic acid | 11 | 13 | | 5 | | | 225.0763 | 226.0836 | 224.0690 |
| | sinapaldehyde | 11 | 12 | | 4 | | | 208.0736 | 209.0808 | 207.0663 |
| | sinapyl alcohol | 11 | 13 | | 4 | | | 209.0814 | 210.0887 | 208.0741 |
| p1304 | kaempferol | 15 | 10 | | 6 | | | 286.0477 | 287.0550 | 285.0405 |
| Dey Book | | | | | | | | | | |
| p118-121 | glucolactonone-6-P | 6 | 9 | | 9 | 1 | | 255.9984 | 257.0057 | 254.9911 |
| | glucolactonate-6-P | 6 | 10 | | 10 | 1 | | 273.0012 | 274.0084 | 271.9939 |
| | ribulose-5-P or ribose-5-P or xylulose-5-P | 5 | 9 | | 8 | 1 | | 228.0035 | 229.0108 | 226.9962 |
| | sedoheptulose-7-P | 7 | 13 | | 10 | 1 | | 288.0246 | 289.0319 | 287.0174 |
| p123 | acetyl coenzyme A | 21 | 32 | 7 | 16 | 3 | 1 | 763.0839 | 764.0912 | 762.0766 |
| | oxaloacetate | 4 | 4 | | 5 | | | 132.0059 | 133.0132 | 130.9986 |
| | citrate or isocitrate | 6 | 8 | | 7 | | | 192.0270 | 193.0343 | 191.0197 |
| | oxalosuccinate intermediate | 6 | 6 | | 7 | | | 190.0114 | 191.0186 | 189.0041 |
| | alpha-ketoglutarate | 5 | 6 | | 5 | | | 146.0215 | 147.0288 | 145.0142 |
| | alpha-hydroxyl-gamma-carboxypropyl intermediate | 4 | 7 | | 3 | | | 103.0395 | 104.0468 | 102.0322 |
| | succinyl-CoA | 25 | 37 | 7 | 19 | 3 | 1 | 864.1078 | 865.1151 | 863.1005 |
| | succinate | 4 | 6 | | 4 | | | 118.0266 | 119.0339 | 117.0193 |
| | fumarate | 4 | 4 | | 4 | | | 116.0110 | 117.0182 | 115.0037 |
| | malate | 4 | 6 | | 5 | | | 134.0215 | 135.0288 | 133.0142 |
| p144 | sucrose | 12 | 22 | | 11 | | | 342.1162 | 343.1235 | 341.1089 |
| | citrulline | 6 | 13 | 3 | 3 | | | 175.0957 | 176.1030 | 174.0884 |
| | trigonelline | 6 | 8 | | 2 | | | 112.0524 | 113.0597 | 111.0452 |
| NC | trehalose | 12 | 21 | | 11 | | | 319.1981 | 320.2054 | 318.1909 |
| NC | dimethylsulfoniopropionate | 5 | 11 | | 2 | | 1 | 135.0480 | 136.0553 | 134.0407 |
| NC | glycerol | 3 | 8 | | 3 | | | 92.0473 | 93.0546 | 91.0401 |
| NC | sorbitol or mannitol | 6 | 14 | | 6 | | | 182.0790 | 183.0863 | 181.0718 |
| NC | choline-O-sulphate | 5 | 14 | 1 | 4 | | 1 | 184.0644 | 185.0716 | 183.0571 |
| NC | beta alanine betaine | 6 | 14 | 1 | 2 | | | 132.1025 | 133.1097 | 131.0952 |
| NC | glycinebetaine | 5 | 13 | 1 | 2 | | | 119.0946 | 120.1019 | 118.0874 |
| NC | prolinebetaine | 7 | 13 | 1 | 2 | | | 143.0946 | 144.1019 | 142.0874 |
| NC | N-methyl-proline | 6 | 11 | 1 | 2 | | | 129.0790 | 130.0863 | 128.0717 |
| NC | hydroxyproline | 5 | 9 | 1 | 3 | | | 131.0582 | 132.0655 | 130.0510 |
| NC | hydroxyprolinebetaine | 7 | 13 | 1 | 3 | | | 159.0895 | 160.0968 | 158.0823 |
| Changed? | Non-protein amino acids | | | | | | | | | |
| | beta alanine | 3 | 7 | 1 | 2 | | | 89.0477 | 90.0550 | 88.0404 |
| | 4-amino-butyrate (GABA) | 4 | 9 | 1 | 2 | | | 103.0633 | 104.0706 | 102.0561 |
| | beta cyanoalanine | 4 | 6 | 1 | 2 | | | 100.0399 | 101.0471 | 99.0326 |
| | 2-aminobutyric acid OR 2-aminoisobutyric acid OR 3-aminoisobutyric acid | 4 | 9 | 1 | 2 | | | 103.0633 | 104.0706 | 102.0561 |
| changed but identified as proline | 2-methylene-4-amino-butyric acid OR 3-methylene-4-amino-butyric acid | 5 | 9 | 1 | 2 | | | 115.0633 | 116.0706 | 114.0561 |
| | 5-aminolevulinic acid | 5 | 9 | 1 | 3 | | | 131.0582 | 132.0655 | 130.0510 |
| | 2-amino-4-methyl hexanoic acid (homoisoleucine) | 7 | 15 | 1 | 2 | | | 145.1103 | 146.1176 | 144.1030 |

TABLE 6Ia-continued

|  | Compound | C | H | N | O | P | S | Molecular Mass Neutral | Mode+ | Mode− |
|---|---|---|---|---|---|---|---|---|---|---|
|  | 2-amino-4-methyl hex-4-enoic acid | 7 | 13 | 1 | 2 |  |  | 143.0946 | 144.1019 | 142.0874 |
|  | 2-amino-4-methylhex-5-ynoic-acid | 7 | 11 | 1 | 2 |  |  | 141.0790 | 142.0863 | 140.0717 |
|  | 2-amino-3-methylene-pentanoic acid | 6 | 11 | 1 | 2 |  |  | 129.0790 | 130.0863 | 128.0717 |
|  | 2-amino-3-methylene-4-pentanoic acid | 6 | 9 | 1 | 2 |  |  | 127.0633 | 128.0706 | 126.0561 |
| 1st page | 2-aminoadipic acid | 6 | 11 | 1 | 4 |  |  | 161.0688 | 162.0761 | 160.0615 |
|  | 4-ethylideneglutamic acid | 7 | 11 | 1 | 4 |  |  | 173.0688 | 174.0761 | 172.0615 |
|  | 3-aminoglutaric acid | 5 | 9 | 1 | 4 |  |  | 147.0532 | 148.0604 | 146.0459 |
|  | 2-aminopimelic acid | 7 | 13 | 1 | 4 |  |  | 175.0845 | 176.0917 | 174.0772 |
|  | N4-ethylasparagine | 6 | 12 | 1 | 3 |  |  | 146.0817 | 147.0890 | 145.0744 |
| Glutamine! | N4-methylasparagine | 5 | 10 | 2 | 3 |  |  | 146.0691 | 147.0764 | 145.0619 |
|  | erythro-4-methyl glutamic acid | 6 | 11 | 1 | 4 |  |  | 161.0688 | 162.0761 | 160.0615 |
|  | 4-methyleneglutamic acid | 6 | 9 | 1 | 4 |  |  | 159.0532 | 160.0604 | 158.0459 |
|  | 4-methyleneglutamine | 6 | 10 | 2 | 3 |  |  | 158.0691 | 159.0764 | 157.0619 |
|  | N5-ethylglutamine (Theanine) | 7 | 14 | 2 | 3 |  |  | 174.1004 | 175.1077 | 173.0932 |
|  | N5-isopropylglutamine | 8 | 16 | 2 | 3 |  |  | 188.1161 | 189.1234 | 187.1088 |
|  | 2-amino-4-(aminoxy)-butyric acid (canaline) | 4 | 10 | 2 | 3 |  |  | 134.0691 | 135.0764 | 133.0619 |
|  | 2,4-diaminobutyrate | 4 | 10 | 2 | 2 |  |  | 118.0742 | 119.0815 | 117.0670 |
|  | N4-acetyl-2,4-diamino butyrate | 6 | 12 | 2 | 3 |  |  | 160.0848 | 161.0921 | 159.0775 |
| 2nd page | N4-lactyl-2,4-diamino butyrate | 7 | 13 | 2 | 4 |  |  | 189.0875 | 190.0948 | 188.0803 |
|  | N4-oxacyl-2,4-diamino butyrate | 6 | 10 | 2 | 5 |  |  | 190.0590 | 191.0662 | 189.0517 |
|  | 2,3-diaminopropionic acid | 3 | 8 | 2 | 2 |  |  | 104.0586 | 105.0659 | 103.0513 |
| Glutamine! | N3-acetyl-2,3-diamino propionic acid | 5 | 10 | 2 | 3 |  |  | 146.0691 | 147.0764 | 145.0619 |
|  | N3-methyl-2,3-diamino propionic acid | 4 | 10 | 2 | 2 |  |  | 118.0742 | 119.0815 | 117.0670 |
|  | N3-oxalyl-2,3-diamino propionic acid | 5 | 8 | 2 | 5 |  |  | 176.0433 | 177.0506 | 175.0360 |
|  | N6-acetyllysine | 8 | 16 | 2 | 3 |  |  | 188.1161 | 189.1234 | 187.1088 |
|  | N6-methyllysine | 11 | 16 | 2 | 2 |  |  | 208.1212 | 209.1285 | 207.1139 |
|  | N6-trimethyllysine (laminine) | 9 | 21 | 2 | 2 |  |  | 189.1603 | 190.1676 | 188.1530 |
| Leaf APCI− | ornithine | 5 | 12 | 2 | 2 |  |  | 132.0899 | 133.0972 | 131.0826 |
|  | N5-acetylornithine | 7 | 14 | 2 | 3 |  |  | 174.1004 | 175.1077 | 173.0932 |
|  | saccharopine | 11 | 20 | 2 | 6 |  |  | 276.1321 | 277.1394 | 275.1249 |
|  | 2,6-diaminopimelic acid | 7 | 14 | 2 | 4 |  |  | 190.0954 | 191.1026 | 189.0881 |
|  | N4-(2-hydroxyethyl)-asparagine | 6 | 12 | 2 | 4 |  |  | 176.0797 | 177.0870 | 175.0724 |
|  | erythro-3-hydroxy-aspartic acid | 4 | 7 | 1 | 5 |  |  | 149.0324 | 150.0397 | 148.0251 |
| 3rd page | 4-hydroxyarginine | 6 | 14 | 4 | 3 |  |  | 190.1066 | 191.1139 | 189.0993 |
|  | 4-hydroxycitrulline | 6 | 13 | 3 | 4 |  |  | 191.0906 | 192.0979 | 190.0833 |
|  | threo-4-hydroxyglutamic acid | 5 | 9 | 1 | 5 |  |  | 163.0481 | 164.0554 | 162.0408 |
|  | 3,4-dihydroxyglutamic acid | 5 | 9 | 1 | 6 |  |  | 179.0430 | 180.0503 | 178.0357 |
|  | 3-hydroxy-4-methyl-glutamic acid | 6 | 11 | 1 | 5 |  |  | 177.0637 | 178.0710 | 176.0564 |
|  | 3-hydroxy-4-methylene-glutamic acid | 6 | 10 | 1 | 5 |  |  | 176.0559 | 177.0632 | 175.0486 |
|  | 4-hydroxy-4-methyl-glutamic acid | 6 | 11 | 1 | 4 |  |  | 161.0688 | 162.0761 | 160.0615 |
|  | 4-hydroxyglutamine | 5 | 10 | 2 | 4 |  |  | 162.0641 | 163.0713 | 161.0568 |
|  | N5-(2-hydroxyethyl)-glutamine | 7 | 14 | 2 | 5 |  |  | 206.0903 | 207.0975 | 205.0830 |
|  | 5-hydroxynorleucine OR threo-3-hydroxyleucine OR 5-hydroxyleucine OR 4-hydroxy-isoleucine | 6 | 13 | 1 | 3 |  |  | 147.0895 | 148.0968 | 146.0823 |
| Root APCI+ | homoserine | 4 | 9 | 1 | 3 |  |  | 119.0582 | 120.0655 | 118.0510 |
|  | O-acetyl-homoserine | 6 | 11 | 1 | 4 |  |  | 161.0688 | 162.0761 | 160.0615 |
|  | O-oxalyl-homoserine | 6 | 9 | 1 | 6 |  |  | 191.0430 | 192.0503 | 190.0357 |
| 4th page | O-phosphohomoserine | 4 | 10 | 1 | 6 | 1 |  | 199.0246 | 200.0319 | 198.0173 |
|  | S-hydroxymethylhomocysteine | 5 | 11 | 1 | 3 |  |  | 133.0739 | 134.0812 | 132.0666 |
|  | 2-hydroxylysine OR 4-hydroxylysine OR 5-hydroxylysine | 6 | 14 | 2 | 3 |  |  | 162.1004 | 163.1077 | 161.0932 |

TABLE 6Ia-continued

|   | Compound | C | H | N | O | P | S | Molecular Mass Neutral | Mode+ | Mode− |
|---|---|---|---|---|---|---|---|---|---|---|
|   | N6-acetyl-5-hydroxylysine | 8 | 16 | 2 | 4 |   |   | 204.1110 | 205.1183 | 203.1037 |
|   | N6-trimethyl-5-hydroxylysine | 9 | 21 | 2 | 3 |   |   | 205.1552 | 206.1625 | 204.1479 |
|   | 4-hydroxyornithine | 5 | 12 | 2 | 3 |   |   | 148.0848 | 149.0921 | 147.0775 |
|   | mimosine | 11 | 10 | 2 | 4 |   |   | 234.0641 | 235.0713 | 233.0568 |
|   | 4-hydroxynorvaline OR 5-hydroxynorvaline | 5 | 11 | 1 | 3 |   |   | 133.0739 | 134.0812 | 132.0666 |
|   | 2-amino-4,5-dihydroxy-pentanoic acid | 7 | 11 | 1 | 4 |   |   | 173.0688 | 174.0761 | 172.0615 |
| R APCI+ | 2-amino-4-hydroxy-pimelic acid | 7 | 13 | 1 | 5 |   |   | 191.0794 | 192.0867 | 190.0721 |
| 5th page | 4-hydroxyvaline | 5 | 11 | 1 | 3 |   |   | 133.0739 | 134.0812 | 132.0666 |
|   | O-acetyl-serine | 5 | 9 | 1 | 4 |   |   | 147.0532 | 148.0604 | 146.0459 |
|   | O-phosphoserine | 3 | 8 | 1 | 6 | 1 |   | 185.0089 | 186.0162 | 184.0017 |
|   | pipecolic acid | 6 | 11 | 1 | 2 |   |   | 129.0790 | 130.0863 | 128.0717 |
|   | 3-hydroxy-pipecolic acid OR cis OR trans-4-hydroxy-pipecolic acid OR trans-5-hydroxy-pipecolic acid | 6 | 11 | 1 | 3 |   |   | 145.0739 | 146.0812 | 144.0666 |
|   | 5-hydroxy-6-methyl-pipecolic acid | 7 | 13 | 1 | 3 |   |   | 159.0895 | 160.0968 | 158.0823 |
|   | 4,5-dihydroxy-pipecolic acid | 5 | 11 | 1 | 4 |   |   | 149.0688 | 150.0761 | 148.0615 |
|   | 4,5-dehydropipecolic acid | 6 | 9 | 2 | 2 |   |   |   |   |   |
|   | trans-3-hydroxyproline OR trans-4-hydroxyproline | 5 | 9 | 1 | 3 |   |   | 131.0582 | 132.0655 | 130.0510 |
| 6th page | trans-4-hydroxy-methylproline | 6 | 11 | 1 | 3 |   |   | 145.0739 | 146.0812 | 144.0666 |
|   | azetine-2-carboxylic acid | 4 | 7 | 1 | 2 |   |   | 101.0477 | 102.0550 | 100.0404 |
|   | N-(3-amino-3-carboxypropyl)-azetine-2-carboxylic acid | 8 | 14 | 2 | 4 |   |   | 202.0954 | 203.1026 | 201.0881 |
|   | 3-amino-3-carboxypyrrolidine | 5 | 10 | 2 | 2 |   |   | 130.0742 | 131.0815 | 129.0670 |
|   | 2-(cyclopent-2'-enyl)glycine | 7 | 11 | 1 | 2 |   |   | 141.0790 | 142.0863 | 140.0717 |
|   | 5-hydroxytryptophan | 11 | 12 | 2 | 3 |   |   | 220.0848 | 221.0921 | 219.0775 |
|   | 2-amino-3-ureido-propionic acid (albizziine) | 4 | 9 | 3 | 3 |   |   | 147.0644 | 148.0717 | 146.0571 |
|   | arginosuccinic acid | 10 | 18 | 4 | 6 |   |   | 290.1226 | 291.1299 | 289.1154 |
|   | canavanino succinic acid | 9 | 16 | 4 | 7 |   |   | 292.1019 | 293.1092 | 291.0946 |
| checked | citrulline | 6 | 13 | 3 | 3 |   |   | 175.0957 | 176.1030 | 174.0884 |
|   | canavanine | 5 | 12 | 4 | 3 |   |   | 176.0909 | 177.0982 | 175.0837 |
|   | homoarginine | 7 | 16 | 4 | 2 |   |   | 188.1273 | 189.1346 | 187.1201 |
|   | homocitrulline | 7 | 15 | 3 | 3 |   |   | 189.1113 | 190.1186 | 188.1041 |
| 7th page | indospicine | 7 | 15 | 3 | 2 |   |   | 173.1164 | 174.1237 | 172.1092 |
|   | O-ureidohomoserine | 5 | 11 | 3 | 4 |   |   | 177.0750 | 178.0822 | 176.0677 |
|   | 6-hydroxykynurenine | 10 | 12 | 2 | 4 |   |   | 224.0797 | 225.0870 | 223.0724 |
|   | 3-(aminophenyl)alanine | 9 | 12 | 2 | 2 |   |   | 180.0899 | 181.0972 | 179.0826 |
|   | 3-(3-aminophenyl) alanine | 10 | 14 | 2 | 2 |   |   | 194.1055 | 195.1128 | 193.0983 |
|   | 3-(3-carboxyphenyl) alanine | 10 | 11 | 1 | 4 |   |   | 209.0688 | 210.0761 | 208.0615 |
|   | 3-carboxytyrosine | 10 | 11 | 1 | 5 |   |   | 225.0637 | 226.0710 | 224.0564 |
|   | 3-(3-hydroxymethylphenyl)-alanine | 10 | 13 | 1 | 3 |   |   | 195.0895 | 196.0968 | 194.0823 |
|   | 3-(3-hydroxyphenyl) alanine | 9 | 11 | 1 | 3 |   |   | 181.0739 | 182.0812 | 180.0666 |
|   | 3-(3,4-hydroxyphenyl) alanine | 9 | 11 | 1 | 4 |   |   | 197.0688 | 198.0761 | 196.0615 |
|   | 2-(phenyl)-glycine | 8 | 9 | 1 | 2 |   |   | 151.0633 | 152.0706 | 150.0561 |
|   | 2-(3-carboxyphenyl)-glycine | 9 | 9 | 1 | 4 |   |   | 195.0532 | 196.0604 | 194.0459 |
|   | 2-(3-carboxy-4-hydroxyphenyl) glycine | 9 | 9 | 1 | 5 |   |   | 211.0481 | 212.0554 | 210.0408 |
|   | 2-(3-hydroxyphenyl)glycine | 8 | 9 | 1 | 3 |   |   | 167.0582 | 168.0655 | 166.0510 |
| 8th page | 2-(3,5-dihydrophenyl)glycine | 8 | 9 | 1 | 4 |   |   | 183.0532 | 184.0604 | 182.0459 |
|   | 4-aminopipecolic acid | 6 | 12 | 1 | 2 |   |   | 130.0868 | 131.0941 | 129.0795 |
|   | guvacine | 6 | 9 | 1 | 2 |   |   | 127.0633 | 128.0706 | 126.0561 |
|   | 2-amino-4-(isoxazoline-5-one-2yl) butyric acid | 7 | 10 | 2 | 3 |   |   | 170.0691 | 171.0764 | 169.0619 |
|   | lathyrine | 7 | 10 | 3 | 2 |   |   | 168.0773 | 169.0846 | 167.0700 |
|   | tetrahydrolathyrine | 7 | 11 | 4 | 2 |   |   | 183.0882 | 184.0955 | 182.0809 |

[a] mass is ±1 ppm, or 0.0002-0.00001 d
[b] % changes are ±2%

TABLE 6Ib

| | parts 1-3 | | | | | | | |
|---|---|---|---|---|---|---|---|---|
| | Compound | C | H | N | O | P | S | Neutral |
| | Glu | 5 | 8 | 1 | 4 | | | 146.0453 |
| | Gln | 5 | 10 | 2 | 3 | | | 146.0691 |
| | His | 6 | 9 | 3 | 2 | | | 155.0695 |
| | Pro | 5 | 9 | 1 | 2 | | | 115.0633 |
| | Arg | 6 | 14 | 4 | 2 | | | 174.1117 |
| | Asp | 4 | 7 | 1 | 4 | | | 133.0375 |
| | Asn | 4 | 8 | 2 | 3 | | | 132.0535 |
| | Thr | 4 | 9 | 1 | 3 | | | 119.0582 |
| | Iso | 6 | 13 | 1 | 2 | | | 131.0946 |
| | Met | 5 | 11 | 1 | 2 | | 1 | 149.0511 |
| | Lys | 6 | 14 | 2 | 2 | | | 146.1055 |
| | Ser | 3 | 7 | 1 | 3 | | | 105.0426 |
| | Gly | 2 | 5 | 1 | 2 | | | 75.0320 |
| | Cys | 3 | 7 | 1 | 2 | | 1 | 121.0198 |
| | Trp | 11 | 12 | 2 | 2 | | | 204.0899 |
| | Tyr | 9 | 11 | 1 | 3 | | | 181.0739 |
| | Phe | 9 | 11 | 1 | 2 | | | 165.0790 |
| | Ala | 3 | 7 | 1 | 2 | | | 89.0477 |
| | Leu | 6 | 13 | 1 | 2 | | | 131.0946 |
| | Val | 5 | 11 | 1 | 2 | | | 117.0790 |
| Voet2 | Glucose | 6 | 12 | | 6 | | | 180.0634 |
| p446 | Glu-6-P/Fru-6-P | 6 | 11 | | 9 | 1 | | 258.0141 |
| | FBP | 6 | 10 | | 12 | 2 | | 335.9648 |
| | GAP/DHAP | 3 | 5 | | 6 | 1 | | 167.9824 |
| | 1,3 BPG | 3 | 4 | | 10 | 2 | | 261.9280 |
| | 3PG | 3 | 10 | | 7 | 1 | | 189.0164 |
| | 2PG | 3 | 4 | | 7 | 1 | | 182.9695 |
| | PEP | 3 | 2 | | 3 | 1 | | 116.9742 |
| | Pyruvate | 3 | 3 | | 3 | | | 87.0082 |
| p381 | Erythrose-4-P | 4 | 7 | | 7 | 1 | | 197.9929 |
| PI Bioc | DAHP | 7 | 9 | | 7 | 1 | | 236.0086 |
| | 3-dehydroquinate | 7 | 6 | | 6 | | | 186.0164 |
| | 3-dehydroshikimate | 7 | 6 | | 5 | | | 170.0215 |
| | Shikimate | 7 | 9 | | 5 | | | 173.0450 |
| | Shikimate-3-P | 7 | 8 | | 5 | 1 | | 203.0109 |
| | EPSP | 10 | 9 | | 7 | 1 | | 272.0086 |
| | Chorismate | 10 | 8 | | 6 | | | 224.0321 |
| p384 | Prephenate | 10 | 8 | | 6 | | | 224.0321 |
| | Arogenate | 10 | 12 | 1 | 5 | | | 226.0715 |
| p387 | Anthranilate | 7 | 7 | 1 | 2 | | | 137.0477 |
| | 5-phosphoribosyl-anthranilate or 1-(o-carboxy-phenyl amino)-1-deoxy ribulose-5-P | 12 | 13 | | 6 | 1 | | 284.0450 |
| | Indole-3-glycerol-P | 11 | 14 | 1 | 3 | 1 | | 239.0711 |
| | Indole | 8 | 7 | 1 | | | | 117.0578 |
| | | | | | | | | Neutral |
| p398 | Asp-4-P | 4 | 6 | 1 | 6 | 1 | | 194.9933 |
| | Asp-4-semialdehyde | 4 | 7 | 1 | 3 | | | 117.0426 |
| | Homoserine | 4 | 9 | 1 | 3 | | | 119.0582 |
| | Homoserine-4-P | 4 | 8 | 1 | 3 | 1 | | 149.0242 |
| p399 | 2,3-dihydrodipiconilate | 7 | 5 | 1 | 4 | | | 167.0219 |
| | Diaminopimelate | 7 | 14 | 2 | 4 | | | 190.0954 |
| | Cystathionine | 7 | 14 | 2 | 4 | | 1 | 222.0674 |
| | Homocysteine | 4 | 9 | 1 | 2 | | 1 | 135.0354 |
| p403 | alpha-ketoglutarate | 5 | 4 | | 5 | | | 144.0059 |
| | Saccharopine | 11 | 17 | 1 | 6 | | | 259.1056 |
| | alpha-aminoadipic delta-semialdehyde | 6 | 11 | 1 | 2 | | | 129.0790 |
| p405 | 2-ketobutyrate | 4 | 5 | | 3 | | | 101.0239 |
| | 2-acetohydroxybutyrate or 2-ketoisocaproate or 2-keto-3-methylvalerate | 6 | 9 | | 3 | | | 129.0552 |
| | 2-acetolactate | 5 | 7 | | 4 | | | 131.0344 |
| | 2,3-dihydroxy-3-methylvalerate | 6 | 10 | | 4 | | | 146.0579 |
| | 2,3-dihydroxyiso-valerate | 5 | 9 | | 4 | | | 133.0501 |
| | 2-ketoisovalerate | 5 | 7 | | 3 | | | 115.0395 |
| | 3-carboxy-3-hydroxy-isoproate OR | 7 | 10 | | 5 | | | 174.0528 |

TABLE 6Ib-continued

| | | | | | | | | |
|---|---|---|---|---|---|---|---|---|
| p408 | 3-carboxy-2-hydroxy-isocaproate L-glutamyl-gamma-P | 5 | 8 | 1 | 4 | 1 | | 177.0191 |
| | Glutamic-gamma-semialdehyde | 5 | 9 | 1 | 3 | | | 131.0582 |
| | delta1-pyrroline-5-carboxylate (P5C) OR delta-1-pyrroline-2-carboxylate (P2C) | 5 | 7 | 1 | 2 | | | 113.0477 |
| | L-ornithine | 5 | 12 | 2 | 2 | | | 132.0899 |
| | alpha-keto-delta-aminovalerate | 5 | 9 | 1 | 3 | | | 131.0582 |
| p1209 | Cinnamic acid or p-coumaraldehyde | 9 | 8 | | 2 | | | 148.0524 |
| | p-coumaric acid | 9 | 8 | | 3 | | | 164.0473 |
| | p-coumaryl alcohol | 9 | 9 | | 2 | | | 149.0603 |
| | coumarins or caffeic acid | 9 | 8 | | 4 | | | 180.0423 |
| | ferulic acid | 10 | 1 | | 4 | | | 184.9875 |
| | coniferaldehyde | 10 | 10 | | 3 | | | 178.0630 |
| | coniferyl alcohol | 10 | 11 | | 3 | | | 179.0708 |
| | 5-hydroxyferulic acid | 10 | 11 | | 5 | | | 211.0607 |
| | 5-hydroxy coniferaldehyde | 9 | 10 | | 4 | | | 182.0579 |
| | sinapic acid | 11 | 13 | | 5 | | | 225.0763 |
| | sinapaldehyde | 11 | 12 | | 4 | | | 208.0736 |
| | sinapyl alcohol | 11 | 13 | | 4 | | | 209.0814 |
| p1304 Dey Book | kaempferol | 15 | 10 | | 6 | | | 286.0477 |
| p118-121 | glucolactonone-6-P | 6 | 9 | 9 | | 1 | | 255.9984 |
| | glucolactonate-6-P | 6 | 10 | 10 | | 1 | | 273.0012 |
| | ribulose-5-P | 5 | 9 | 8 | | 1 | | 228.0035 |
| | ribose-5-P or xylulose-5-P | 5 | 9 | 12 | | 1 | | 291.9832 |
| | sedoheptulose-7-P | 7 | 13 | 10 | | 1 | | 288.0246 |
| p123 | acetyl coenzyme A | 23 | 35 | 7 | 17 | 3 | 1 | 806.1023 |
| | oxaloacetate | 4 | 2 | | 5 | | | 129.9902 |
| | citrate or isocitrate | 6 | 5 | | 7 | | | 189.0035 |
| | oxalosuccinate intermediate | 6 | 3 | | 7 | | | 186.9879 |
| | alpha-ketoglutarate | 5 | 4 | | 5 | | | 144.0059 |
| | alpha-hydroxyl gamma-carboxypropyl intermediate | 4 | 6 | | 3 | | | 102.0317 |
| | succinyl-CoA | 25 | 36 | 7 | 19 | 3 | 1 | 863.1000 |
| | succinate | 4 | 4 | | 4 | | | 116.0110 |
| | fumarate | 4 | 2 | | 4 | | | 113.9953 |
| | malate | 4 | 4 | | 5 | | | 132.0059 |

Part 2

| Mode+ | | | | | | | |
|---|---|---|---|---|---|---|---|
| APCI+ | | | | ESI+ | | | |
| Control | Mass | GDH | Mass | Control | Mass | GDH | Mass |
| 147.0526 | R116 | 148.0604 | L128 | 148.0604 | R140 | 148.0604 | R131 | 148.0604 |
| | L221 | 148.0604 | | | L126 | 148.0604 | L115 | 148.0604 |
| 147.0764 | L210 | 147.0764 | L119 | 147.0764 | L115 | 147.0764 | L106 | 147.0764 |
| | R107 | 147.0764 | R120 | 147.0764 | R131 | 147.0764 | | |
| 156.0768 | R143 | 156.0768 | L142 | 156.0768 | L139 | 156.0767 | L128 | 156.0767 |
| | L255 | 156.0767 | | | R162 | 156.0767 | R148 | 156.0767 |
| 116.0706 | | | L35 | 115.0685 | | | | |
| 175.1190 | | | | | | | | |
| 134.0448 | | | | | L93 | 134.0448 | L87 | 134.0448 |
| | | | | | R95 | 134.0448 | R91 | 134.0448 |
| 133.0608 | R76 | 133.0608 | L79 | 133.0608 | R92 | 133.0608 | R88 | 133.0608 |
| | | | R81 | 133.0608 | L90 | 133.0608 | L84 | 133.0607 |
| 120.0655 | L137 | 134.0812 | | | L96 | 134.0811 | L88 | 134.0812 |
| 132.1019 | L133 | 132.1019 | L77 | 132.1019 | L82 | 132.1019 | L76 | 132.1019 |
| | | | R79 | 132.1019 | | | R80 | 132.1019 |
| 150.0583 | L228 | 150.0583 | L136 | 150.0583 | L133 | 150.0583 | L122 | 150.0583 |
| | | | | | R146 | 150.0583 | R139 | 150.0583 |
| 147.1128 | L217 | 147.1128 | R125 | 147.1128 | L122 | 147.1128 | L111 | 147.1128 |
| | R113 | 147.1128 | | | R138 | 147.1128 | R128 | 147.1128 |

TABLE 6Ib-continued

```
106.0499 L30      106.0499 L14      106.0499 L16      106.0499 L16      106.0499
         R15      106.0499                   R19      106.0499 R18      106.0499
 76.0393
122.0270 L92      122.0236 L51      122.0236 R54      122.0237 R55      122.0236
         R49      122.0237 R53      122.0236
205.0972 L502     205.0971 L291     205.0971 L248     205.0971 L239     205.0971
         R276     205.0972 R285     205.0972 R310     205.0971 R276     205.0970
182.0812 L394     182.0811 L231     182.0811 L205     182.0811 L190     182.0811
         R223     182.0811 R227     182.0811 R243     182.0812 R217     182.0812
166.0863 L316     166.0863 L184     166.0863 L170     166.0862 L160     166.0862
         R177     166.0862 R181     166.0863 R198     166.0862 R180     166.0862
 90.0550
132.1019 L133     132.1019 L77      132.1019 L82      132.1019 L76      132.1019
                           R79      132.1019                            R80      132.1019
118.0863
181.0707 L388     181.0706 L226     181.0706 L211     181.0706 L189     181.0707
         R219     181.0720 R221     181.0720 R241     181.0721 R215     181.0720
259.0213
336.9720
168.9897
262.9353
190.0237
183.9767
117.9814
 88.0155
199.0002
237.0159
187.0237                            L217     187.0304 L202     187.0304
                                    R260     187.0373 R232     187.0373
171.0288
174.0523
204.0182                            L244     204.0178
273.0159
225.0394
225.0394
227.0788
138.0550 L164     138.0549 L94      138.0549 L102     138.0550 L95      138.0550
         R87      138.0550 R95      138.0550 R106     138.0550 R106     138.0550
285.0523
240.0784
118.0651
196.0006
196.0006
118.0499 L74      118.0499
120.0655 L82      120.0655 L43      120.0655 L45      120.0655 L43      120.0655
         R42      120.0655 R44      120.0655 R44      120.0655 R43      120.0655
150.0315
168.0291
191.1026 L431     191.1027 L255     191.1027 L226     191.1026 L212     191.1027
         R242     191.1026                   R273     191.1026 R242     191.1025
223.0747
136.0427
145.0132
260.1129                   L406     260.1132
130.0863 L124     130.0863 L70      130.0862 L70      130.0862 L66      130.0862
         R68      130.0862 R75      130.0862 R77      130.0862 L72      130.0862
102.0311
130.0624
132.0417
147.0652 L203     147.0652 L116     147.0652
         R105     147.0652 R119     147.0652
134.0574
116.0468
175.0601 L353     175.0601 L203     175.0601
         R201     175.0601
178.0264
132.0655 L131     132.0655 L75      132.0655 L79      132.0655 L74      132.0655
         R73      132.0655                   R83      132.0655 R78      132.0655
114.0550 L57      114.0550                                     R29      114.0550
         R29      114.0550
133.0972 L135     133.0972                   L91      133.0971 L85      133.0971
                                             R93      133.0972 R89      133.0970
132.0655 L131     132.0655 L75               L79      132.0655 L74      132.0655
         R73      132.0655                   R83      132.0655
149.0597 L225     149.0597 R125     149.0597 L125     149.0598
                                             R143     149.0598
165.0546 L310     165.0546 L179     165.0547
         R173     165.0546 R177     165.0546
```

TABLE 6Ib-continued

| | | | | |
|---|---|---|---|---|
| 150.0675 | | | | |
| 181.0495 | L385 | 181.0495 | L224 | 181.0495 |
| | R218 | 181.0495 | R220 | 181.0495 |
| 185.9948 | | | | |
| 179.0703 | L375 | 179.0703 | R213 | 179.0703 |
| | R211 | 179.0704 | | |
| 180.0781 | | | | |
| 212.0679 | | | | |
| 183.0652 | L398 | 183.0652 | | |
| | R225 | 183.0652 | | |
| 226.0836 | | | | |
| 209.0808 | L513 | 209.0807 | R292 | 209.0808 |
| | R282 | 209.0807 | | |
| 210.0887 | | | | |
| 287.0550 | | | | |
| 257.0057 | | | | |
| 274.0084 | | | | |
| 229.0108 | | | | |
| 292.9904 | | | | |
| 289.0319 | | | | |
| 807.1096 | | | | |
| 130.9975 | | | | |
| 190.0108 | | | | |
| 187.9952 | | | | |
| 145.0132 | | | | |
| 103.0390 | | | | |
| 864.1072 | | | | |
| 117.0182 | | | | |
| 115.0026 | | | | |
| 133.0132 | | | | |

Part 3

| | Mode– | | | | | | | |
|---|---|---|---|---|---|---|---|---|
| | APCI– | | | | ESI– | | | |
| | Control | Mass | GDH | Mass | Control | Mass | GDH | Mass |
| 145.0381 | L108 | 146.0459 | | | R251 | 146.0455 | R160 | 146.0459 |
| | | | | | L35 | 146.0461 | L62 | 146.0461 |
| 145.0619 | L98 | 145.0612 | L33 | 145.0612 | | | | |
| | R30/31 | ...12 + 19 | R42 | 145.0619 | | | | |
| 154.0622 | L125 | 154.0623 | L39 | 154.0622 | L38 | 154.0624 | | |
| | R37 | 154.0623 | | | R277 | 154.0623 | | |
| 114.0561 | | | | | | | | |
| 173.1044 | | | | | R419 | 174.1145 | | |
| 132.0302 | | | | | L15 | 132.0301 | L26 | 132.0301 |
| | | | | | R160 | 132.0306 | | |
| 131.0462 | L48 | 131.0463 | L14 | 131.0463 | R155 | 131.0464 | R101 | 131.0464 |
| | | | | | L13 | 131.0465 | L22 | 131.0464 |
| 118.0510 | | | | | | | | |
| 130.0874 | L43 | 130.0869 | | | R149 | 130.0871 | | |
| 148.0438 | | | | | | | | |
| 145.0983 | | | | | | | | |
| 104.0353 | | | | | L1 | 104.0353 | L1/2 | 104.0353 |
| | | | | | R28 | 104.0353 | R22 | 104.0353 |
| 74.0248 | | | | | | | | |
| 120.0125 | | | | | | | | |
| 203.0826 | L235 | 203.0826 | L73 | 203.0826 | L92 | 203.0827 | L141/142 | 203.0829 |
| | R101 | 203.0826 | R110 | 203.0826 | R541 | 203.0827 | | |
| 180.0666 | L198 | 180.0667 | L58 | 180.0667 | | | | |
| | R74 | 180.0667 | R85 | 180.0667 | | | | |
| 164.0717 | L165 | 164.0718 | L46 | 164.0717 | L53 | 164.0720 | | |
| | R54 | 164.0717 | | | | | | |
| 88.0404 | | | | | | | | |
| 130.0874 | L43 | 130.0869 | | | R149 | 130.0871 | | |
| 116.0717 | | | | | | | | |
| 179.0561 | L193 | 179.0652 | L56 | 179.0651 | L70 | 179.0653 | L98 | 179.0653 |
| | R70 | 179.0651 | R82 | 179.0651 | R427 | 179.0652 | R298 | 179.0652 |
| 257.0068 | | | | | L127 | 257.0094 | L192 | 257.0095 |
| 334.9575 | | | | | | | | |
| 166.9751 | | | | | | | | |
| 260.9207 | | | | | | | | |
| 188.0091 | | | | | | | | |
| 181.9622 | | | | | | | | |
| 115.9669 | | | | | | | | |
| 86.0009 | | | | | | | | |
| 196.9857 | | | | | R255 | 147.9969 | | |
| 235.0013 | | | | | | | | |

TABLE 6Ib-continued

| | | | | | | | | |
|---|---|---|---|---|---|---|---|---|
| 185.0092 | | | | | | R308 | 185.0060 | |
| 169.0142 | | | | | | | | |
| 172.0377 | | | | | | | | |
| 202.0037 | | | | | | | | |
| 271.0013 | | | | | | | | |
| 223.0248 | | | | | | | | |
| 223.0248 | | | | | | | | |
| 225.0643 | | | | | | | | |
| 136.0404 | | | | | | | | |
| 283.0377 | | | | | | | | |
| 238.0639 | | | | | | | | |
| 116.0506 | | | | | | | | |
| 193.9860 | | | | | | | | |
| 193.9860 | | | | | | | | |
| 116.0353 | | | | | | | | |
| 118.0510 | L22 | 118.0509 | | | | L14 | 118.0512 | |
| 148.0169 | R35 | 148.0166 | R46 | 148.0166 | | | | |
| | L112 | 148.0158 | | | | | | |
| 166.0146 | | | | | | | | |
| 189.0881 | L203 | 189.0881 | | | | | | |
| 221.0602 | | | | | | | | |
| 134.0281 | | | | | | | | |
| 142.9986 | | | | | | | | |
| 258.0983 | | | | | | | | |
| 128.0717 | | | | | | | | |
| 100.0166 | | | | | | | | |
| 128.0479 | | | | | | | | |
| 130.0272 | | | | | | | | |
| 145.0506 | | | | | | | | |
| 132.0428 | | | | | | | | |
| 114.0322 | | | | | | | | |
| 173.0455 | L177 | 173.0456 | L50 | 173.0456 | | | | |
| 176.0118 | L186 | 176.0116 | L52 | 176.0115 | R413 | 176.0117 | R285 | 176.0115 |
| | R65 | 176.0115 | R76 | 176.0114 | | | | |
| 130.0510 | L42 | 130.0510 | | | | | | |
| 112.0404 | | | | | | | | |
| 131.0826 | L50 | 131.0821 | L15 | 131.0826 | L14 | 131.0824 | L24 | 131.0829 |
| | | | | | R148 | 131.0827 | | |
| 130.0510 | L42 | 130.0510 | | | | | | |
| 147.0452 | L111 | 147.0452 | | | | | | |
| | R33 | 147.0452 | | | | | | |
| 163.0401 | L161 | 163.0402 | | | | | | |
| | R52 | 163.0401 | | | | | | |
| 148.0530 | | | | | | | | |
| 179.0350 | | | | | L69 | 179.0352 | L97 | 179.0352 |
| | | | | | R425 | 179.0350 | R297 | 179.0351 |
| 183.9802 | | | | | | | | |
| 177.0557 | | | | | | | | |
| 178.0635 | | | | | | | | |
| 210.0534 | | | | | | | | |
| 181.0506 | R75 | 181.0507 | | | | | | |
| 224.0690 | | | | | | | | |
| 207.0663 | | | | | | | | |
| 208.0741 | | | | | | | | |
| 285.0405 | | | | | | | | |
| 254.9911 | | | | | | | | |
| 271.9939 | | | | | | | | |
| 226.9962 | | | | | | | | |
| 290.9759 | | | | | | | | |
| 287.0174 | | | | | | | | |
| 805.0950 | | | | | | | | |
| 128.9829 | | | | | | | | |
| 187.9963 | | | | | | | | |
| 185.9806 | | | | | | | | |
| 142.9986 | | | | | | | | |
| 101.0244 | | | | | | | | |
| 862.0927 | | | | | | | | |
| 115.0037 | | | | | | | | |
| 112.9880 | | | | | | | | |
| 130.9986 | | | | | | | | |

TABLE 6Ic

| Special Nitrogen Metabolism Amines | Empirical Formula | Molecular Mass | Percent Change |
|---|---|---|---|
| *Leaf Extracts* | | | |
| N-caffeoylputrescine | C13H18N2O3 | 250.1317 | 196 |
| Alkaloids | | | |
| 8-acetyl quinoline | C11H0NO2 | 187.0633 | 227 |
| Scopoletin | C10H8O4 | 192.0423 | 244 |
| Phenolics | | | |
| 4-hydroxycoumarin | C9H6O3 | 162.0317 | 270 |
| N,N-dimethyl-5-methoxytryptamine | C13H18N2O | 218.1419 | 294 |
| Acetophenone | C8H8O | 120.0575 | 238 |
| *Root Extracts* | | | |
| Epinine | | 167.0946 | 222 |
| N-Caffeoylputrescine | | 250.1317 | 19 |
| Alkaloids | | | |
| alpha-Hydroxyacetophenone | | 136.0524 | 49 |
| Coumarin | | 146.0368 | 10 |
| Indole-5,6-quinone | | 147.0393 | 40 |
| 2-methyl cinnamic acid | | 162.0681 | 59 |
| 3-acetylaminoquinoline | | 186.0793 | 34 |
| 7-Ethoxy-4-methylcoumarin | | 204.0786 | 36 |
| 4,6-Dimethyl-8-tert-butylcoumarin | | 230.1307 | 27 |
| 1-O-Hexyl-2,3,5-trimethylhydroquinone | | 236.1776 | 179 |
| Phenolics | | | |
| Acetophenone | | 120.0575 | 54 |
| Nicotine | | 162.1157 | 270 |
| Swainsonine | | 173.1052 | 500 |
| (S)-6-Hydroxynicotine | | 178.1106 | 263 |
| Isoprenoid (monoterpenoid) | | | |
| Nopinone | | 138.1045 | 20 |

TABLE 6Id part 1-2

Part 1
Leaf Extracts

| Miscellaneous Compounds | Empirical Formula | Molecular Weight | Percent Change |
|---|---|---|---|
| N-Nitrosopyrrolidine | C4H8N2O | 100.0637 | 152 |
| L-threonate | C4H8O5 | 136.0372 | 370 |
| 2-furylglyoxylonitrile | C6H3NO2 | 121.0164 | 182 |
| 4-phenyl-2-thiazoleethanamide | C11H12N2S | 204.0721 | 47 |
| Diethyl 1,4 piperazine dicarboxylate | C10H18N2O4 | 230.1267 | 54 |
| Hopantenic acid | C10H18NO5 | 233.1263 | 34 |
| Menthyl acetoacetate | C14H24O3 | 240.1725 | 23 |
| N-methyl-5-allyl-cyclopentylbarbituric acid | C13H16N2O3 | 248.1161 | 208 |
| 1-(3-benzoyloxyphenyl)-3-methyl-3-methoxyurea | C16H16N2O4 | 300.1110 | 192 |
| 1,4-bis(2-(2-hydroxyethyl) amino) ethyl) amino)-9,10-anthrancenedione diacetate | C26H32N4O6 | 496.2322 | 345 | part 1-2

Part 2
Miscellaneous Compounds
Root Extracts

| | Empirical Formula | Molecular Mass | Percent Change | |
|---|---|---|---|---|
| 105) N-Nitrosopyrrolidine | C4H8N2O | 100.0637 | 714 | |
| 106) R-4-hydroxy-2-pyrrolidone | C4H7NO2 | 101.0477 | 435 | |
| 107) 3-Methoxy-1,2-propanediol | C4H10O3 | 106.0630 | 40 | |
| 108) cis-2-hexenoic acid amide | C6H11NO | 113.0841 | 26 | |
| 109) 7-Oxabicyclo[2.2.1]hept-5-ene-2,3-dione | C6H4O3 | 124.0160 | 41 | |
| 110) 2-methoxy-3-methyl-pyrazine | C6H8N2O | 124.0637 | 51 | |
| 111) Phthalic anhydride | C8H4O3 | 148.0160 | 24 | |
| 112) Gamma-Nonanolactone | C9H16O2 | 156.1150 | 43 | |
| 113) 1,5-diaatricyclo[4.2.2.2(2,5)]dodecane | C10H18N2 | 166.0994 | 625 | |
| 114) 2-Decenoic Acid | C10H18O2 | 170.1307 | 56 | |
| 115) 2,2,6,6-tetramethyl-N-nitrosopiperidine | C9H18N2O | 170.1419 | 29 | |
| 116) 1-Acetyl-4-piperidinecarboxylic acid | C8H13NO3 | 171.0895 | 270 | |
| 117) Decanamide | C10H21NO | 171.1623 | 435 | |
| 118) Sulfuric acid dipropyl ester | C6H14N2O8 | 182.0613 | 56 | |
| 119) o,o'-Iminostilbene | C4H11N | 193.0892 | 13 | 417 |
| 120) Cyclohexanepropionic acid, 4-oxo-, ethyl ester | C11H18O3 | 198.1256 | 25 | |
| 121) Cyclooctyl-1,1-dimethylurea | C11H22N2O | 198.1732 | 24 | |
| 122) Sebacic Acid | C10H18O4 | 202.1205 | 16 | |
| 123) cis-2,6-Di-tert-butylcyclohexanone | C14H26O | 210.1984 | 35 | |
| 124) 6-[2-(5-nitrofuranyl)ethenyl]-2-pyridinemethanol | C12H10N2O4 | 224.0797 | 213 | |
| 125) 5-allyl-5-butylbarbituric acid | C11H16N2O3 | 224.1161 | 22 | |
| Isothiocyanic acid 1,4-cyclohexylene-dimethylene ester | C15H24O2 | 226.0598 | 31 | |
| Tetradecanamide | C14H29NO | 227.2249 | 23 | |
| Cedrol methyl ether | C16H28O | 236.2140 | 21 | |
| Cyclohexadecanone | C16H30O | 238.2297 | 18 | |
| 1,3-Di-o-tolylguanidine | C15H17N3 | 239.1422 | 400 | |
| Menthyl acetoacetate | C14H24O3 | 240.1725 | 13 | |
| Methocarbamol | C11H15NO3 | 241.0950 | 244 | |
| N-[2,6-bis(isopropyl)phenyl]-2-imidazolidineimine | C15H23N3 | 245.1892 | 345 | |
| (−)-Ptilocaulin | C15H25N3 | 247.2048 | 294 | |
| 1-Lauryl-2-pyrrolidone | | 253.2406 | 29 | 769 |
| Hexadecanamide | C16H33NO | 255.2562 | 12 | 556 |
| Dodecylmalonic acid | C15H28O4 | 272.1988 | 46 | |
| 4-amino-N-(6-methoxy-4-pyrimidyl)-benzenesulfonamide | C11H12N4O3S | 280.0630 | 20 | |
| Rocastine | C13H19N3OS | 281.1198 | 276 | |
| Palmoxiric acid | C17H32O3 | 284.2351 | 35 | |
| Propionic acid, 3-dodecyloxy-2-ethoxy-, methyl ester | C18H36O4 | 316.2614 | 556 | |
| Benzenesulfonic acid dodecylester | C18H30O3S | 326.1916 | 63 | |
| Di(2-ethylhexyl) itaconate | C21H38O4 | 354.2770 | 40 | |
| 2,2'-ethyledene bis(4,6-di-t-butyl | C30H45O2 | 438.3498 | 12 | |

* Cigarette component
† Pesticide or Herbicide
‡ Drug

TABLE 6Ie

| Part 1-3 |
|---|

| Part 1  Leaf Extracts  Lipids | | | | | |
|---|---|---|---|---|---|
| Common Name | Systematic Name | Empirical Formula | Molecular Mass | Degree of Saturation | Percent Change |
| Pentadecanoic acid | n-Pentadecanoic acid | C15H30O2 | 242.2246 | 15:0 | 23 |
| Palmitoleic Acid | Hexadecenoic acid | C16H30O2 | 254.2246 | 16:1 | 12 |
| Palmitic acid | Hexadecanoic acid | C16H32O2 | 256.2402 | 16:0 | 30 |
| Linoleic acid | 9,12-Octadecanedioic acid | C18H32O2 | 280.2402 | 18:2 | 36 |
| Oleic acid | 9-Octadecenoic acid | C18H34O2 | 282.2559 | 18:1 | 14 |
| Lignoceric acid | Tetracosanoic acid | C24H48O2 | 368.3654 | 24:0 | 15 |
| Leaf Extracts  Lipid Derivatives | | | | | |
| Ethyl tricosanoate | | C25H50O2 | 382.3811 | | 24 |
| Ethyl tetracosanoate | | C26H52O2 | 396.3967 | | 30 |

| Part 2  Root Extracts  Lipid Derivatives | | | |
|---|---|---|---|
| | Empirical Formula | Molecular Mass | Percent Change |
| (9Z)-(13S)-12,13-Epoxyoctadeca-9,11-dienoate | | 294.2195 | 192 |
| (9Z,11E,14Z)-(13S)-Hydroperoxyoctadeca-(9,11,14)-trienoate | | 310.2144 | 238 386 |
| (9Z,11E)-(13S)-13-Hydroperoxyoctadeca-9,11-dienoate | | 312.2301 | 194 |
| 5(S)-hydroperoxy-arachidonate | | 336.2301 | 714 |
| Tetradecanoic acid, 7-oxo-, methyl ester | | 224.2140 | 43 |
| 9-Octadecenoic acid, methyl ester | | 296.2715 | 23 238 |
| Ethyl linoleate | | 308.2715 | 31 |
| Methyl 12-oxo-trans-10-octadecenoate | | 310.2508 | 25 |
| Octadecanoic acid, ethenyl ester | | 310.2872 | 17 |
| Octadecanoic acid, 12-oxo-, methyl ester | | 312.2664 | 14 |
| Diethyl tetradecanedioate | | 314.2457 | 19 |
| Propyl stearate | | 326.3185 | 18 |
| Octadecanoic acid, 9,10-epoxy-, allyl ester | | 338.2821 | 10 |
| Ethyl tricosanoate | | 382.3811 | 7 |
| Ethyl tetracosanate | | 396.3967 | 8 |
| 4,4'-Dimethylcholestatrienol | | 410.3549 | 16 |

| Part 3  Roots  Lipids | | | | | |
|---|---|---|---|---|---|
| Common Name | Systematic Name | Empirical Formula | Degree of Saturation | Molecular Mass | Percent Change |
| Pelargonic acid | n-Nonanoic acid | | 9:0 | 158.1380 | 13 |
| Capric acid | n-Decanoic acid | | 10:0 | 172.1463 | 13 |
| Undecanoic acid | n-Hendecanoic Acid | C11H2O2 | 11:0 | 186.1620 | 21 |

TABLE 6Ie-continued

| | | | Part 1-3 | | |
|---|---|---|---|---|---|
| Lauric acid | Dodecanoic acid | | 12:0 | 200.1776 | 14 |
| | trans-2-Tridecenoic acid | | 13:1 | 212.1776 | 50 |
| | Tridecanoic acid | | 13:0 | 214.1933 | 22 |
| Undecanedioic acid | | | 11:2 | 216.1362 | 14 |
| Pentadecanoic Acid | n-Pentadecanoic Acid | C15H30O2 | 15:0 | 242.2246 | 6 |
| Palmitoleic Acid | Hexadecenoic acid | C16H30O2 | 16:1 | 254.2246 | 29 |
| Palmitic acid | Hexadecanoic acid | C16H32O2 | 16:0 | 256.2402 | 4 |
| | Tetradecanedioic acid | | 14:2 | 258.1831 | 13 |
| n-Heptadecanoic Acid | | | 17:0 | 270.2559 | 19 |
| Oleic acid | 9,12-Octadecanedioic acid | C18H32O2 | 18:1 | 282.2559 | 32 |
| Stearic acid | Octadecenoic acid | C18H34O2 | 18:0 | 284.2715 | 11 |
| DL-12-Hydroxystearic acid | | | 18:0 | 300.2664 | 196 |
| | n-Nonadecanoic Acid | | 19:0 | 298.2872 | 10 |
| | Tricosanoic acid | | 23:0 | 354.3498 | 13 |
| Lignoceric acid | Tetracosanoic acid | | 24:0 | 368.3654 | 5 |

TABLE 6IF

| | Empirical Formula | Molecular Mass | Percent Change |
|---|---|---|---|
| Sugars and Derivatives in Leaf Extracts | | | |
| Bis-D-fructose 2',1:2,1'-dianhydride | C12H20O10 | 324.1056 | 208 |
| 3-Deoxy-D-glycero-D-galacto-2-nonulosonic Acid | C9H16O9 | 268.0794 | 159 |
| Sugars and Derivatives in Root Extracts | | | |
| 1,6-Anhydro-beta-D-glucopyranose | | 162.0528 | 263 |
| 2-amino-2-deoxy-D-glucose | | 179.0794 | 276 |
| Sedoheptulose anhydride | | 192.0634 | 909 |
| 3-Deoxy-D-glycero-D-galacto-2-nonulosonic Acid | | 268.0794 | 233 |
| 1,6-Anhydro-beta-D-glucopyranose 2,3,4-Triacetate | | 288.0845 | 588 |
| Bis-D-fructose 2',1:2,1'-dianhydride | | 324.1056 | 1250 |
| TCA Cycle Intermediates and Derivatives in Leaf Extracts | | | |
| Fumaric acid, monoethyl ester | C6H8O4 | 144.0423 | 56 |
| TCA Cycle Intermediates and Derivatives in Root Extracts | | | |
| Fumaric acid | | 116.0110 | 270 |
| DL-malic acid | | 134.0215 | 270 |
| Citric acid | | 192.0270 | 385 |
| Fumaric acid monoethyl ester | | 144.0423 | 345 |
| Propanedioic acid, dibutyl-, diethyl ester | | 272.1988 | 70 |

TABLE 6Ig

| | | Part 1-2 | |
|---|---|---|---|
| | Empirical Formula | Molecular Mass | Percent Change |
| | | Part 1 | |
| | Changed Amino Acids in Leaf Extracts | | |
| Protein Amino Acids | | | |
| Arginine | C6H14NO2 | 174.1117 | 127 |
| Asparagine | C4H8N2O3 | 132.0535 | 455 |
| Glutamine | C5H9NO4 | 146.0691 | 357 |
| Histidine | C6H9N3O2 | 155.0695 | 156 |
| Phenylalanine | C9H11NO2 | 165.0790 | 244 |
| Tryptophan | C11H12N2O2 | 204.0899 | 217 |
| Non-protein Amino Acids | | | |
| Ornithine | C5H12N2O2 | 132.0899 | 200 |

TABLE 6Ig-continued

Part 1-2

| | Empirical Formula | Molecular Mass | Percent Change | |
|---|---|---|---|---|
| Changed Amino Acids in Root Extracts | | | | |
| Protein Amino Acids | | | | |
| Arginine | C6H14NO2 | 174.1117 | 222 | |
| Asparagine | C4H8N2O3 | 132.0535 | 1111 | |
| Glutamine | C5H9NO4 | 146.0691 | 357 | |
| Histidine | C6H9N3O2 | 155.0695 | 833 | |
| Phenylalanine | C9H11NO2 | 165.0790 | 233 | |
| Proline | C5H9NO2 | 115.0633 | 256 | |
| Threonine | C4H9NO3 | 119.0582 | 435 | |
| Tryptophan | C11H12N2O2 | 204.0899 | 222 | |
| Valine | C5H11NO2 | 117.0790 | 435 | |
| Part 2 | | | | |
| Changed Amino Acid Derivatives in Leaf Extracts | | | | |
| N-alpha-phenylacetyl-glutamine | C13H16N2O4 | 264.111 | 227 | |
| 3-aryl-5-oxoproline ethyl ester | C13H15NO3 | 233.1052 | 303 | |
| 5-Methyl-DL-tryptophan | C12H14N2O2 | 218.1055 | 40 | |
| N-alpha-BOC-L-tryptophan | C16H20N2O4 | 304.1423 | 333 | |
| Changed Amino Acid Derivatives in Root Extracts | | | | |
| N-acetyl-L-tyrosine | | 223.0845 | 49 | |
| PTH-proline | | 232.0670 | 43 | |
| (gamma-L-glutamyl)-L-glutamine | | 275.1117 | 263 | |
| N-Benzoyl-L-tyrosine ethylester | | 314.1201 | 50 | 52 |
| 1-[N-(1-carboxy-3-phenylpropyl)-L-lysyl]-L-proline | | 405.2264 | 278 | 244 | 400 |

TABLE 6Ih

| | Empirical Formula | Molecular Mass | Percent Change | |
|---|---|---|---|---|
| Nucleic Acids in Leaf Extracts | | | | |
| 2,3-cyclopentenopyridine | C8H9N | 119.0735 | 278 | |
| Dihydro-thymine | C6H5N2O2 | 128.0586 | 227 | |
| Nucleic Acids in Root Extracts | | | | |
| Dihydro-thymine | C6H5N2O2 | 128.0586 | 238 | 278 |
| Uridine | | 244.0695 | 400 | |
| Stress and Proline Metabolism in Leaf Extracts | | | | |
| 3-hydroxy-1-pyrroline-delta-carboxylate | C5H7NO3 | 129.0426 | 133 | |
| Stress and Proline Metabolism in Root Extracts | | | | |
| 3-hydroxy-1-pyrroline-delta-carboxylate | C5H7NO3 | 129.0426 | 244 | |
| delta1-Pyrroline 2-carboxylate | | 113.0477 | 217 | |

TABLE 6Ii

| Common Name | Systematic Name | Empirical Formula | Degree of Saturation | Molecular Mass | Percent Change |
|---|---|---|---|---|---|
| DL-12-Hydroxystearic acid | | | | 300.2664 | 196 |
| Pelargonic acid | n-Nonanoic acid | | 9:0 | 158.1380 | 13 |
| Capric acid | n-Decanoic acid | | 10:0 | 172.1463 | 13 |
| Undecanoic acid | n-Hendecanoic Acid | C11H2O2 | 11:0 | 186.1620 | 21 |
| Lauric acid | Dodecanoic acid | | 12:0 | 200.1776 | 14 |
| trans-2-Tridecenoic acid | | | 13:1 | 212.1776 | 50 |
| Tridecanoic acid | | | 13:0 | 214.1933 | 22 |
| Undecanedioic acid | | | | 216.1362 | 14 |
| Pentadecanoic Acid | n-Pentadecanoic Acid | | 15:0 | 242.2246 | 6 |
| Palmitoleic Acid | Hexadecenoic acid | | 16:1 | 254.2246 | 29 |
| Palmitic acid | Hexadecanoic acid | | 16:0 | 256.2402 | 4 |
| Tetradecanedioic acid | | | 14:0 | 258.1831 | 13 |
| n-Heptadecanoic Acid | | | 17:0 | 270.2559 | 19 |
| Oleic acid | Margaric or Daturic Acid | | 18:1 | 282.2559 | 32 |
| Stearic acid | | | 18:0 | 284.2715 | 11 |
| n-Nonadecanoic Acid | | | 19:0 | 298.2872 | 10 |
| Tricosanoic acid | | | 23:0 | 354.3498 | 13 |
| Tetracosanoic acid | | | 24:0 | 368.3654 | 5 |

TABLE 6j

Miscellaneous metabolites in root extracts with altered abundance (percentage change) gdhA+ plants compared to gdhA− plants. - Part 2

| Miscellaneous Compounds | Empirical Formula | Molecular Weight | Percent Change |
|---|---|---|---|
| *Leaf Extracts* | | | |
| N-Nitrosopyrrolidine | C4H8N2O | 100.0637 | 152 |
| L-threonate | C4H8O5 | 136.0372 | 370 |
| 2-furylglyoxylonitrile | C6H3NO2 | 121.0164 | 182 |
| 4-phenyl-2-thiazoleethanamide | C11H12N2S | 204.0721 | 47 |
| Diethyl 1,4 piperazine dicarboxylate | C10H18N2O4 | 230.1267 | 54 |
| Hopantenic acid | C10H18NO5 | 233.1263 | 34 |
| Menthyl acetoacetate | C14H24O3 | 240.1725 | 23 |
| N-methyl-5-allyl-cyclopentylbarbituric acid | C13H16N2O3 | 248.1161 | 208 |
| 1-(3-benzoyloxyphenyl)-3-methyl-3-methoxyurea | C16H16N2O4 | 300.1110 | 192 |
| 1,4-bis(2-(2-hydroxyethyl) amino) ethyl) amino)-9,10-anthrancenedione diacetate | C26H32N4O6 | 496.2322 | 345 |
| *Root Extracts* | | | |
| 105) N-Nitrosopyrrolidine | C4H8N2O | 100.0637 | 714 |
| 106) R-4-hydroxy-2-pyrrolidone | C4H7NO2 | 101.0477 | 435 |
| 107) 3-Methoxy-1,2-propanediol | C4H10O3 | 106.0630 | 40 |
| 108) cis-2-hexenoic acid amide | C6H11NO | 113.0841 | 26 |
| 109) 7-Oxabicyclo[2.2.1]-hept-5-ene-2,3-dione | C6H4O3 | 124.0160 | 41 |
| 110) 2-methoxy-3-methyl-pyrazine | C6H8N2O | 124.0637 | 51 |
| 111) Phthalic anhydride | C8H4O3 | 148.0160 | 24 |
| 112) Gamma-Nonanolactone | C9H16O2 | 156.1150 | 43 |
| 113) 1,5-diatricyclo [4.2.2.2(2,5)]dodecane | C10H18N2 | 166.0994 | 625 |
| 114) 2-Decenoic Acid | C10H18O2 | 170.1307 | 56 |
| 115) 2,2,6,6-tetramethyl-N-nitrosopiperidine | C9H18N2O | 170.1419 | 29 |
| 116) 1-Acetyl-4-piperidinecarboxylic acid | C8H13NO3 | 171.0895 | 270 |
| 117) Decanamide | C10H21NO | 171.1623 | 435 |
| 118) Sulfuric acid dipropyl ester | C6H14N2O8 | 182.0613 | 56 |
| 119) o,o'-Iminostilbene | C4H11N | 193.0892 | 13 417 |
| 120) Cyclohexanepropionic acid, 4-oxo-, ethyl ester | C11H18O3 | 198.1256 | 25 |
| 121) Cyclooctyl-1,1-dimethylurea | C11H22N2O | 198.1732 | 24 |
| 122) Sebacic Acid | C10H18O4 | 202.1205 | 16 |
| 123) cis-2,6-Di-tert-butylcyclohexanone | C14H26O | 210.1984 | 35 |
| 124) 6-[2-(5-nitrofuranyl)ethenyl]-2-pyridinemethanol | C12H10N2O4 | 224.0797 | 213 |
| 125) 5-allyl-5-butylbarbituric acid | C11H16N2O3 | 224.1161 | 22 |
| Isothiocyanic acid 1,4-cyclohexylene-dimethylene ester | C15H24O2 | 226.0598 | 31 |
| Tetradecanamide | C14H29NO | 227.2249 | 23 |
| Cedrol methyl ether | C16H28O | 236.2140 | 21 |
| Cyclohexadecanone | C16H30O | 238.2297 | 18 |
| 1,3-Di-o-tolylguanidine | C15H17N3 | 239.1422 | 400 |
| Menthyl acetoacetate | C14H24O3 | 240.1725 | 13 |
| Methocarbamol | C11H15NO3 | 241.0950 | 244 |
| N-[2,6-bis(isopropyl)-phenyl]-2-imidazolidineimine | C15H23N3 | 245.1892 | 345 |
| (−)-Ptilocaulin | C15H25N3 | 247.2048 | 294 |
| 1-Lauryl-2-pyrrolidone | | 253.2406 | 29 769 |
| Hexadecanamide | C16H33NO | 255.2562 | 12 556 |
| Dodecylmalonic acid | C15H28O4 | 272.1988 | 46 |
| 4-amino-N-(6-methoxy-4-pyrimidyl)-benzenesulfonamide | C11H12N4O3S | 280.0630 | 20 |
| Rocastine | C13H19N3OS | 281.1198 | 276 |
| Palmoxiric acid | C17H32O3 | 284.2351 | 35 |
| Propionic acid, 3-dodecyloxy-2-ethoxy-, methyl ester | C18H36O4 | 316.2614 | 556 |
| Benzenesulfonic acid dodecylester | C18H30O3S | 326.1916 | 63 |
| Di(2-ethylhexyl) itaconate | C21H38O4 | 354.2770 | 40 |
| 2,2'-ethyledene bis(4,6-di-t-butyl | C30H45O2 | 438.3498 | 12 |

*Cigarette component  
†Pesticide or Herbicide  
‡Drug  
$^a$mass is ±1 ppm, or 0.0002-0.00001 d  
$^b$% changes are ±2%

TABLE 7

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 247.0455 | 247.0455 | C8H5N7O3P0S0Cl0 | 0.2 |
| 180.0313 | 180.0313 | | 0.2 |
| 556.0871 | 556.0871 | C13H32N8O4P0S6Cl0 | 0.3 |
| 279.0718 | 279.0718 | C17H13N1O1P0S1Cl0 | 0.3 |
| 260.0382 | 260.0382 | C9H13N2O3P1S1Cl0 | 0.3 |
| 400.2010 | 400.2010 | C23H24N6O1P0S0Cl0 | 0.3 |
| 225.0637 | 225.0637 | C10H11N1O5P0S0Cl0 | 0.3 |
| 290.1577 | 290.1577 | | 0.3 |
| 216.0610 | 216.0610 | C13H12N0O1P0S1Cl0 | 0.3 |
| 175.9634 | 175.9634 | C2H8N0O3P0S3Cl0 | 0.3 |
| 262.0539 | 262.0539 | C9H15N2O3P1S1Cl0 | 0.4 |
| 314.1046 | 314.1046 | C12H26N0O3P0S3Cl0 | 0.4 |
| 362.0897 | 362.0897 | C12H18N4O7P0S1Cl0 | 0.4 |
| 202.1205 | 202.1205 | C10H18N0O4P0S0Cl0 | 0.4 |
| 580.8951 | 580.8951 | C6H24N5O6P1S9Cl0 (not found . . . ) | 0.4 |
| 282.0330 | 282.0330 | C9H15N0O6P1S1Cl0 | 0.4 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 198.0743 | 198.0743 | C6H14N0O7P0S0Cl0 | 0.4 |
| 247.0458 | 247.0458 | C8H5N7O3P0S0Cl0 | 0.4 |
| 220.0174 | 220.0174 | | 0.4 |
| 293.0385 | 293.0385 | C9H11N1O10P0S0Cl0 | 0.4 |
| 263.0195 | 263.0195 | C8H10N1O7P1S0Cl0 | 0.4 |
| 295.0457 | 295.0457 | C9H14N1O8P1S0Cl0 | 0.4 |
| 362.9451 | 362.9451 | C10H6N1O10P1S1Cl0 | 0.4 |
| 232.0350 | 232.0350 | C5H13N0O8P1S0Cl0 (Ribitol 5-phosphate Xylitol 5-phosphate L-Arabinitol 5-phosphate) | 0.4 |
| 234.0417 | 234.0417 | | 0.4 |
| 633.1015 | 633.1015 | C25H23N5O13P0S1Cl0 | 0.5 |
| 814.3406 | 814.3406 | C37H67N0O9P1S4Cl0 | 0.5 |
| 216.0313 | 216.0313 | C6H16N0O2P0S3Cl0 | 0.5 |
| 554.0801 | 554.0801 | C12H27N8O9P1S3Cl0 | 0.5 |
| 340.0685 | 340.0685 | C11H13N6O5P1S0Cl0 | 0.5 |
| 165.0427 | 165.0427 | C8H7N1O3P0S0Cl0 | 0.5 |
| 726.3577 | 726.3577 | C41H46N10O1P0S1Cl0 | 0.5 |
| 195.0533 | 195.0533 | C9H9N1O4P0S0Cl0 | 0.5 |
| 248.0939 | 248.0939 | C8H16N4O3P0S1Cl0 | 0.5 |
| 246.0419 | 246.0419 | C7H18N0O3P0S3Cl0 | 0.5 |
| 176.1203 | 176.1203 | C12H16N0O1P0S0Cl0 | 0.5 |
| 197.1497 | 197.1497 | | 0.5 |
| 256.0542 | 256.0542 | C6H12N2O9P0S0Cl0 | 0.5 |
| 144.0425 | 144.0425 | C6H8N0O4P0S0Cl0 | 0.5 |
| 206.0103 | 206.0103 | | 0.5 |
| 308.0324 | 308.0324 | C10H16N2O3P0S3Cl0 | 0.5 |
| 620.3549 | 620.3549 | C39H48N4O1P0S1Cl0 | 0.5 |
| 165.0427 | 165.0427 | C8H7N1O3P0S0Cl0 | 0.5 |
| 214.0089 | 214.0089 | C12H6N0O2P0S1Cl0 | 0.5 |
| 702.3464 | 702.3464 | C40H46N8O2P0S1Cl0 | 0.5 |
| 751.1207 | 751.1207 | C20H33N9O16P0S3Cl0 | 0.5 |
| 236.0573 | 236.0573 | | 0.5 |
| 959.5004 | 959.5004 | C50H69N7O12P0S0Cl0 | 0.5 |
| 187.9969 | 187.9969 | C7H8N0O2P0S2Cl0 | 0.5 |
| 165.0427 | 165.0427 | C8H7N1O3P0S0Cl0 | 0.5 |
| 813.2638 | 813.2638 | C44H44N7O3P1S2Cl0 | 0.5 |
| 538.3287 | 538.3287 | C18H38N18O0P0S1Cl0 | 0.5 |
| 267.0966 | 267.0966 | C10H13N5O4P0S0Cl0 | 0.5 |
| 165.0428 | 165.0428 | C8H7N1O3P0S0Cl0 | 0.5 |
| 346.8963 | 346.8963 | | 0.5 |
| 326.1409 | 326.1409 | C14H30N0O2P0S3Cl0 | 0.5 |
| 441.2576 | 441.2576 | C19H39N1O10P0S0Cl0 | 0.6 |
| 556.1132 | 556.1132 | C17H32N0O16P0S2Cl0 | 0.6 |
| 248.0381 | 248.0381 | C5H12N0O11P0S0Cl0 | 0.6 |
| 410.1028 | 410.1028 | C11H26N2O10P0S2Cl0 | 0.6 |
| 472.0727 | 472.0727 | C18H32N0O2P0S6Cl0 | 0.6 |
| 187.4945 | 187.4945 | | 0.6 |
| 998.8681 | 998.8681 | C68H110N4O1P0S0Cl0 | 0.6 |
| 163.9998 | 163.9998 | | 0.6 |
| 817.4681 | 817.4681 | C44H67N9O0P0S3Cl0 | 0.6 |
| 134.1483 | 134.1483 | | 0.6 |
| 935.7902 | 935.7902 | C55H105N3O8P0S0Cl0 | 0.6 |
| 276.9898 | 276.9898 | C9H11N1O3P0S3Cl0 | 0.6 |
| 700.4175 | 700.4175 | C45H56N4O1P0S1Cl0 | 0.6 |
| 408.1307 | 408.1307 | C16H29N2O4P1S2Cl0 | 0.6 |
| 211.9723 | 211.9723 | C4H5N0O8P1S0Cl0 | 0.6 |
| 248.0508 | 248.0508 | C13H12N0O3P0S1Cl0 | 0.6 |
| 812.5610 | 812.5610 | C46H72N10O1P0S1Cl0 | 0.6 |
| 226.0689 | 226.0689 | C7H14N0O8P0S0Cl0 | 0.6 |
| 388.1206 | 388.1206 | C18H20N4O4P0S1Cl0 | 0.6 |
| 119.0038 | 119.0038 | | 0.6 |
| 433.1229 | 433.1229 | C18H27N1O7P0S2Cl0 | 0.6 |
| 455.0910 | 455.0910 | C15H21N1O15P0S0Cl0 | 0.6 |
| 631.5536 | 631.5536 | | 0.6 |
| 312.2302 | 312.2302 | C18H32N0O4P0S0Cl0 | 0.6 |
| 175.9634 | 175.9634 | C2H8N0O3P0S3Cl0 | 0.6 |
| 292.1200 | 292.1200 | C10H20N4O4P0S1Cl0 | 0.6 |
| 257.9686 | 257.9686 | C6H10N0O5P0S3Cl0 | 0.6 |
| 392.0268 | 392.0268 | C11H20N0O9P0S3Cl0 | 0.6 |
| 710.3536 | 710.3536 | C25H47N18O3P1S1Cl0 | 0.6 |
| 700.4181 | 700.4181 | C37H68N2O2P0S4Cl0 | 0.6 |
| 614.4005 | 614.4005 | C37H58N0O5P0S1Cl0 | 0.6 |
| 538.3286 | 538.3286 | C22H42N12O2P0S1Cl0 | 0.6 |
| 230.1005 | 230.1005 | | 0.6 |
| 444.0785 | 444.0785 | C12H28N0O11P0S3Cl0 | 0.6 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 842.4842 | 842.4842 | C42H78N6O1P0S5Cl0 | 0.6 |
| 195.9985 | 195.9985 | | 0.6 |
| 785.4831 | 785.4831 | C38H64N1O5P1S0Cl0 | 0.6 |
| 626.4060 | 626.4060 | C33H59N2O7P1S0Cl0 | 0.6 |
| 211.9724 | 211.9724 | C4H5N0O8P1S0Cl0 | 0.7 |
| 309.0160 | 309.0160 | C10H15N1O4P0S3Cl0 | 0.7 |
| 400.3458 | 400.3458 | C26H44N2O1P0S0Cl0 | 0.7 |
| 558.3446 | 558.3446 | C27H58N0O5P0S3Cl0 | 0.7 |
| 242.0038 | 242.0038 | C6H14N2O0P0S4Cl0 | 0.7 |
| 542.1667 | 542.1667 | C27H34N4O0P0S4Cl0 | 0.7 |
| 375.9971 | 375.9971 | C11H12N4O5P0S3Cl0 (not found...) | 0.7 |
| 377.9954 | 377.9954 | C11H6N8O4P0S2Cl0 (not found) | 0.7 |
| 658.2755 | 658.2755 | C35H50N2O2P0S4Cl0 (not found...) | 0.7 |
| 240.0844 | 240.0844 | C8H16N0O8P0S0Cl0 | 0.7 |
| 814.4421 | 814.4421 | C45H67N0O11P1S0Cl0 | 0.7 |
| 572.0887 | 572.0887 | C13H30N6O11P2S2Cl0 | 0.7 |
| 410.0909 | 410.0909 | C17H14N8O3P0S1Cl0 | 0.7 |
| 674.4075 | 674.4075 | C28H54N10O9P0S0Cl0 (not found...) | 0.7 |
| 186.9975 | 186.9975 | C3H9N1O4P0S2Cl0 | 0.7 |
| 966.5043 | 966.5043 | C59H70N2O10P0S0Cl0 | 0.7 |
| 872.4091 | 872.4091 | C31H60N2O0O2P0S4Cl0 | 0.7 |
| 250.0265 | 250.0265 | C8H14N2O1P0S3Cl0 | 0.7 |
| 634.3689 | 634.3689 | C31H50N6O8P0S0Cl0 | 0.7 |
| 542.1885 | 542.1885 | C17H38N10O0P0S5Cl0 | 0.7 |
| 276.1424 | 276.1424 | | 0.7 |
| 398.0433 | 398.0433 | C15H16N2O7P2S0Cl0 (not found...) | 0.7 |
| 234.1021 | 234.1021 | C10H19N0O4P1S0Cl0 | 0.7 |
| 866.6621 | 866.6621 | C48H99N0O6P1S2Cl0 | 0.7 |
| 568.3009 | 568.3009 | C29H40N6O6P0S0Cl0 | 0.7 |
| 866.6606 | 866.6606 | C50H94N2O5P0S2Cl0 | 0.7 |
| 813.2446 | 813.2446 | C37H52N1O11P1S3Cl0 | 0.7 |
| 676.3511 | 676.3511 | C42H48N2O6P0S0Cl0 | 0.7 |
| 997.8496 | 997.8496 | C63H115N1O5P0S1Cl0 | 0.7 |
| 576.1478 | 576.1478 | C22H33N4O8P1S2Cl0 | 0.7 |
| 274.0173 | 274.0173 | C6H10N0O12P0S0Cl0 | 0.7 |
| 159.9860 | 159.9860 | C5H5N2O0P0S1Cl1 (4-Chloro-2-methylthiopyrimidine) | 0.7 |
| 980.8045 | 980.8045 | C62H108N0O8P0S0Cl0 | 0.7 |
| 428.2324 | 428.2324 | C25H28N6O1P0S0Cl0 | 0.7 |
| 566.0542 | 566.0542 | C18H23N4O11P1S2Cl0 | 0.7 |
| 403.1111 | 403.1111 | C14H17N11O0P0S2Cl0 | 0.7 |
| 380.0723 | 380.0723 | C11H21N0O12P0S0Cl1 | 0.7 |
| 956.4878 | 956.4878 | C45H85N2O9P1S4Cl0 | 0.7 |
| 216.0401 | 216.0401 | C5H13N0O7P1S0Cl0 | 0.7 |
| 280.0988 | 280.0988 | C12H24N0O1P0S3Cl0 (not found) | 0.7 |
| 382.1089 | 382.1089 | C18H22N0O7P0S1Cl0 | 0.7 |
| 373.9996 | 373.9996 | C12H22N0O1P0S6Cl0 (not found...) | 0.7 |
| 614.3699 | 614.3699 | C27H46N14O1P0S1Cl0 | 0.7 |
| 492.2746 | 492.2746 | C21H36N10O2P0S1Cl0 | 0.7 |
| 436.2949 | 436.2949 | C25H36N6O1P0S0Cl0 | 0.7 |
| 818.6604 | 818.6604 | C9H11N1O19P2S10Cl0 | 0.7 |
| 543.7892 | 543.7892 | C11H12N0O5P0S10Cl0 | 0.7 |
| 538.1020 | 538.1020 | C22H24N4O8P1S0Cl1 | 0.7 |
| 480.1958 | 480.1958 | C15H25N14O3P1S0Cl0 | 0.7 |
| 780.1399 | 780.1399 | C30H53N0O5P1S8Cl0 (not found) | 0.7 |
| 455.0905 | 455.0905 | C12H23N7O6P2S1Cl0 | 0.7 |
| 484.2950 | 484.2950 | C29H36N6O1P0S0Cl0 | 0.7 |
| 558.0845 | 558.0845 | C11H28N8O10P2S2Cl0 | 0.7 |
| 677.1009 | 677.1009 | C19H32N7O12P1S3Cl0 | 0.7 |
| 486.1858 | 486.1858 | C22H34N2O6P0S2Cl0 | 0.7 |
| 648.3846 | 648.3846 | C32H52N6O8P0S0Cl0 | 0.7 |
| 218.0193 | 218.0193 | C5H11N0O7P0S0Cl1 | 0.7 |
| 195.9985 | 195.9985 | | 0.7 |
| 409.0978 | 409.0978 | C14H23N3O7P0S2Cl0 | 0.7 |
| 280.1417 | 280.1417 | | 0.7 |
| 980.4844 | 980.4844 | C41H86N6O8P2S4Cl0 | 0.8 |
| 708.1163 | 708.1163 | C20H28N12O11P0S3Cl0 | 0.8 |
| 192.0634 | 192.0634 | C7H12N0O6P0S0Cl0 | 0.8 |
| 425.0720 | 425.0720 | C17H11N7O7P0S0Cl0 | 0.8 |
| 218.0103 | 218.0103 | C5H14N0O3P0S3Cl0 | 0.8 |
| 174.0166 | 174.0166 | C6H6N0O6P0S0Cl0 | 0.8 |
| 240.0846 | 240.0846 | C8H16N0O8P0S0Cl0 | 0.8 |
| 260.0298 | 260.0298 | C6H13N0O9P1S0Cl0 | 0.8 |
| 161.9843 | 161.9843 | | 0.8 |
| 274.2302 | 274.2302 | C19H30N0O1P0S0Cl0 | 0.8 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 860.4888 | 860.4888 | C45H64N8O9P0S0Cl0 | 0.8 |
| 524.1787 | 524.1787 | C29H33N0O5P1S1Cl0 | 0.8 |
| 810.4380 | 810.4380 | C41H63N8O5P1S1Cl0 | 0.8 |
| 164.0536 | 164.0536 |  | 0.8 |
| 676.3703 | 676.3703 | C29H61N2O11P1S1Cl0 | 0.8 |
| 958.5227 | 958.5227 | C56H82N2O3P0S4Cl0 | 0.8 |
| 556.0861 | 556.0861 | C19H26N2O13P1S0Cl1 (not found) | 0.8 |
| 540.2692 | 540.2692 | C27H44N2O5P0S2Cl0 | 0.8 |
| 922.7783 | 922.7783 | C48H98N12O5P0S0Cl0 | 0.8 |
| 386.0807 | 386.0807 | C11H18N2O13P0S0Cl0 | 0.8 |
| 646.3737 | 646.3737 | C30H50N10O4P0S1Cl0 | 0.8 |
| 901.7761 | 901.7761 | C14H10N14O13P0S10Cl0 | 0.8 |
| 600.3843 | 600.3843 | C28H60N2O7P0S2Cl0 | 0.8 |
| 362.9447 | 362.9447 | C10H6N1O10P1S1Cl0 | 0.8 |
| 632.1069 | 632.1069 | C15H28N12O8P0S4Cl0 | 0.8 |
| 214.0088 | 214.0088 | C12H6N0O2P0S1Cl0 | 0.8 |
| 286.1931 | 286.1931 | C19H26N0O2P0S0Cl0 | 0.8 |
| 294.0556 | 294.0556 | C8H15N4O4P1S1Cl0 | 0.8 |
| 242.0038 | 242.0038 | C6H14N2O0P0S4Cl0 | 0.8 |
| 450.3108 | 450.3108 | C26H38N6O1P0S0Cl0 | 0.8 |
| 398.0435 | 398.0435 | C9H18N8O2P0S4Cl0 | 0.8 |
| 225.0637 | 225.0637 | C10H11N1O5P0S0Cl0 | 0.8 |
| 296.0422 | 296.0422 | C9H9N6O4P1S0Cl0 | 0.8 |
| 912.4503 | 912.4503 | C32H68N18O5P0S4Cl0 | 0.8 |
| 474.9956 | 474.9956 | C19H13N3O6P0S3Cl0 | 0.8 |
| 392.0356 | 392.0356 | C14H20N2O3P0S4Cl0 | 0.8 |
| 164.0537 | 164.0537 |  | 0.8 |
| 360.1266 | 360.1266 | C12H24N0O12P0S0Cl0 | 0.8 |
| 456.1097 | 456.1097 | C13H24N6O8P0S2Cl0 | 0.8 |
| 373.1006 | 373.1006 | C10H24N5O4P1S2Cl0 | 0.8 |
| 226.0688 | 226.0688 | C7H14N0O8P0S0Cl0 | 0.8 |
| 901.3767 | 901.3767 | C32H65N13O7P2S3Cl0 | 0.8 |
| 404.0915 | 404.0915 | C14H29N0O5P1S3Cl0 | 0.8 |
| 428.2324 | 428.2324 | C25H28N6O1P0S0Cl0 | 0.8 |
| 180.0634 | 180.0634 | C6H12N0O6P0S0Cl0 | 0.8 |
| 594.1585 | 594.1585 | C27H30N0O15P0S0Cl0 | 0.8 |
| 384.1910 | 384.1910 | C19H24N6O3P0S0Cl0 | 0.8 |
| 814.3409 | 814.3409 | C40H58N6O4P0S4Cl0 | 0.8 |
| 778.1441 | 778.1441 | C37H46N0O4P0S7Cl0 | 0.8 |
| 308.1177 | 308.1177 | C16H21N0O4P1S0Cl0 | 0.8 |
| 352.2017 | 352.2017 | C16H33N0O6P1S0Cl0 | 0.8 |
| 230.2017 | 230.2017 |  | 0.8 |
| 258.0780 | 258.0780 | C9H22N0O2P0S3Cl0 | 0.8 |
| 243.9986 | 243.9986 | C5H9N0O9P1S0Cl0 | 0.8 |
| 409.0983 | 409.0983 | C22H19N1O5P0S1Cl0 | 0.8 |
| 260.0295 | 260.0295 | C9H4N6O4P0S0Cl0 | 0.8 |
| 179.9946 | 179.9946 |  | 0.8 |
| 308.1177 | 308.1177 | C16H21N0O4P1S0Cl0 | 0.8 |
| 484.2958 | 484.2958 | C26H45N0O6P1S0Cl0 | 0.8 |
| 408.1305 | 408.1305 | C16H29N2O4P1S2Cl0 | 0.8 |
| 779.1427 | 779.1427 | C27H34N13O5P1S4Cl0 | 0.8 |
| 278.0313 | 278.0313 | C7H18N0O5P0S3Cl0 | 0.8 |
| 257.9688 | 257.9688 | C6H10N0O5P0S3Cl0 | 0.8 |
| 734.3358 | 734.3358 | C40H54N4O3P0S3Cl0 | 0.8 |
| 306.1350 | 306.1350 | C12H23N2O5P1S0Cl0 | 0.8 |
| 216.0400 | 216.0400 | C5H13N0O7P1S0Cl0 | 0.8 |
| 558.0829 | 558.0829 | C13H23N10O9P1S2Cl0 | 0.8 |
| 264.0159 | 264.0159 | C6H16N0O5P0S3Cl0 | 0.8 |
| 364.0979 | 364.0979 | C10H16N6O9P0S0Cl0 | 0.8 |
| 202.0455 | 202.0455 | C12H10N0O1P0S1Cl0 | 0.8 |
| 194.0102 | 194.0102 |  | 0.8 |
| 260.0937 | 260.0937 |  | 0.8 |
| 250.0357 | 250.0357 | C7H11N2O6P1S0Cl0 | 0.8 |
| 614.4027 | 614.4027 | C30H66N2O2P0S4Cl0 | 0.8 |
| 278.1043 | 278.1043 | C12H15N6O0P0S0Cl1 | 0.8 |
| 580.9007 | 580.9007 | C6H20N3O14P1S6Cl0 | 0.8 |
| 662.3541 | 662.3541 | C34H46N8O6P0S0Cl0 | 0.8 |
| 582.3222 | 582.3222 | C33H47N2O5P1S0Cl0 | 0.8 |
| 872.4084 | 872.4084 | C40H72N0O14P0S3Cl0 | 0.8 |
| 134.1484 | 134.1484 |  | 0.8 |
| 180.0633 | 180.0633 | C6H12N0O6P0S0Cl0 | 0.8 |
| 216.0848 | 216.0848 |  | 0.8 |
| 316.1732 | 316.1732 |  | 0.8 |
| 943.5295 | 943.5295 | C47H70N13O6P1S0Cl0 | 0.9 |
| 480.0809 | 480.0809 | C18H13N10O5P1S0Cl0 | 0.9 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 307.0831 | 307.0831 | C12H14N5O3P1S0Cl0 | 0.9 |
| 390.9221 | 390.9221 | C11H6N1O9P1S2Cl0 | 0.9 |
| 202.0453 | 202.0453 | C12H10N0O1P0S1Cl0 | 0.9 |
| 254.1285 | 254.1285 | C11H23N0O4P0S0Cl1 | 0.9 |
| 218.0193 | 218.0193 | C5H11N0O7P0S0Cl1 | 0.9 |
| 384.0848 | 384.0848 | C15H13N8O3P1S0Cl0 | 0.9 |
| 913.1550 | 913.1550 | C32H51N9O4P0S9Cl0 | 0.9 |
| 248.0508 | 248.0508 | C13H12N0O3P0S1Cl0 | 0.9 |
| 852.7224 | 852.7224 | C49H92N10O0P0S1Cl0 | 0.9 |
| 519.2260 | 519.2260 | C17H34N11O4P1S1Cl0 | 0.9 |
| 248.0308 | 248.0308 | C6H17N0O4P1S2Cl0 | 0.9 |
| 600.3843 | 600.3843 | C28H60N2O7P0S2Cl0 | 0.9 |
| 492.9357 | 492.9357 | C10H5N9O9P1S1Cl1 | 0.9 |
| 425.1317 | 425.1317 | C14H28N5O4P1S2Cl0 | 0.9 |
| 364.0982 | 364.0982 | C11H28N2O3P0S4Cl0 | 0.9 |
| 620.3542 | 620.3542 | C28H61N0O8P1S2Cl0 | 0.9 |
| 460.1764 | 460.1764 | C13H28N6O12P0S0Cl0 | 0.9 |
| 560.0958 | 560.0958 | C16H21N10O9P1S1Cl0 | 0.9 |
| 824.4088 | 824.4088 | C35H70N0O17P2S0Cl0 | 0.9 |
| 450.3107 | 450.3107 | C26H38N6O1P0S0Cl0 | 0.9 |
| 332.1749 | 332.1749 | C19H20N6O0P0S0Cl0 | 0.9 |
| 708.1211 | 708.1211 | C17H34N12O9P2S3Cl0 | 0.9 |
| 352.2009 | 352.2009 | C19H32N2O0P0S2Cl0 | 0.9 |
| 286.9656 | 286.9656 | C10H6N1O5P0S1Cl1 | 0.9 |
| 264.1489 | 264.1489 | C12H25N0O4P1S0Cl0 | 0.9 |
| 560.0964 | 560.0964 | C15H28N8O7P0S4Cl0 | 0.9 |
| 494.9326 | 494.9326 | C10H17N5O4P0S7Cl0 | 0.9 |
| 233.9543 | 233.9543 | | 0.9 |
| 248.0380 | 248.0380 | C5H12N0O11P0S0Cl0 | 0.9 |
| 399.3232 | 399.3232 | | 0.9 |
| 970.4143 | 970.4143 | C38H68N8O17P2S0Cl0 | 0.9 |
| 436.2953 | 436.2953 | C22H45N0O6P1S0Cl0 | 0.9 |
| 230.1005 | 230.1005 | | 0.9 |
| 542.1886 | 542.1886 | C21H39N2O8P1S2Cl0 | 0.9 |
| 516.1320 | 516.1320 | C15H30N6O8P2S1Cl0 | 0.9 |
| 519.3326 | 519.3326 | C26H50N1O7P1S0Cl0 | 0.9 |
| 214.0518 | 214.0518 | C7H18N0O1P0S3Cl0 | 0.9 |
| 718.3878 | 718.3878 | C28H59N6O13P1S0Cl0 | 0.9 |
| 318.1059 | 318.1059 | C12H18N2O8P0S0Cl0 | 0.9 |
| 441.2571 | 441.2571 | C17H27N15O0P0S0Cl0 | 0.9 |
| 514.0858 | 514.0858 | C16H34N0O8P0S5Cl0 | 0.9 |
| 250.0269 | 250.0269 | C8H14N2O1P0S3Cl0 | 0.9 |
| 646.3768 | 646.3768 | C35H66N0O0P0S5Cl0 | 0.9 |
| 457.0535 | 457.0535 | C15H23N1O9P0S3Cl0 | 0.9 |
| 780.1411 | 780.1411 | C36H44N0O7P0S6Cl0 | 0.9 |
| 832.6793 | 832.6793 | C51H92N0O8P0S0Cl0 | 0.9 |
| 430.0783 | 430.0783 | C20H14N8O0P0S2Cl0 | 0.9 |
| 648.3843 | 648.3843 | C32H60N2O7P0S2Cl0 | 0.9 |
| 418.2177 | 418.2177 | C16H30N6O7P0S0Cl0 | 0.9 |
| 304.1201 | 304.1201 | C11H20N4O4P0S1Cl0 | 0.9 |
| 232.0798 | 232.0798 | | 0.9 |
| 726.3588 | 726.3588 | C34H38N20O0P0S0Cl0 | 0.9 |
| 246.0353 | 246.0353 | C6H18N2O0P0S4Cl0 | 0.9 |
| 187.9965 | 187.9965 | C7H8N0O2P0S2Cl0 | 0.9 |
| 632.1069 | 632.1069 | C14H34N8O10P2S3Cl0 | 0.9 |
| 818.6603 | 818.6603 | C46H94N2O5P0S2Cl0 | 0.9 |
| 412.9429 | 412.9429 | C14H8N1O8P1S2Cl0 | 0.9 |
| 433.1233 | 433.1233 | C18H19N5O8P0S0Cl0 | 0.9 |
| 154.4306 | 154.4306 | | 0.9 |
| 426.0682 | 426.0682 | C17H14N8O2P0S2Cl0 | 0.9 |
| 939.8298 | 939.8298 | C23H24N0O22P0S9Cl0 | 0.9 |
| 220.0173 | 220.0173 | | 0.9 |
| 218.0467 | 218.0467 | | 0.9 |
| 388.1493 | 388.1493 | C17H20N6O5P0S0Cl0 | 0.9 |
| 144.0423 | 144.0423 | C6H8N0O4P0S0Cl0 | 0.9 |
| 274.2664 | 274.2664 | C20H34N0O0P0S0Cl0 | 0.9 |
| 317.1112 | 317.1112 | C13H19N1O8P0S0Cl0 | 0.9 |
| 270.1622 | 270.1622 | C18H22N0O2P0S0Cl0 | 0.9 |
| 128.1207 | 128.1207 | | 0.9 |
| 206.0598 | 206.0598 | | 0.9 |
| 382.2209 | 382.2209 | C18H38N0O4P0S2Cl0 | 0.9 |
| 486.2500 | 486.2500 | C21H42N0O10P0S1Cl0 | 1.0 |
| 357.1058 | 357.1058 | C10H24N5O3P1S2Cl0 | 1.0 |
| 488.3219 | 488.3219 | C24H48N4O2P0S2Cl0 | 1.0 |
| 616.1371 | 616.1371 | C30H33N0O8P1S2Cl0 | 1.0 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 198.0744 | 198.0744 |  | 1.0 |
| 250.0842 | 250.0842 | C13H14N0O5P0S0Cl0 | 1.0 |
| 422.4488 | 422.4488 | C29H58N0O1P0S0Cl0 | 1.0 |
| 453.2536 | 453.2536 | C18H40N5O4P1S1Cl0 | 1.0 |
| 734.1436 | 734.1436 | C22H40N0O23P2S0Cl0 | 1.0 |
| 176.0537 | 176.0537 |  | 1.0 |
| 260.0573 | 260.0573 | C8H20N0O3P0S3Cl0 | 1.0 |
| 112.1001 | 112.1001 | C6H12N2O0P0S0Cl0 | 1.0 |
| 760.4723 | 760.4723 | C43H64N6O4P0S1Cl0 | 1.0 |
| 456.2635 | 456.2635 | C27H40N2O0P0S2Cl0 | 1.0 |
| 568.3014 | 568.3014 | C30H52N2O0P0S4Cl0 | 1.0 |
| 148.0052 | 148.0052 |  | 1.0 |
| 600.5115 | 600.5115 | C39H68N0O4P0S0Cl0 | 1.0 |
| 159.3128 | 159.3128 |  | 1.0 |
| 266.1882 | 266.1882 | C16H26N0O3P0S0Cl0 | 1.0 |
| 317.1107 | 317.1107 | C13H19N1O8P0S0Cl0 | 1.0 |
| 246.0781 | 246.0781 |  | 1.0 |
| 580.3657 | 580.3657 | C29H58N0O7P2S0Cl0 | 1.0 |
| 230.1092 | 230.1092 | C10H18N2O2P0S1Cl0 | 1.0 |
| 290.1043 | 290.1043 | C10H18N4O4P0S1Cl0 | 1.0 |
| 400.2013 | 400.2013 | C23H24N6O1P0S0Cl0 (not found . . . ) | 1.0 |
| 410.0904 | 410.0904 | C17H22N4O2P0S3Cl0 | 1.0 |
| 673.2580 | 673.2580 | C21H47N13O2P0S5Cl0 | 1.0 |
| 274.1090 | 274.1090 |  | 1.0 |
| 195.9984 | 195.9984 |  | 1.0 |
| 384.3239 | 384.3239 | C23H44N0O4P0S0Cl0 | 1.0 |
| 347.0932 | 347.0932 |  | 1.0 |
| 281.2719 | 281.2719 | C18H35N1O1P0S0Cl0 | 1.0 |
| 396.0923 | 396.0923 | C11H24N0O13P0S1Cl0 | 1.0 |
| 292.0834 | 292.0834 |  | 1.0 |
| 334.3240 | 334.3240 | C23H42N0O1P0S0Cl0 | 1.0 |
| 386.0800 | 386.0800 | C13H23N0O9P1S1Cl0 | 1.0 |
| 297.0051 | 297.0051 | C10H7N3O6P0S1Cl0 | 1.0 |
| 342.1161 | 342.1161 | C12H22N0O11P0S0Cl0 | 1.0 |
| 288.9626 | 288.9626 |  | 1.0 |
| 312.2819 | 312.2819 | C23H36N0O0P0S0Cl0 | 1.0 |
| 907.7733 | 907.7733 | C57H101N3O5P0S0Cl0 | 1.0 |
| 750.1210 | 750.1210 | C33H27N4O15P1S0Cl0 | 1.0 |
| 472.0817 | 472.0817 | C17H21N4O8P1S1Cl0 | 1.0 |
| 126.0231 | 126.0231 |  | 1.0 |
| 140.1175 | 140.1175 |  | 1.0 |
| 155.3174 | 155.3174 |  | 1.0 |
| 155.3207 | 155.3207 |  | 1.0 |
| 158.0518 | 158.0518 |  | 1.0 |
| 170.0345 | 170.0345 | C4H11N0O5P1S0Cl0 (4-hydroxybutyl phosphate) | 1.0 |
| 174.0529 | 174.0529 | C7H10N0O5P0S0Cl0 | 1.0 |
| 176.0536 | 176.0536 |  | 1.0 |
| 180.1151 | 180.1151 | C11H16N0O2P0S0Cl0)Adamantane-2-carboxylic acid;p-(pentyloxy)phenol;m-Pentyloxyphenol;Benzene,(4-methoxybutoxy)-;;Benzene, 1-butoxy-4-methoxy-;Butylated hydroxyanisole;4-pentyl-1,2-benzenediol) | 1.0 |
| 180.1516 | 180.1516 | C12H20N0O1P0S0Cl0 (trans,cis-2,6-Dodecadien-1-al trans,trans-24-Dodecadienal 2-Cyclohexylcyclohexanone Furan, 2,5-bis(1,1-dimethylethyl)-1-Adamantaneethanol) | 1.0 |
| 187.0015 | 187.0015 |  | 1.0 |
| 206.0429 | 206.0429 | C7H10N0O7P0S0Cl0 | 1.0 |
| 211.9723 | 211.9723 | C4H5N0O8P1S0Cl0 | 1.0 |
| 211.9724 | 211.9724 | C4H5N0O8P1S0Cl0 | 1.0 |
| 212.1414 | 212.1414 | C12H20N0O3P0S0Cl0 | 1.0 |
| 213.0827 | 213.0827 | C10H15N1O2P0S1Cl0 | 1.0 |
| 226.1568 | 226.1568 | C13H22N0O3P0S0Cl0 | 1.0 |
| 228.0245 | 228.0245 | C13H8N0O2P0S1Cl0 | 1.0 |
| 228.0246 | 228.0246 | C13H8N0O2P0S1Cl0 | 1.0 |
| 228.1362 | 228.1362 | C12H20N0O4P0S0Cl0 | 1.0 |
| 230.0193 | 230.0193 | C5H11N0O8P1S0Cl0 | 1.0 |
| 233.9541 | 233.9541 |  | 1.0 |
| 234.1229 | 234.1229 | C10H14N6O1P0S0Cl0(4-(5-amino-1,2,4-triazol-3-yl)-N-(2-methoxyethyl)-2-pyridineamine) | 1.0 |
| 239.3323 | 239.3323 |  | 1.0 |
| 239.3330 | 239.3330 |  | 1.0 |
| 246.0506 | 246.0506 | C6H15N0O8P1S0Cl0 | 1.0 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 249.9282 | 249.9282 | C2H4N0O10P2S0Cl0 (not found) | 1.0 |
| 250.0969 | 250.0969 | C10H19N0O5P1S0Cl0 (Triethyl 2-phosphonocrotonate;Triethyl 4-phosphonocrotonate) | 1.0 |
| 253.1331 | 253.1331 | C14H15N5O0P0S0Cl0 | 1.0 |
| 254.1000 | 254.1000 | C9H18N0O8P0S0Cl0 | 1.0 |
| 254.1001 | 254.1001 | C9H18N0O8P0S0Cl0 | 1.0 |
| 256.1263 | 256.1263 | | 1.0 |
| 257.1030 | 257.1030 | | 1.0 |
| 257.9778 | 257.9778 | C5H7N0O10P1S0Cl0 | 1.0 |
| 260.0021 | 260.0021 | C8H9N2O4P1S1Cl0 (not found) | 1.0 |
| 262.0005 | 262.0005 | C8H3N6O3P1S0Cl0 | 1.0 |
| 262.0455 | 262.0455 | C6H15N0O9P1S0Cl0 | 1.0 |
| 264.9191 | 264.9191 | | 1.0 |
| 266.1552 | 266.1552 | C12H26N0O4P0S1Cl0 | 1.0 |
| 266.8751 | 266.8751 | | 1.0 |
| 268.8734 | 268.8734 | | 1.0 |
| 268.8738 | 268.8738 | | 1.0 |
| 272.1177 | 272.1177 | C13H21N0O4P1S0Cl0 | 1.0 |
| 272.1780 | 272.1780 | C11H24N6O0P0S1Cl0 | 1.0 |
| 274.1938 | 274.1938 | C18H26N0O2P0S0Cl0 (Citronellyl phenylacetate;1-Menthyl phenylacetate;17beta-Hydroxyestra-4-en-3-one;Methyl-4-(1-methylethyl)-2-((2-methylphenyl)methoxy)-7-oxabicyclo[2.2.1]heptane Cinmethylin) | 1.0 |
| 276.0160 | 276.0160 | C7H16N0O5P0S3Cl0 | 1.0 |
| 276.0725 | 276.0725 | C17H12N2O0P0S1Cl0 | 1.0 |
| 276.0819 | 276.0819 | C15H16N0O3P0S1Cl0 | 1.0 |
| 276.0821 | 276.0821 | C15H16N0O3P0S1Cl0 | 1.0 |
| 276.2090 | 276.2090 | C18H28N0O2P0S0Cl0 | 1.0 |
| 276.2094 | 276.2094 | C18H28N0O2P0S0Cl0 | 1.0 |
| 276.2457 | 276.2457 | C19H32N0O1P0S0Cl0 | 1.0 |
| 277.2166 | 277.2166 | | 1.0 |
| 278.2244 | 278.2244 | C18H30N0O2P0S0Cl0 (9,12,15-Octadecatrienoic acid;4-n-Dodecylresorcinol;all cis-Delta-9,12,15-octadecatrienoate;Gamolenic acid; (Z)-13-Hexadecen-11-yn-1-ol acetate; (E,E,Z)-4,6,10-Hexadecatrienyl acetate) | 1.0 |
| 278.2246 | 278.2246 | C18H30N0O2P0S0Cl0 | 1.0 |
| 281.2720 | 281.2720 | C18H35N1O1P0S0Cl0 | 1.0 |
| 284.0447 | 284.0447 | C12H13N0O6P1S0Cl0 | 1.0 |
| 289.9954 | 289.9954 | C9H3N6O4P1S0Cl0 | 1.0 |
| 290.2250 | 290.2250 | C19H30N0O2P0S0Cl0 | 1.0 |
| 290.2613 | 290.2613 | C20H34N0O1P0S0Cl0 | 1.0 |
| 292.0558 | 292.0558 | C18H12N0O2P0S1Cl0 | 1.0 |
| 292.0560 | 292.0560 | C7H17N0O10P1S0Cl0 | 1.0 |
| 292.2036 | 292.2036 | C18H28N0O3P0S0Cl0 | 1.0 |
| 293.1577 | 293.1577 | | 1.0 |
| 294.0259 | 294.0259 | C6H14N0O11P0S1Cl0 (not found . . . ) | 1.0 |
| 294.0539 | 294.0539 | C18H14N0O0P0S2Cl0 (M-bis(phenylthio)benzene) | 1.0 |
| 294.2193 | 294.2193 | C18H30N0O3P0S0Cl0 (tetradecenyl succinic anhydride 9-OxoODE 13-OxoODE;13(S)-HOTrE;;(9Z)-(13S)-12,13-Epoxyoctadeca-9,11-dienoate) | 1.0 |
| 294.2193 | 294.2193 | C18H30N0O3P0S0Cl0 | 1.0 |
| 295.2511 | 295.2511 | C18H33N1O2P0S0Cl0 | 1.0 |
| 296.1387 | 296.1387 | C15H16N6O1P0S0Cl0 (Amicarbalide) | 1.0 |
| 300.1052 | 300.1052 | C10H20N0O10P0S0Cl0 | 1.0 |
| 300.1055 | 300.1055 | C10H20N0O10P0S0Cl0 | 1.0 |
| 300.2067 | 300.2067 | C16H24N6O0P0S0Cl0(5-(3,5-bis(dimethylamino)-4-methylbenzyl)-2,4-diaminopyrimidine) | 1.0 |
| 306.2557 | 306.2557 | C20H34N0O2P0S0Cl0 | 1.0 |
| 306.2562 | 306.2562 | C20H34N0O2P0S0Cl0 | 1.0 |
| 307.2511 | 307.2511 | C19H33N1O2P0S0Cl0 | 1.0 |
| 308.0321 | 308.0321 | C10H16N2O3P0S3Cl0 | 1.0 |
| 308.1060 | 308.1060 | C12H16N6O2P0S1Cl0 | 1.0 |
| 310.2143 | 310.2143 | C18H30N0O4P0S0Cl0 | 1.0 |
| 312.0608 | 312.0608 | C13H8N6O4P0S0Cl0 (not found . . . ) | 1.0 |
| 312.2461 | 312.2461 | | 1.0 |
| 315.1315 | 315.1315 | C14H21N1O7P0S0Cl0 | 1.0 |
| 315.1318 | 315.1318 | C14H21N1O7P0S0Cl0 | 1.0 |
| 316.1680 | 316.1680 | C12H24N6O2P0S1Cl0 | 1.0 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 316.1800 | 316.1800 | C16H29N0O4P1S0Cl0 | 1.0 |
| 316.1806 | 316.1806 | C16H29N0O4P1S0Cl0 | 1.0 |
| 321.2300 | 321.2300 | C19H31N1O3P0S0Cl0 | 1.0 |
| 322.0209 | 322.0209 | C10H15N2O4P1S2Cl0 | 1.0 |
| 324.2297 | 324.2297 | C19H32N0O4P0S0Cl0 | 1.0 |
| 325.2247 | 325.2247 |  | 1.0 |
| 326.0851 | 326.0851 | C11H18N0O11P0S0Cl0 (not found . . . ) | 1.0 |
| 326.2275 | 326.2275 | C19H34N0O2P0S1Cl0 | 1.0 |
| 328.0464 | 328.0464 | C10H16N0O10P0S1Cl0 (not found . . . ) | 1.0 |
| 328.2246 | 328.2246 | C18H32N0O5P0S0Cl0 | 1.0 |
| 332.1759 | 332.1759 |  | 1.0 |
| 334.2509 | 334.2509 | C21H34N0O3P0S0Cl0 | 1.0 |
| 338.0519 | 338.0519 | C8H18N0O12P0S1Cl0 | 1.0 |
| 344.8990 | 344.8990 | C10H4N1O5P1S3Cl0 | 1.0 |
| 346.2116 | 346.2116 | C17H26N6O2P0S0Cl0 | 1.0 |
| 354.0944 | 354.0944 | C10H19N4O8P1S0Cl0 | 1.0 |
| 354.0946 | 354.0946 | C11H23N4O3P1S2Cl0 (not found) | 1.0 |
| 354.0947 | 354.0947 | C11H23N4O3P1S2Cl0 | 1.0 |
| 354.1994 | 354.1994 | C16H35N0O4P1S1Cl0 | 1.0 |
| 360.9461 | 360.9461 | C6H19N1O2P0S7Cl0 | 1.0 |
| 360.9695 | 360.9695 |  | 1.0 |
| 362.1334 | 362.1334 | C15H26N2O4P0S2Cl0 (not found) | 1.0 |
| 362.1773 | 362.1773 | C18H34N0O1P0S3Cl0 | 1.0 |
| 362.1852 | 362.1852 | C20H30N2O0P0S2Cl0 | 1.0 |
| 362.2065 | 362.2065 | C17H26N6O3P0S0Cl0 | 1.0 |
| 368.1097 | 368.1097 | C11H21N4O8P1S0Cl0 | 1.0 |
| 368.1106 | 368.1106 | C12H25N4O3P1S2Cl0 | 1.0 |
| 374.2433 | 374.2433 | C19H30N6O2P0S0Cl0 | 1.0 |
| 376.0772 | 376.0772 | C15H24N2O1P0S4Cl0 | 1.0 |
| 376.0772 | 376.0772 | C15H24N2O1P0S4Cl0 | 1.0 |
| 378.0923 | 378.0923 | C14H14N6O7P0S0Cl0 | 1.0 |
| 380.0708 | 380.0708 | C15H17N4O4P1S1Cl0 | 1.0 |
| 380.0709 | 380.0709 | C15H17N4O4P1S1Cl0 | 1.0 |
| 380.2147 | 380.2147 | C13H24N12O2P0S0Cl0 | 1.0 |
| 382.0696 | 382.0696 | C13H14N6O6P0S1Cl0 | 1.0 |
| 382.0703 | 382.0703 | C14H18N6O1P0S3Cl0 | 1.0 |
| 384.0676 | 384.0676 | C21H20N0O1P0S3Cl0 | 1.0 |
| 384.0678 | 384.0678 | C10H25N0O9P1S2Cl0 | 1.0 |
| 384.1181 | 384.1181 | C17H16N6O5P0S0Cl0 | 1.0 |
| 384.1548 | 384.1548 | C26H24N0O1P0S1Cl0 | 1.0 |
| 385.9791 | 385.9791 | C10H10N0O14P0S1Cl0 (not found . . . ) | 1.0 |
| 385.9800 | 385.9800 | C11H14N0O9P0S3Cl0 | 1.0 |
| 386.1856 | 386.1856 | C22H22N6O1P0S0Cl0 | 1.0 |
| 392.0352 | 392.0352 | C13H8N6O9P0S0Cl0 | 1.0 |
| 392.0507 | 392.0507 | C10H16N8O3P0S3Cl0 | 1.0 |
| 392.0512 | 392.0512 | C9H14N8O6P2S0Cl0 | 1.0 |
| 392.2241 | 392.2241 | C20H40N0O1P0S3Cl0 | 1.0 |
| 396.3512 | 396.3512 |  | 1.0 |
| 396.3765 | 396.3765 |  | 1.0 |
| 403.2167 | 403.2167 |  | 1.0 |
| 403.9897 | 403.9897 | C10H12N0O15P0S1Cl0 | 1.0 |
| 404.1235 | 404.1235 | C13H24N8O1P0S3Cl0 | 1.0 |
| 405.1569 | 405.1569 | C16H27N3O7P0S1Cl0 | 1.0 |
| 405.1571 | 405.1571 | C16H27N3O7P0S1Cl0 | 1.0 |
| 406.0508 | 406.0508 | C14H10N6O9P0S0Cl0 | 1.0 |
| 406.0516 | 406.0516 | C14H20N2O6P2S1Cl0 | 1.0 |
| 406.2710 | 406.2710 | C18H39N4O4P1S0Cl0 | 1.0 |
| 408.0090 | 408.0090 | C9H20N4O4P0S5Cl0 | 1.0 |
| 408.0094 | 408.0094 | C13H13N0O13P1S0Cl0 | 1.0 |
| 408.2180 | 408.2180 | C21H33N2O4P1S0Cl0 | 1.0 |
| 410.0899 | 410.0899 | C17H30N0O1P0S5Cl0 | 1.0 |
| 414.2449 | 414.2449 | C23H42N0O0P0S3Cl0 | 1.0 |
| 416.1526 | 416.1526 | C13H24N10O2P0S2Cl0 | 1.0 |
| 416.1530 | 416.1530 | C15H28N0O13P0S0Cl0 | 1.0 |
| 416.1683 | 416.1683 | C19H28N0O10P0S0Cl0 (not found . . . ) | 1.0 |
| 418.0052 | 418.0052 | C17H14N4O1P0S4Cl0 | 1.0 |
| 418.9754 | 418.9754 | C14H9N7O1P1S4Cl0 | 1.0 |
| 420.3395 | 420.3395 | C30H44N0O1P0S0Cl0 | 1.0 |
| 422.0247 | 422.0247 | C9H20N4O7P2S2Cl0 | 1.0 |
| 424.0615 | 424.0615 | C14H12N6O10P0S0Cl0 | 1.0 |
| 428.3654 | 428.3654 | C29H48N0O2P0S0Cl0 | 1.0 |
| 430.0895 | 430.0895 | C16H31N0O3P1S4Cl0 | 1.0 |
| 430.0903 | 430.0903 | C16H15N8O5P1S0Cl0 | 1.0 |
| 430.0904 | 430.0904 | C16H15N8O5P1S0Cl0 | 1.0 |
| 430.0904 | 430.0904 | C16H15N8O5P1S0Cl0 | 1.0 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 438.0465 | 438.0465 | C17H15N2O10P1S0Cl0 (not found . . . ) | 1.0 |
| 438.0477 | 438.0477 | C16H22N0O8P0S3Cl0 | 1.0 |
| 438.1342 | 438.1342 | C13H30N2O10P0S2Cl0 | 1.0 |
| 438.1355 | 438.1355 | C14H26N6O6P0S2Cl0 | 1.0 |
| 438.1566 | 438.1566 | C19H34N0O5P0S3Cl0 | 1.0 |
| 438.1577 | 438.1577 | C20H38N0O0P0S5Cl0 | 1.0 |
| 438.3504 | 438.3504 | C23H46N6O0P0S1Cl0 | 1.0 |
| 438.5084 | 438.5084 |  | 1.0 |
| 440.0166 | 440.0166 | C19H13N4O3P1S2Cl0 | 1.0 |
| 440.0924 | 440.0924 | C15H24N2O9P0S2Cl0 | 1.0 |
| 446.1975 | 446.1975 | C21H34N0O8P0S1Cl0 | 1.0 |
| 448.0989 | 448.0989 | C26H24N0O1P0S3Cl0 | 1.0 |
| 448.0993 | 448.0993 | C18H12N10O5P0S0Cl0 | 1.0 |
| 448.1002 | 448.1002 | C19H16N10O0P0S2Cl0 | 1.0 |
| 448.1013 | 448.1013 | C22H24N0O6P0S2Cl0 | 1.0 |
| 448.5007 | 448.5007 | C32H64N0O0P0S0Cl0 | 1.0 |
| 449.1923 | 449.1923 | C21H23N9O3P0S0Cl0 | 1.0 |
| 450.9646 | 450.9646 | C14H17N3O2P0S6Cl0 | 1.0 |
| 454.0056 | 454.0056 | C9H11N8O10P1S1Cl0 | 1.0 |
| 454.0061 | 454.0061 | C15H18N0O10P0S3Cl0 | 1.0 |
| 454.1085 | 454.1085 | C16H18N6O10P0S0Cl0 | 1.0 |
| 454.1090 | 454.1090 | C17H30N2O4P0S4Cl0 | 1.0 |
| 455.4621 | 455.4621 |  | 1.0 |
| 458.3142 | 458.3142 | C27H42N2O4P0S0Cl0 | 1.0 |
| 458.9844 | 458.9844 | C8H10N7O12P1S1Cl0 | 1.0 |
| 460.2862 | 460.2862 | C24H44N0O6P0S1Cl0 | 1.0 |
| 462.0316 | 462.0316 | C13H18N0O16P0S1Cl0 | 1.0 |
| 462.1569 | 462.1569 | C23H23N6O3P1S0Cl0 | 1.0 |
| 464.0332 | 464.0332 | C9H22N0O17P2S0Cl0 | 1.0 |
| 466.0626 | 466.0626 | C19H22N4O2P0S4Cl0 (not found . . . ) | 1.0 |
| 466.0630 | 466.0630 | C19H14N8O3P0S2Cl0 | 1.0 |
| 466.1959 | 466.1959 | C15H30N8O7P0S1Cl0 | 1.0 |
| 470.0807 | 470.0807 | C21H19N4O5P1S1Cl0 | 1.0 |
| 480.2379 | 480.2379 | C19H32N10O3P0S1Cl0 | 1.0 |
| 482.2650 | 482.2650 | C18H34N12O2P0S1Cl0 | 1.0 |
| 484.0524 | 484.0524 | C16H20N0O15P0S1Cl0 | 1.0 |
| 486.1647 | 486.1647 | C25H30N2O4P0S2Cl0 | 1.0 |
| 486.1861 | 486.1861 | C22H26N6O7P0S0Cl0 | 1.0 |
| 490.1871 | 490.1871 | C17H39N4O4P1S3Cl0 | 1.0 |
| 490.2899 | 490.2899 | C24H46N2O4P0S2Cl0 | 1.0 |
| 494.1151 | 494.1151 | C18H30N4O4P0S4Cl0 | 1.0 |
| 494.1171 | 494.1171 | C16H27N6O6P1S2Cl0 | 1.0 |
| 496.2353 | 496.2353 | C25H33N6O3P1S0Cl0 | 1.0 |
| 497.2528 | 497.2528 | C20H43N5O3P0S3Cl0 | 1.0 |
| 497.3192 | 497.3192 | C28H43N5O1P0S1Cl0 | 1.0 |
| 500.0785 | 500.0785 | C25H24N0O5P0S3Cl0 | 1.0 |
| 500.1049 | 500.1049 | C20H20N8O4P0S2Cl0 | 1.0 |
| 500.1056 | 500.1056 | C15H32N0O12P0S3Cl0 | 1.0 |
| 502.2512 | 502.2512 | C20H30N12O4P0S0Cl0 | 1.0 |
| 504.1689 | 504.1689 | C16H20N14O6P0S0Cl0 | 1.0 |
| 505.0372 | 505.0372 | C9H24N5O11P1S3Cl0 | 1.0 |
| 506.3214 | 506.3214 | C25H50N2O4P0S2Cl0 | 1.0 |
| 508.1998 | 508.1998 | C31H28N2O5P0S0Cl0 | 1.0 |
| 508.9496 | 508.9496 | C12H15N9O0P0S7Cl0 | 1.0 |
| 511.9206 | 511.9206 | C8H11N4O14P3S1Cl0 | 1.0 |
| 514.3131 | 514.3131 | C32H42N4O0P0S1Cl0 | 1.0 |
| 516.0377 | 516.0377 | C13H17N4O16P1S0Cl0 | 1.0 |
| 516.1212 | 516.1212 | C14H33N2O12P1S2Cl0 | 1.0 |
| 516.1313 | 516.1313 | C15H20N10O11P0S0Cl0 | 1.0 |
| 517.3165 | 517.3165 | C29H39N7O2P0S0Cl0 | 1.0 |
| 518.3373 | 518.3373 | C27H51N0O7P1S0Cl0 | 1.0 |
| 518.3806 | 518.3806 | C25H46N10O2P0S0Cl0 | 1.0 |
| 518.6585 | 518.6585 |  | 1.0 |
| 519.0544 | 519.0544 | C19H26N3O4P1S4Cl0 | 1.0 |
| 522.0794 | 522.0794 | C13H19N10O9P1S1Cl0 | 1.0 |
| 526.0587 | 526.0587 | C27H26N0O1P0S5Cl0 | 1.0 |
| 526.1501 | 526.1501 | C16H34N2O13P0S2Cl0 | 1.0 |
| 526.1513 | 526.1513 | C17H30N6O9P0S2Cl0 | 1.0 |
| 532.0407 | 532.0407 | C8H21N8O13P1S2Cl0 | 1.0 |
| 532.3430 | 532.3430 | C30H49N2O4P1S0Cl0 | 1.0 |
| 534.0481 | 534.0481 | C23H20N0O11P2S0Cl0 | 1.0 |
| 534.2643 | 534.2643 | C21H46N2O9P0S2Cl0 | 1.0 |
| 535.0498 | 535.0498 | C19H18N7O6P1S2Cl0 | 1.0 |
| 536.4377 | 536.4377 | C32H60N2O2P0S1Cl0 | 1.0 |
| 537.6879 | 537.6879 |  | 1.0 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 538.1139 | 538.1139 | C19H39N0O5P1S5Cl0 | 1.0 |
| 539.2980 | 539.2980 | C24H50N3O4P1S2Cl0 | 1.0 |
| 540.0544 | 540.0544 | C13H21N10O6P1S3Cl0 | 1.0 |
| 540.0986 | 540.0986 | C14H32N6O6P0S5Cl0 | 1.0 |
| 540.1016 | 540.1016 | C25H20N2O12P0S0Cl0 | 1.0 |
| 541.3141 | 541.3141 | C24H44N7O5P1S0Cl0 | 1.0 |
| 544.1495 | 544.1495 | C14H30N10O7P2S1Cl0 | 1.0 |
| 545.0913 | 545.0913 | C15H29N1O16P1S0Cl0 | 1.0 |
| 547.0892 | 547.0892 | C21H17N13O0P0S3Cl0 | 1.0 |
| 550.1741 | 550.1741 | C24H40N0O6P2S2Cl0 | 1.0 |
| 550.4174 | 550.4174 | C40H54N0O1P0S0Cl0 | 1.0 |
| 556.1108 | 556.1108 | C23H21N6O9P1S0Cl0 | 1.0 |
| 558.3441 | 558.3441 | C26H54N0O10P0S1Cl0 | 1.0 |
| 559.9958 | 559.9958 | C9H24N2O17P0S4Cl0 | 1.0 |
| 560.1518 | 560.1518 | C16H34N8O6P2S2Cl0 | 1.0 |
| 560.1518 | 560.1518 | C17H28N12O4P0S3Cl0 | 1.0 |
| 560.1527 | 560.1527 | C16H26N12O7P2S0Cl0 | 1.0 |
| 560.1536 | 560.1536 | C19H34N2O13P2S0Cl0 | 1.0 |
| 565.3373 | 565.3373 | C30H51N3O3P0S2Cl0 | 1.0 |
| 566.0584 | 566.0584 | C12H28N2O17P2S1Cl0 | 1.0 |
| 566.1429 | 566.1429 | C32H27N2O4P1S1Cl0 | 1.0 |
| 572.3018 | 572.3018 | C24H53N4O3P1S3Cl0 | 1.0 |
| 572.3028 | 572.3028 | C30H52N0O4P0S3Cl0 | 1.0 |
| 575.1639 | 575.1639 | C27H29N1O13P0S0Cl0 | 1.0 |
| 575.1639 | 575.1639 | C27H29N1O13P0S0Cl0 | 1.0 |
| 576.1456 | 576.1456 | C19H17N18O3P1S0Cl0 (not found . . . ) | 1.0 |
| 576.1477 | 576.1477 | C22H33N4O8P1S2Cl0 | 1.0 |
| 578.1629 | 578.1629 | C16H28N12O8P2S0Cl0 | 1.0 |
| 578.1633 | 578.1633 | C18H34N12O0P0S5Cl0 | 1.0 |
| 578.1636 | 578.1636 | C27H30N0O14P0S0Cl0 | 1.0 |
| 578.1638 | 578.1638 | C20H38N2O11P0S3Cl0 | 1.0 |
| 581.3681 | 581.3681 | C25H48N11O3P1S0Cl0 | 1.0 |
| 582.0160 | 582.0160 | C24H24N0O7P2S3Cl0 | 1.0 |
| 582.0169 | 582.0169 | C26H22N4O0P0S6Cl0 | 1.0 |
| 582.3236 | 582.3236 | C32H54N0O3P0S3Cl0 | 1.0 |
| 585.4471 | 585.4471 | C31H63N5O1P0S2Cl0 | 1.0 |
| 590.4909 | 590.4909 | C37H66N0O5P0S0Cl0 | 1.0 |
| 592.2687 | 592.2687 | C20H40N12O5P0S2Cl0 | 1.0 |
| 594.1582 | 594.1582 | C33H30N4O1P0S3Cl0 | 1.0 |
| 594.3820 | 594.3820 | C39H50N2O3P0S0Cl0 | 1.0 |
| 594.3957 | 594.3957 | C34H58N0O6P0S1Cl0 | 1.0 |
| 594.4660 | 594.4660 | C39H62N0O4P0S0Cl0 | 1.0 |
| 595.1622 | 595.1622 | C22H45N1O5P0S6Cl0 | 1.0 |
| 595.1624 | 595.1624 | C29H29N3O9P0S1Cl0 | 1.0 |
| 596.2239 | 596.2239 | C29H36N6O4P0S2Cl0 | 1.0 |
| 598.1296 | 598.1296 | C28H31N4O3P1S3Cl0 | 1.0 |
| 598.1297 | 598.1297 | C17H36N4O11P2S2Cl0 | 1.0 |
| 598.4025 | 598.4025 | C30H63N0O7P1S1Cl0 | 1.0 |
| 600.3999 | 600.3999 | C32H52N6O5P0S0Cl0 (not found . . . ) | 1.0 |
| 602.1432 | 602.1432 | C14H31N6O18P1S0Cl0 | 1.0 |
| 602.1433 | 602.1433 | C17H40N4O9P2S3Cl0 | 1.0 |
| 602.5277 | 602.5277 | C39H70N0O4P0S0Cl0 | 1.0 |
| 607.2877 | 607.2877 | C27H50N3O6P1S2Cl0 | 1.0 |
| 607.2880 | 607.2880 | C27H53N5O0P0S5Cl0 | 1.0 |
| 608.1736 | 608.1736 | C25H34N6O6P2S1Cl0 | 1.0 |
| 608.1737 | 608.1737 | C26H28N10O4P0S2Cl0 | 1.0 |
| 608.1741 | 608.1741 | C26H20N14O5P0S0Cl0 | 1.0 |
| 608.1742 | 608.1742 | C28H32N0O15P0S0Cl0 | 1.0 |
| 610.1523 | 610.1523 | C19H19N18O5P1S0Cl0 | 1.0 |
| 610.1526 | 610.1526 | C33H38N0O1P0S5Cl0 | 1.0 |
| 610.1531 | 610.1531 | C18H34N12O2P0S5Cl0 | 1.0 |
| 610.1533 | 610.1533 | C27H30N0O16P0S0Cl0 | 1.0 |
| 611.2668 | 611.2668 | C25H49N5O4P0S4Cl0 | 1.0 |
| 612.1455 | 612.1455 | C23H33N0O17P1S0Cl0 | 1.0 |
| 612.1508 | 612.1508 | C25H28N10O3P0S3Cl0 | 1.0 |
| 612.4750 | 612.4750 | C39H64N0O5P0S0Cl0 | 1.0 |
| 612.7685 | 612.7685 | C9H12N1O10P1S9Cl0 | 1.0 |
| 614.1023 | 614.1023 | C22H19N10O10P1S0Cl0 | 1.0 |
| 614.1032 | 614.1032 | C23H23N10O5P1S2Cl0 | 1.0 |
| 614.1041 | 614.1041 | C21H18N12O9P0S1Cl0 | 1.0 |
| 614.3496 | 614.3496 | C25H54N6O7P0S2Cl0 | 1.0 |
| 615.1687 | 615.1687 | C25H21N13O7P0S0Cl0 | 1.0 |
| 616.1138 | 616.1138 | C27H22N8O6P2S0Cl0 | 1.0 |
| 616.1404 | 616.1404 | C18H32N8O10P0S3Cl0 | 1.0 |
| 616.1602 | 616.1602 | C16H29N10O14P1S0Cl0 | 1.0 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 616.1603 | 616.1603 | C27H24N10O6P0S1Cl0 | 1.0 |
| 618.2733 | 618.2733 | C24H54N6O0P0S6Cl0 | 1.0 |
| 620.6472 | 620.6472 | C42H84N0O2P0S0Cl0 | 1.0 |
| 624.1681 | 624.1681 | C26H36N6O4P0S4Cl0 | 1.0 |
| 625.2717 | 625.2717 | C27H43N7O6P0S2Cl0 | 1.0 |
| 626.4080 | 626.4080 | C33H54N8O2P0S1Cl0 | 1.0 |
| 628.1163 | 628.1163 | C26H36N4O2P0S6Cl0 | 1.0 |
| 630.1349 | 630.1349 | C22H30N8O8P0S3Cl0 | 1.0 |
| 632.1361 | 632.1361 | C19H36N8O6P0S5Cl0 | 1.0 |
| 633.1029 | 633.1029 | C19H27N11O6P0S4Cl0 (not found . . . ) | 1.0 |
| 634.1695 | 634.1695 | C19H38N8O8P0S4Cl0 | 1.0 |
| 634.1696 | 634.1696 | C19H38N8O8P0S4Cl0 | 1.0 |
| 638.1203 | 638.1203 | C17H27N12O9P1S2Cl0 | 1.0 |
| 646.1289 | 646.1289 | C21H26N8O14P0S1Cl0 | 1.0 |
| 646.1289 | 646.1289 | C21H26N8O14P0S1Cl0 | 1.0 |
| 647.1534 | 647.1534 | C30H38N3O3P1S4Cl0 | 1.0 |
| 648.1850 | 648.1850 | C27H32N6O11P0S1Cl0 | 1.0 |
| 648.1852 | 648.1852 | C20H40N8O8P0S4Cl0 | 1.0 |
| 648.6784 | 648.6784 | C44H88N0O2P0S0Cl0 | 1.0 |
| 655.0629 | 655.0629 | C20H25N13O1P0S6Cl0 | 1.0 |
| 655.2457 | 655.2457 | C35H45N1O5P0S3Cl0 | 1.0 |
| 658.1049 | 658.1049 | C14H34N12O6P0S6Cl0 | 1.0 |
| 658.4452 | 658.4452 | C32H62N6O6P0S1Cl0 | 1.0 |
| 660.0968 | 660.0968 | C18H17N18O7P1S1Cl0 | 1.0 |
| 660.0994 | 660.0994 | C16H28N12O9P0S4Cl0 | 1.0 |
| 660.1081 | 660.1081 | C20H30N4O17P2S0Cl0 | 1.0 |
| 660.1243 | 660.1243 | C26H28N8O7P0S3Cl0 | 1.0 |
| 660.4804 | 660.4804 | C41H64N4O1P0S1Cl0 | 1.0 |
| 662.1452 | 662.1452 | C29H43N0O5P1S5Cl0 | 1.0 |
| 663.9939 | 663.9939 | C16H18N4O21P2S0Cl0 | 1.0 |
| 664.4181 | 664.4181 | C27H52N16O2P0S1Cl0 | 1.0 |
| 675.2554 | 675.2554 | C24H54N1O12P1S3Cl0 | 1.0 |
| 675.2584 | 675.2584 | C32H37N9O6P0S1Cl0 | 1.0 |
| 675.8492 | 675.8492 | C14H8N14O1P0S9Cl0 | 1.0 |
| 676.3514 | 676.3514 | C35H56N4O3P0S3Cl0 | 1.0 |
| 676.3663 | 676.3663 | C23H48N16O6P0S1Cl0 | 1.0 |
| 676.7106 | 676.7106 | C46H92N0O2P0S0Cl0 | 1.0 |
| 677.1019 | 677.1019 | C23H19N17O3P0S3Cl0 | 1.0 |
| 678.1100 | 678.1100 | C18H26N6O22P0S0Cl0 | 1.0 |
| 678.1106 | 678.1106 | C29H31N2O11P1S2Cl0 (not found . . . ) | 1.0 |
| 684.2320 | 684.2320 | C29H50N0O10P2S2Cl0 | 1.0 |
| 698.3486 | 698.3486 | C29H38N20O2P0S0Cl0 | 1.0 |
| 699.2660 | 699.2660 | C28H37N13O7P0S1Cl0 | 1.0 |
| 703.9985 | 703.9985 | C30H26N0O8P2S4Cl0 | 1.0 |
| 703.9990 | 703.9990 | C32H32N0O0P0S9Cl0 | 1.0 |
| 704.7397 | 704.7397 |  | 1.0 |
| 706.2120 | 706.2120 | C27H50N2O9P0S5Cl0 | 1.0 |
| 706.2146 | 706.2146 | C25H39N8O12P1S1Cl0 (not found . . . ) | 1.0 |
| 706.4470 | 706.4470 | C45H54N8O0P0S0Cl0 | 1.0 |
| 714.3221 | 714.3221 | C34H54N2O10P0S2Cl0 | 1.0 |
| 720.3297 | 720.3297 | C21H44N20O5P0S2Cl0 | 1.0 |
| 721.3397 | 721.3397 | C39H51N3O8P0S1Cl0 | 1.0 |
| 722.1876 | 722.1876 | C35H35N2O13P1S0Cl0 | 1.0 |
| 724.1248 | 724.1248 | C32H39N0O9P3S2Cl0 | 1.0 |
| 728.0922 | 728.0922 | C34H29N6O3P1S4Cl0 | 1.0 |
| 728.0943 | 728.0943 | C14H29N14O13P1S3Cl0 | 1.0 |
| 728.2546 | 728.2546 | C22H45N14O6P1S3Cl0 | 1.0 |
| 728.7483 | 728.7483 | C10H4N9O12P1S8Cl0 | 1.0 |
| 734.1382 | 734.1382 | C14H32N12O19P2S0Cl0 | 1.0 |
| 742.4759 | 742.4759 | C44H71N0O5P1S1Cl0 | 1.0 |
| 746.3782 | 746.3782 | C37H51N10O5P1S0Cl0 | 1.0 |
| 746.5438 | 746.5438 | C33H66N18O0P0S1Cl0 | 1.0 |
| 756.5185 | 756.5185 | C46H76N0O4P0S2Cl0 (not found . . . ) | 1.0 |
| 758.4214 | 758.4214 | C37H58N8O7P0S1Cl0 | 1.0 |
| 766.4533 | 766.4533 | C36H66N10O2P0S3Cl0 | 1.0 |
| 768.4794 | 768.4794 | C42H68N6O3P0S2Cl0 | 1.0 |
| 771.2292 | 771.2292 | C35H30N15O5P1S0Cl0 | 1.0 |
| 774.4484 | 774.4484 | C34H70N4O11P0S2Cl0 | 1.0 |
| 782.0988 | 782.0988 | C36H32N0O14P2S1Cl0 | 1.0 |
| 797.4404 | 797.4404 | C35H63N11O6P0S2Cl0 | 1.0 |
| 797.4559 | 797.4559 | C32H71N13O0P0S5Cl0 | 1.0 |
| 798.4592 | 798.4592 | C37H67N8O7P1S1Cl0 | 1.0 |
| 801.4637 | 801.4637 | C40H63N7O10P0S0Cl0 | 1.0 |
| 806.3376 | 806.3376 | C32H46N20O0P0S3Cl0 | 1.0 |
| 807.3395 | 807.3395 | C37H66N3O4P1S5Cl0 | 1.0 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 810.1663 | 810.1663 | C29H24N20O6P2S0Cl0 | 1.0 |
| 810.4979 | 810.4979 | C46H66N8O3P0S1Cl0 | 1.0 |
| 812.4055 | 812.4055 | C41H69N2O6P1S3Cl0 | 1.0 |
| 814.5673 | 814.5673 | C43H90N0O5P0S4Cl0 | 1.0 |
| 817.4587 | 817.4587 | C48H67N1O8P0S1Cl0 | 1.0 |
| 818.4467 | 818.4467 | C45H62N4O10P0S0Cl0 | 1.0 |
| 819.4522 | 819.4522 | C45H66N5O5P1S1Cl0 | 1.0 |
| 819.6629 | 819.6629 | C50H93N1O3P0S2Cl0 | 1.0 |
| 820.5246 | 820.5246 | C41H72N8O7P0S1Cl0 | 1.0 |
| 824.4714 | 824.4714 | C42H65N8O7P1S0Cl0 | 1.0 |
| 824.5328 | 824.5328 | C43H84N0O8P0S3Cl0 | 1.0 |
| 825.4681 | 825.4681 | C52H64N3O4P1S0Cl0 | 1.0 |
| 828.5103 | 828.5103 | C41H82N0O10P2S1Cl0 | 1.0 |
| 829.2248 | 829.2248 | C41H40N3O14P1S0Cl0 | 1.0 |
| 830.4188 | 830.4188 | C40H54N12O8P0S0Cl0 | 1.0 |
| 832.4560 | 832.4560 | C42H73N0O12P1S1Cl0 | 1.0 |
| 834.4760 | 834.4760 | C40H83N0O7P1S4Cl0 | 1.0 |
| 840.3420 | 840.3420 | C39H56N10O3P0S4Cl0 | 1.0 |
| 840.3420 | 840.3420 | C39H56N10O3P0S4Cl0 (not found) | 1.0 |
| 840.4363 | 840.4363 | C38H60N14O4P0S2Cl0 | 1.0 |
| 844.4991 | 844.4991 | C45H81N0O6P1S3Cl0 | 1.0 |
| 846.5042 | 846.5042 | C43H82N4O2P0S5Cl0 | 1.0 |
| 848.4246 | 848.4246 | C43H76N0O6P0S5Cl0 | 1.0 |
| 850.7077 | 850.7077 |  | 1.0 |
| 854.1818 | 854.1818 | C37H41N6O10P3S1Cl0 | 1.0 |
| 857.1747 | 857.1747 | C42H39N3O11P0S3Cl0 | 1.0 |
| 869.7488 | 869.7488 | C52H103N1O6P0S1Cl0 | 1.0 |
| 870.5704 | 870.5704 | C45H70N14O4P0S0Cl0 | 1.0 |
| 872.5740 | 872.5740 | C46H88N4O3P0S4Cl0 | 1.0 |
| 872.6919 | 872.6919 | C51H88N10O0P0S1Cl0 | 1.0 |
| 877.7280 | 877.7280 | C56H99N3O0P0S2Cl0 (not found...) | 1.0 |
| 879.4183 | 879.4183 | C45H62N5O11P1S0Cl0 | 1.0 |
| 879.7361 | 879.7361 | C46H93N11O5P0S0Cl0 (not found) | 1.0 |
| 881.7554 | 881.7554 | C59H99N3O0P0S1Cl0 | 1.0 |
| 883.7690 | 883.7690 | C47H93N15O1P0S0Cl0 | 1.0 |
| 884.3949 | 884.3949 | C38H61N8O14P1S0Cl0 | 1.0 |
| 885.4113 | 885.4113 | C34H63N9O16P0S1Cl0 | 1.0 |
| 886.5615 | 886.5615 | C48H82N6O3P0S3Cl0 | 1.0 |
| 900.3865 | 900.3865 | C48H49N14O3P1S0Cl0 | 1.0 |
| 900.8015 | 900.8015 | C56H108N4O0P0S2Cl0 | 1.0 |
| 908.4707 | 908.4707 | C42H84N0O10P0S5Cl0 | 1.0 |
| 908.7842 | 908.7842 | C60H108N0O1P0S2Cl0 | 1.0 |
| 910.8035 | 910.8035 | C57H106N4O2P0S1Cl0 | 1.0 |
| 911.7956 | 911.7956 | C59H101N5O2P0S0Cl0 | 1.0 |
| 912.5032 | 912.5032 | C42H72N8O12P0S1Cl0 | 1.0 |
| 913.4956 | 913.4956 | C41H73N9O10P2S0Cl0 | 1.0 |
| 913.5193 | 913.5193 | C38H80N11O6P1S3Cl0 | 1.0 |
| 913.8206 | 913.8206 | C57H107N3O5P0S0Cl0 | 1.0 |
| 921.7305 | 921.7305 | C10H20N6O18P6S7Cl0 | 1.0 |
| 926.5207 | 926.5207 | C41H76N12O6P2S1Cl0 | 1.0 |
| 928.5050 | 928.5050 | C51H73N6O6P1S1Cl0 | 1.0 |
| 936.5798 | 936.5798 | C55H86N0O8P2S0Cl0 | 1.0 |
| 940.8543 | 940.8543 | C56H108N8O3P0S0Cl0 | 1.0 |
| 941.4883 | 941.4883 | C44H76N7O9P1S2Cl0 | 1.0 |
| 941.4959 | 941.4959 | C48H75N7O6P0S3Cl0 | 1.0 |
| 942.5221 | 942.5221 | C44H90N6O1P0S7Cl0 | 1.0 |
| 942.5251 | 942.5251 | C40H82N10O7P0S4Cl0 | 1.0 |
| 942.5300 | 942.5300 | C45H66N16O7P0S0Cl0 | 1.0 |
| 944.5314 | 944.5314 | C65H72N2O2P0S1Cl0 | 1.0 |
| 944.5362 | 944.5362 | C50H88N0O8P0S4Cl0 | 1.0 |
| 950.4959 | 950.4959 | C39H75N12O9P1S2Cl0 | 1.0 |
| 956.4720 | 956.4720 | C44H76N8O7P0S4Cl0 | 1.0 |
| 958.5102 | 958.5102 | C44H67N18O3P1S1Cl0 | 1.0 |
| 959.5265 | 959.5265 | C40H70N19O5P1S1Cl0 | 1.0 |
| 962.4738 | 962.4738 | C38H66N20O4P0S3Cl0 | 1.0 |
| 963.4914 | 963.4914 | C47H78N7O6P1S3Cl0 | 1.0 |
| 965.4149 | 965.4149 | C33H63N11O22P0S0Cl0 | 1.0 |
| 965.4919 | 965.4919 | C48H75N3O15P0S1Cl0 | 1.0 |
| 965.4984 | 965.4984 | C49H75N1O18P0S0Cl0 | 1.0 |
| 965.8388 | 965.8388 | C22H18N10O16P0S9Cl0 | 1.0 |
| 970.4126 | 970.4126 | C39H58N18O8P0S2Cl0 | 1.0 |
| 971.4055 | 971.4055 | C46H58N11O11P1S0Cl0 | 1.0 |
| 972.5303 | 972.5303 | C50H84N0O14P0S2Cl0 | 1.0 |
| 972.5396 | 972.5396 | C40H69N20O7P1S0Cl0 | 1.0 |
| 980.4706 | 980.4706 | C45H69N14O5P1S2Cl0 | 1.0 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 981.4897 | 981.4897 | C43H75N13O5P0S4Cl0 | 1.0 |
| 985.8723 | 985.8723 | C60H115N5O3P0S1Cl0 | 1.0 |
| 986.3528 | 986.3528 | C30H58N20O10P0S4Cl0 | 1.0 |
| 986.3627 | 986.3627 | C29H57N20O13P3S0Cl0 | 1.0 |
| 986.5290 | 986.5290 | C52H90N0O7P0S5Cl0 | 1.0 |
| 995.8627 | 995.8627 | C25H20N6O23P0S7Cl0 | 1.0 |
| 1013.9048 | 1013.9048 | C19H22N18O14P0S9Cl0 | 1.0 |
| 1044.5599 | 1044.5599 | C63H80N0O13P0S0Cl0 | 1.0 |
| 1200.1017 | 1200.1017 | C74H145N5O4P0S1Cl0 (not found) | 1.0 |
| 292.2402 | 292.2402 | C19H32N0O2P0S0Cl0 | 1.0 |
| 540.5841 | 540.5841 | | 1.0 |
| 824.4081 | 824.4081 | C38H69N2O11P1S2Cl0 | 1.0 |
| 654.2799 | 654.2799 | C35H46N2O6P0S2Cl0 | 1.0 |
| 676.3725 | 676.3725 | C32H60N4O5P0S3Cl0 | 1.0 |
| 566.1430 | 566.1430 | C17H31N10O4P1S3Cl0 | 1.0 |
| 195.0533 | 195.0533 | C9H9N1O4P0S0Cl0 | 1.0 |
| 300.2065 | 300.2065 | C16H24N6O0P0S0Cl0 | 1.0 |
| 264.0886 | 264.0886 | | 1.0 |
| 150.0382 | 150.0382 | | 1.0 |
| 195.9984 | 195.9984 | | 1.0 |
| 637.4965 | 637.4965 | C35H67N5O3P0S1Cl0 | 1.0 |
| 154.4306 | 154.4306 | | 1.0 |
| 166.0157 | 166.0157 | | 1.0 |
| 260.0020 | 260.0020 | C8H9N2O4P1S1Cl0 | 1.0 |
| 425.0721 | 425.0721 | C10H19N9O4P0S3Cl0 | 1.0 |
| 817.1210 | 817.1210 | C29H56N1O3P1S10Cl0 | 1.0 |
| 384.0842 | 384.0842 | C16H29N0O0P0S4Cl1 | 1.0 |
| 397.0896 | 397.0896 | C13H24N3O5P1S2Cl0 | 1.0 |
| 244.0624 | 244.0624 | C8H20N0O2P0S3Cl0 | 1.0 |
| 395.0832 | 395.0832 | C14H25N3O2P0S4Cl0 | 1.0 |
| 398.1978 | 398.1978 | C17H34N0O8P0S1Cl0 | 1.0 |
| 418.2173 | 418.2173 | C16H30N6O7P0S0Cl0 | 1.0 |
| 913.1527 | 913.1527 | C29H31N13O20P0S1Cl0 | 1.0 |
| 232.0624 | 232.0624 | | 1.0 |
| 617.1279 | 617.1279 | C23H39N1O8P0S5Cl0 | 1.0 |
| 296.9957 | 296.9957 | C12H11N1O2P0S3Cl0 | 1.0 |
| 662.1112 | 662.1112 | C20H38N8O3P0S7Cl0 | 1.0 |
| 724.3739 | 724.3739 | C52H52N0O1P0S1Cl0 | 1.0 |
| 152.0890 | 152.0890 | | 1.0 |
| 404.0906 | 404.0906 | C13H25N0O10P1S1Cl0 | 1.0 |
| 174.0166 | 174.0166 | C6H6N0O6P0S0Cl0 | 1.0 |
| 478.9552 | 478.9552 | C6H14N3O16P1S2Cl0 | 1.0 |
| 416.0389 | 416.0389 | C20H16N0O6P0S2Cl0 | 1.0 |
| 665.4043 | 665.4043 | C31H55N9O5P0S1Cl0 | 1.0 |
| 880.6725 | 880.6725 | C10H9N7O17P2S10Cl0 | 1.0 |
| 778.1438 | 778.1438 | C36H40N0O11P1S2Cl1 | 1.0 |
| 364.9067 | 364.9067 | C9H4N1O9P1S2Cl0 (not found . . . ) | 1.0 |
| 181.0457 | 181.0457 | | 1.0 |
| 736.3065 | 736.3065 | C34H32N2O0P0S0Cl0 | 1.0 |
| 634.3683 | 634.3683 | C33H55N4O4P1S1Cl0 | 1.0 |
| 746.3628 | 746.3628 | C53H50N2O0P0S1Cl0 | 1.0 |
| 775.4557 | 775.4557 | C35H62N13O3P1S1Cl0 | 1.0 |
| 262.1266 | 262.1266 | | 1.0 |
| 832.6777 | 832.6777 | C11H9N5O15P2S10Cl0 | 1.0 |
| 192.0311 | 192.0311 | | 1.0 |
| 332.1518 | 332.1518 | C13H24N4O4P0S1Cl0 (not found . . . ) | 1.0 |
| 676.1018 | 676.1018 | C27H40N4O0P0S8Cl0 | 1.0 |
| 792.2102 | 792.2102 | C28H32N20O3P0S3Cl0 | 1.0 |
| 628.3650 | 628.3650 | C26H56N6O7P0S2Cl0 | 1.0 |
| 217.9737 | 217.9737 | C4H10N0O4P0S3Cl0 | 1.0 |
| 256.0538 | 256.0538 | C8H17N0O5P1S1Cl0 | 1.0 |
| 505.2327 | 505.2327 | C20H39N7O2P0S3Cl0 | 1.0 |
| 950.4736 | 950.4736 | C43H74N12O2P0S5Cl0 | 1.0 |
| 178.0155 | 178.0155 | | 1.1 |
| 276.1422 | 276.1422 | | 1.1 |
| 432.2027 | 432.2027 | C15H24N14O0P0S1Cl0 | 1.1 |
| 846.5127 | 846.5127 | C52H78N0O3P0S3Cl0 | 1.1 |
| 254.1282 | 254.1282 | C10H23N0O5P1S0Cl0 | 1.1 |
| 538.1014 | 538.1014 | C22H26N4O6P0S3Cl0 | 1.1 |
| 380.0715 | 380.0715 | C13H12N6O8P0S0Cl0 | 1.1 |
| 610.3022 | 610.3022 | C34H34N12O0P0S0Cl0 | 1.1 |
| 406.0418 | 406.0418 | C11H18N0O14P0S1Cl0 | 1.1 |
| 388.1207 | 388.1207 | C11H28N6O1P0S4Cl0 | 1.1 |
| 540.2696 | 540.2696 | C27H36N6O6P0S0Cl0 | 1.1 |
| 200.0362 | 200.0362 | C6H16N0O1P0S3Cl0 | 1.1 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 430.0608 | 430.0608 | C17H23N2O3P1S3Cl0 | 1.1 |
| 278.2248 | 278.2248 | C18H30N0O2P0S0Cl0 | 1.1 |
| 778.2031 | 778.2031 | C25H55N4O9P1S6Cl0 | 1.1 |
| 644.1802 | 644.1802 | C30H28N8O7P0S1Cl0 | 1.1 |
| 330.2924 | 330.2924 | C23H38N0O1P0S0Cl0 | 1.1 |
| 440.0827 | 440.0827 | C18H32N0O0P0S6Cl0 | 1.1 |
| 477.2848 | 477.2848 | C26H43N3O1P0S2Cl0 | 1.1 |
| 426.0669 | 426.0669 | C16H18N4O6P0S2Cl0 | 1.1 |
| 449.2020 | 449.2020 | C19H35N3O5P0S2Cl0 | 1.1 |
| 382.1082 | 382.1082 | C20H19N2O4P1S0Cl0 | 1.1 |
| 296.2350 | 296.2350 | C18H32N0O3P0S0Cl0 | 1.1 |
| 780.4959 | 780.4959 | C40H65N10O4P1S0Cl0 | 1.1 |
| 408.1041 | 408.1041 | C13H29N0O8P1S2Cl0 | 1.1 |
| 357.1056 | 357.1056 | C10H24N5O3P1S2Cl0 | 1.1 |
| 382.2201 | 382.2201 | C17H34N0O9P0S0Cl0 | 1.1 |
| 494.9330 | 494.9330 | C9H15N5O7P2S4Cl0 | 1.1 |
| 534.3148 | 534.3148 | C27H51N0O6P1S1Cl0 | 1.1 |
| 662.3551 | 662.3551 | C32H59N2O6P1S2Cl0 | 1.1 |
| 682.3235 | 682.3235 | C31H54N0O14P0S1Cl0 | 1.1 |
| 248.0573 | 248.0573 | | 1.1 |
| 875.1570 | 875.1570 | C21H43N5O28P2S0Cl0 | 1.1 |
| 340.2431 | 340.2431 | C20H36N0O2P0S1Cl0 | 1.1 |
| 792.5375 | 792.5375 | C40H68N14O1P0S1Cl0 | 1.1 |
| 647.1385 | 647.1385 | C24H41N1O9P0S5Cl0 | 1.1 |
| 400.3461 | 400.3461 | | 1.1 |
| 297.0006 | 297.0006 | C7H12N3O4P1S2Cl0 | 1.1 |
| 344.9739 | 344.9739 | C11H11N3O2P0S4Cl0 | 1.1 |
| 471.2409 | 471.2409 | C30H33N1O4P0S0Cl0 | 1.1 |
| 914.5104 | 914.5104 | C45H86N0O10P0S4Cl0 | 1.1 |
| 524.1776 | 524.1776 | C24H28N8O2P0S2Cl0 | 1.1 |
| 388.1501 | 388.1501 | C14H29N0O10P1S0Cl0 | 1.1 |
| 912.4496 | 912.4496 | C51H64N1O0P0S3Cl0 | 1.1 |
| 344.8981 | 344.8981 | C5H5N5O3P1S3Cl1 | 1.1 |
| 971.4241 | 971.4241 | C47H62N11O8P1S1Cl0 | 1.1 |
| 812.5064 | 812.5064 | C41H73N4O10P1S0Cl0 | 1.1 |
| 637.4959 | 637.4959 | C35H75N1O2P0S3Cl0 | 1.1 |
| 399.3224 | 399.3224 | | 1.1 |
| 217.9804 | 217.9804 | C7H7N0O4P1S1Cl0 | 1.1 |
| 360.1268 | 360.1268 | C12H24N0O12P0S0Cl0 | 1.1 |
| 674.4065 | 674.4065 | C35H62N0O10P0S1Cl0 | 1.1 |
| 964.4970 | 964.4970 | C38H78N8O16P2S0Cl0 | 1.1 |
| 152.1203 | 152.1203 | C10H16N0O1P0S0Cl0 | 1.1 |
| 695.2775 | 695.2775 | C31H57N3O2P0S6Cl0 | 1.1 |
| 250.0841 | 250.0841 | C13H14N0O5P0S0Cl0 | 1.1 |
| 972.4007 | 972.4007 | C45H72N4O11P0S4Cl0 | 1.1 |
| 471.0690 | 471.0690 | C11H30N5O3P1S5Cl0 | 1.1 |
| 538.1137 | 538.1137 | C13H24N12O6P2S1Cl0 | 1.1 |
| 404.0894 | 404.0894 | C10H17N10O4P1S1Cl0 | 1.1 |
| 620.3896 | 620.3896 | C31H52N6O7P0S0Cl0 | 1.1 |
| 456.2634 | 456.2634 | C27H40N2O0P0S2Cl0 | 1.1 |
| 310.0214 | 310.0214 | C7H18N0O7P0S3Cl0 | 1.1 |
| 534.0472 | 534.0472 | C11H23N10O5P1S4Cl0 | 1.1 |
| 130.0268 | 130.0268 | C5H6N0O4P0S0Cl0 | 1.1 |
| 602.0829 | 602.0829 | C22H20N8O9P2S0Cl0 | 1.1 |
| 480.1971 | 480.1971 | C15H25N14O3P1S0Cl0 | 1.1 |
| 479.1075 | 479.1075 | C15H33N3O4P0S5Cl0 | 1.1 |
| 395.0620 | 395.0620 | C17H21N3O0P0S4Cl0 | 1.1 |
| 430.0778 | 430.0778 | C16H19N2O10P1S0Cl0 | 1.1 |
| 746.4205 | 746.4205 | C27H58N18O1P0S3Cl0 | 1.1 |
| 492.9346 | 492.9346 | C10H15N5O6P0S6Cl0 | 1.1 |
| 830.2260 | 830.2260 | C24H39N20O6P1S3Cl0 | 1.1 |
| 818.4474 | 818.4474 | C46H66N4O5P0S2Cl0 | 1.1 |
| 600.0809 | 600.0809 | C19H32N6O4P0S6Cl0 | 1.1 |
| 366.0743 | 366.0743 | C13H22N2O4P0S3Cl0 | 1.1 |
| 810.1566 | 810.1566 | C23H31N12O19P1S0Cl0 | 1.1 |
| 188.9956 | 188.9956 | C3H11N1O2P0S3Cl0 | 1.1 |
| 785.4559 | 785.4559 | C38H55N15O4P0S0Cl0 | 1.1 |
| 675.8497 | 675.8497 | C16H12N4O12P0S7Cl0 | 1.1 |
| 819.3989 | 819.3989 | C41H63N3O10P2S0Cl0 | 1.1 |
| 880.6784 | 880.6784 | C45H84N16O0P0S1Cl0 | 1.1 |
| 396.0932 | 396.0932 | C14H25N2O5P1S2Cl0 | 1.1 |
| 818.4750 | 818.4750 | C39H75N6O4P1S3Cl0 | 1.1 |
| 586.1060 | 586.1060 | C16H22N14O5P0S3Cl0 | 1.2 |
| 694.3767 | 694.3767 | C31H62N6O3P0S4Cl0 | 1.2 |
| 538.1915 | 538.1915 | C22H34N0O15P0S0Cl0 | 1.2 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 554.0875 | 554.0875 | C14H31N6O7P1S4Cl0 | 1.2 |
| 808.1876 | 808.1876 | C23H49N6O15P1S4Cl0 | 1.2 |
| 782.4620 | 782.4620 | C38H76N2O6P2S2Cl0 | 1.2 |
| 201.0266 | 201.0266 | | 1.2 |
| 532.1821 | 532.1821 | C18H32N10O3P0S3Cl0 | 1.2 |
| 816.4999 | 816.4999 | C40H69N10O4P1S1Cl0 | 1.2 |
| 808.1995 | 808.1995 | C28H56N0O14P0S6Cl0 | 1.2 |
| 410.1026 | 410.1026 | C13H23N4O7P1S1Cl0 | 1.2 |
| 645.1845 | 645.1845 | C29H36N5O6P1S2Cl0 | 1.2 |
| 401.2040 | 401.2040 | C16H23N11O2P0S0Cl0 | 1.2 |
| 152.0270 | 152.0270 | | 1.2 |
| 384.3234 | 384.3234 | | 1.2 |
| 260.1776 | 260.1776 | C17H24N0O2P0S0Cl0 | 1.2 |
| 394.3605 | 394.3605 | C29H46N0O0P0S0Cl0 | 1.2 |
| 430.0606 | 430.0606 | C9H19N8O6P1S2Cl0 | 1.2 |
| 699.3563 | 699.3563 | C38H57N3O3P0S3Cl0 | 1.2 |
| 364.0980 | 364.0980 | C10H16N6O9P0S0Cl0 | 1.2 |
| 948.9467 | 948.9467 | C32H27N1O21P4S2Cl0 | 1.2 |
| 948.5152 | 948.5152 | C49H74N8O7P2S0Cl0 | 1.2 |
| 378.0922 | 378.0922 | C14H14N6O7P0S0Cl0 | 1.2 |
| 662.1169 | 662.1169 | C24H31N4O12P1S2Cl0 | 1.2 |
| 585.1850 | 585.1850 | C24H28N9O7P1S0Cl0 | 1.2 |
| 314.1045 | 314.1045 | C12H26N0O3P0S3Cl0 | 1.2 |
| 492.2730 | 492.2730 | C20H40N6O6P0S1Cl0 | 1.2 |
| 264.0883 | 264.0883 | | 1.2 |
| 244.1076 | 244.1076 | C11H12N6O1P0S0Cl0 | 1.2 |
| 424.0616 | 424.0616 | C22H16N0O7P0S1Cl0 | 1.2 |
| 352.0312 | 352.0312 | C8H16N0O13P0S1Cl0 | 1.2 |
| 660.1178 | 660.1178 | C25H28N10O4P0S4Cl0 | 1.2 |
| 457.2119 | 457.2119 | C19H27N11O1P0S1Cl0 | 1.2 |
| 798.4349 | 798.4349 | C35H63N10O7P1S1Cl0 | 1.2 |
| 785.4803 | 785.4803 | C40H75N5O2P0S4Cl0 | 1.2 |
| 625.2698 | 625.2698 | C28H44N5O7P1S1Cl0 | 1.2 |
| 275.9793 | 275.9793 | C8H9N2O3P1S2Cl0 | 1.2 |
| 815.4541 | 815.4541 | C40H81N1O3P0S6Cl0 | 1.2 |
| 1012.5249 | 1012.5249 | C58H84N4O1P0S5Cl0 | 1.2 |
| 318.1056 | 318.1056 | C14H23N0O4P1S1Cl0 | 1.2 |
| 380.0888 | 380.0888 | C13H20N2O9P0S1Cl0 | 1.2 |
| 710.3551 | 710.3551 | C28H55N8O9P1S1Cl0 | 1.2 |
| 917.2550 | 917.2550 | C37H47N3O24P0S0Cl0 | 1.2 |
| 486.0362 | 486.0362 | C12H24N0O14P2S1Cl0 | 1.2 |
| 532.0431 | 532.0431 | C15H16N8O10P0S2Cl0 | 1.2 |
| 812.2607 | 812.2607 | C27H44N10O17P0S1Cl0 | 1.2 |
| 724.3703 | 724.3703 | C32H48N14O4P0S1Cl0 | 1.2 |
| 508.1998 | 508.1998 | C31H28N2O5P0S0Cl0 | 1.2 |
| 228.1881 | 228.1881 | C17H24N0O0P0S0Cl0 | 1.2 |
| 928.5037 | 928.5037 | C37H70N16O8P2S0Cl0 | 1.2 |
| 318.2928 | 318.2928 | C22H38N0O1P0S0Cl0 | 1.2 |
| 294.2345 | 294.2345 | C22H30N0O0P0S0Cl0 | 1.2 |
| 714.5094 | 714.5094 | C40H74N0O8P0S1Cl0 | 1.2 |
| 480.2408 | 480.2408 | C23H36N4O5P0S1Cl0 | 1.2 |
| 612.3910 | 612.3910 | C30H60N0O10P0S1Cl0 | 1.2 |
| 950.4564 | 950.4564 | C34H75N14O7P1S4Cl0 | 1.2 |
| 816.4374 | 816.4374 | C49H69N0O4P1S2Cl0 | 1.2 |
| 610.3032 | 610.3032 | C29H54N0O7P0S3Cl0 | 1.2 |
| 348.3397 | 348.3397 | C24H44N0O1P0S0Cl0 | 1.2 |
| 878.7380 | 878.7380 | C58H94N4O2P0S0Cl0 | 1.3 |
| 486.1646 | 486.1646 | C25H30N2O4P0S2Cl0 | 1.3 |
| 1009.4699 | 1009.4699 | C47H77N7O9P2S2Cl0 | 1.3 |
| 419.1068 | 419.1068 | C11H18N9O7P1S0Cl0 | 1.3 |
| 677.3746 | 677.3746 | C42H52N3O3P1S0Cl0 | 1.3 |
| 395.0821 | 395.0821 | C13H21N3O7P0S2Cl0 | 1.3 |
| 426.0762 | 426.0762 | C16H19N4O6P1S1Cl0 | 1.3 |
| 517.0703 | 517.0703 | C14H24N5O10P1S2Cl0 | 1.3 |
| 971.3947 | 971.3947 | C30H65N15O15P0S3Cl0 | 1.3 |
| 466.1966 | 466.1966 | C31H30N0O2P0S1Cl0 | 1.3 |
| 392.0263 | 392.0263 | C10H16N0O14P0S1Cl0 | 1.3 |
| 900.3663 | 900.3663 | C44H48N14O8P0S0Cl0 | 1.3 |
| 364.1288 | 364.1288 | C15H25N0O8P1S0Cl0 | 1.3 |
| 324.1054 | 324.1054 | C12H20N0O10P0S0Cl0 | 1.3 |
| 448.0578 | 448.0578 | C12H24N4O6P0S4Cl0 | 1.3 |
| 208.0259 | 208.0259 | | 1.3 |
| 830.4298 | 830.4298 | C36H71N4O11P1S2Cl0 | 1.3 |
| 302.2220 | 302.2220 | C16H26N6O0P0S0Cl0 | 1.3 |
| 676.1027 | 676.1027 | C23H21N10O13P1S0Cl0 | 1.3 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 628.3653 | 628.3653 | C26H56N6O7P0S2Cl0 (not found . . . ) | 1.3 |
| 201.0271 | 201.0271 | C7H7N1O6P0S0Cl0 | 1.3 |
| 386.1867 | 386.1867 | C18H30N2O5P0S1Cl0 (not found . . . ) | 1.3 |
| 554.0794 | 554.0794 | C19H27N2O11P1S2Cl0 | 1.3 |
| 936.3431 | 936.3431 | C41H66N2O14P2S2Cl0 | 1.3 |
| 260.2503 | 260.2503 | C19H32N0O0P0S0Cl0 | 1.3 |
| 972.3879 | 972.3879 | C38H74N2O18P2S2Cl0 | 1.3 |
| 971.4002 | 971.4002 | C58H58N3O9P1S0Cl0 | 1.3 |
| 276.0156 | 276.0156 | C7H16N0O5P0S3Cl0 | 1.3 |
| 862.4167 | 862.4167 | C40H79N0O7P1S5Cl0 | 1.3 |
| 655.0587 | 655.0587 | C22H17N13O6P0S3Cl0 | 1.3 |
| 684.2320 | 684.2320 | C29H50N0O10P2S2Cl0 | 1.3 |
| 875.1388 | 875.1388 | C19H39N15O15P2S3Cl0 | 1.3 |
| 250.0001 | 250.0001 | C5H14N0O5P0S3Cl0 | 1.3 |
| 884.2315 | 884.2315 | C36H54N0O17P2S2Cl0 | 1.3 |
| 262.0000 | 262.0000 | C6H14N0O5P0S3Cl0 | 1.3 |
| 471.0683 | 471.0683 | C15H21N1O14P0S1Cl0 | 1.3 |
| 426.0680 | 426.0680 | C11H22N0O15P0S1Cl0 | 1.3 |
| 913.4535 | 913.4535 | C38H69N13O7P2S1Cl0 | 1.3 |
| 745.9763 | 745.9763 | C18H27N4O16P1S5Cl0 | 1.3 |
| 532.0941 | 532.0941 | C12H24N1O08P0S3Cl0 | 1.3 |
| 244.0623 | 244.0623 | C8H20N0O2P0S3Cl0 | 1.3 |
| 657.2617 | 657.2617 | C35H47N1O5P0S3Cl0 (not found . . . ) | 1.3 |
| 304.1196 | 304.1196 |  | 1.3 |
| 180.0422 | 180.0422 | C9H8N0O4P0S0Cl0 | 1.3 |
| 258.0780 | 258.0780 | C9H22N0O2P0S3Cl0 | 1.3 |
| 289.9948 | 289.9948 | C9H11N2O3P1S2Cl0 | 1.3 |
| 602.0830 | 602.0830 | C30H24N2O6P2S1Cl0 | 1.3 |
| 256.1264 | 256.1264 |  | 1.3 |
| 340.0681 | 340.0681 | C12H21N2O3P0S2Cl1 | 1.3 |
| 394.1206 | 394.1206 | C11H22N8O4P0S2Cl0 | 1.3 |
| 1218.2356 | 1218.2356 | C56H70N2O8P0S10Cl0 | 1.3 |
| 412.9427 | 412.9427 | C10H7N9O0P0S5Cl0 | 1.3 |
| 986.3826 | 986.3826 | C47H47N2O4P1S0Cl0 | 1.3 |
| 913.4576 | 913.4576 | C42H64N11O10P1S0Cl0 | 1.3 |
| 856.7442 | 856.7442 | C52H104N0O6P0S1Cl0 | 1.4 |
| 326.2455 | 326.2455 | C19H34N0O4P0S0Cl0 | 1.4 |
| 212.1413 | 212.1413 | C12H20N0O3P0S0Cl0 | 1.4 |
| 566.0426 | 566.0426 | C23H34N0O0P0S8Cl0 | 1.4 |
| 289.0683 | 289.0683 | C7H12N7O4P1S0Cl0 | 1.4 |
| 817.1142 | 817.1142 | C24H19N17O17P0S0Cl0 | 1.4 |
| 964.5123 | 964.5123 | C37H78N10O15P2S0Cl0 | 1.4 |
| 963.4866 | 963.4866 | C45H77N11O2P0S5Cl0 | 1.4 |
| 480.1877 | 480.1877 | C23H28N8O0P0S2Cl0 | 1.4 |
| 237.9378 | 237.9378 |  | 1.4 |
| 884.7887 | 884.7887 | C63H100N2O0P0S0Cl0 | 1.4 |
| 993.8393 | 993.8393 | C60H115N1O7P0S1Cl0 | 1.4 |
| 422.1463 | 422.1463 | C17H31N2O4P1S2Cl0 | 1.4 |
| 574.3857 | 574.3857 | C31H46N10O1P0S0Cl0 | 1.4 |
| 460.1769 | 460.1769 | C16H29N8O4P1S1Cl0 | 1.4 |
| 398.1976 | 398.1976 | C17H34N0O8P0S1Cl0 (not found...) | 1.4 |
| 330.2772 | 330.2772 | C19H38N0O4P0S0Cl0 | 1.4 |
| 264.1492 | 264.1492 | C12H25N0O4P1S0Cl0 | 1.4 |
| 167.1600 | 167.1600 |  | 1.4 |
| 192.0311 | 192.0311 |  | 1.4 |
| 478.9550 | 478.9550 | C9H5N9O11P0S2Cl0 | 1.4 |
| 200.0363 | 200.0363 | C6H16N0O1P0S3Cl0 | 1.4 |
| 292.2168 | 292.2168 | C15H33N0O3P1S0Cl0 | 1.4 |
| 828.2339 | 828.2339 | C27H42N16O7P2S2Cl0 | 1.4 |
| 278.1041 | 278.1041 |  | 1.4 |
| 658.4349 | 658.4349 | C34H66N4O2P0S3Cl0 | 1.4 |
| 342.1157 | 342.1157 | C10H18N10O0P0S2Cl0 | 1.4 |
| 774.5285 | 774.5285 | C40H71N8O5P1S0Cl0 (not found . . . ) | 1.4 |
| 278.2249 | 278.2249 | C18H30N0O2P0S0Cl0 | 1.4 |
| 885.7975 | 885.7975 | C21H18N4O15P0S10Cl0 | 1.4 |
| 538.1939 | 538.1939 | C18H30N14O0P0S3Cl0 | 1.4 |
| 318.1353 | 318.1353 |  | 1.4 |
| 574.4960 | 574.4960 | C37H66N0O4P0S0Cl0 | 1.4 |
| 396.3756 | 396.3756 | C29H48N0O0P0S0Cl0 | 1.4 |
| 280.0986 | 280.0986 | C12H24N0O1P0S3Cl0 (not found . . . ) | 1.4 |
| 860.4851 | 860.4851 | C59H64N4O0P0S1Cl0 | 1.4 |
| 408.3756 | 408.3756 | C30H48N0O0P0S0Cl0 | 1.4 |
| 216.0313 | 216.0313 | C6H16N0O2P0S3Cl0 | 1.4 |
| 927.5292 | 927.5292 | C50H79N3O9P2S0Cl0 | 1.4 |
| 972.4930 | 972.4930 | C43H76N10O9P0S3Cl0 | 1.4 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 751.1191 | 751.1191 | C25H37N9O6P0S6Cl0 | 1.4 |
| 282.0260 | 282.0260 | C8H15N2O3P1S2Cl0 | 1.4 |
| 576.1481 | 576.1481 | C22H33N4O8P1S2Cl0 | 1.4 |
| 962.4705 | 962.4705 | C46H83N4O5P1S5Cl0 | 1.5 |
| 844.4908 | 844.4908 | C41H76N6O4P0S4Cl0 | 1.5 |
| 574.3838 | 574.3838 | C30H58N2O4P0S2Cl0 | 1.5 |
| 296.0418 | 296.0418 | C9H17N2O3P1S2Cl0 | 1.5 |
| 598.4965 | 598.4965 | C32H66N6O2P0S1Cl0 | 1.5 |
| 816.4582 | 816.4582 | C49H64N6O1P0S2Cl0 | 1.5 |
| 362.0883 | 362.0883 | C11H22N0O11P0S1Cl0 | 1.5 |
| 810.4394 | 810.4394 | C46H66N0O10P0S1Cl0 | 1.5 |
| 260.0572 | 260.0572 | C8H20N0O3P0S3Cl0 (not found . . . ) | 1.5 |
| 166.0156 | 166.0156 |  | 1.5 |
| 382.3600 | 382.3600 | C28H46N0O0P0S0Cl0 | 1.5 |
| 950.4378 | 950.4378 | C44H58N18O3P0S2Cl0 | 1.5 |
| 181.0458 | 181.0458 |  | 1.5 |
| 867.6712 | 867.6712 | C8H6N8O19P2S9Cl0 | 1.5 |
| 978.5065 | 978.5065 | C42H78N10O10P0S3Cl0 | 1.5 |
| 336.2662 | 336.2662 | C21H36N0O3P0S0Cl0 | 1.5 |
| 614.3726 | 614.3726 | C32H59N2O3P1S2Cl0 | 1.5 |
| 312.4166 | 312.4166 |  | 1.5 |
| 134.0217 | 134.0217 | C4H6N0O5P0S0Cl0 | 1.5 |
| 133.9894 | 133.9894 |  | 1.5 |
| 152.0897 | 152.0897 |  | 1.5 |
| 163.9999 | 163.9999 |  | 1.5 |
| 750.1219 | 750.1219 | C19H35N12O10P1S4Cl0 | 1.5 |
| 963.8180 | 963.8180 | C24H24N2O19P0S10Cl0 | 1.5 |
| 312.1244 | 312.1244 | C12H24N0O7P0S1Cl0 | 1.5 |
| 326.0525 | 326.0525 | C10H19N2O4P1S2Cl0 | 1.5 |
| 232.0624 | 232.0624 |  | 1.5 |
| 178.0156 | 178.0156 |  | 1.5 |
| 486.2500 | 486.2500 | C21H42N0O10P0S1Cl0 | 1.5 |
| 394.1303 | 394.1303 | C11H23N8O4P1S1Cl0 | 1.5 |
| 966.5005 | 966.5005 | C55H75N4O7P1S1Cl0 | 1.5 |
| 244.1076 | 244.1076 | C11H12N6O1P0S0Cl0 | 1.5 |
| 214.0518 | 214.0518 | C7H18N0O1P0S3Cl0 | 1.5 |
| 264.0156 | 264.0156 | C6H16N0O5P0S3Cl0 | 1.5 |
| 356.1600 | 356.1600 | C14H29N0O8P1S0Cl0 | 1.5 |
| 272.0571 | 272.0571 | C9H20N0O3P0S3Cl0 | 1.5 |
| 884.2337 | 884.2337 | C33H61N2O11P1S6Cl0 | 1.5 |
| 192.0634 | 192.0634 | C7H12N0O6P0S0Cl0 | 1.6 |
| 955.8587 | 955.8587 | C24H20N4O23P0S7Cl0 | 1.6 |
| 310.0209 | 310.0209 | C9H15N2O4P1S2Cl0 | 1.6 |
| 246.0415 | 246.0415 | C7H18N0O3P0S3Cl0 (not found . . . ) | 1.6 |
| 308.0420 | 308.0420 | C8H20N0O6P0S3Cl0 | 1.6 |
| 936.8086 | 936.8086 | C68H104N0O1P0S0Cl0 | 1.6 |
| 682.3244 | 682.3244 | C34H47N6O7P1S0Cl0 | 1.6 |
| 151.9999 | 151.9999 |  | 1.6 |
| 234.0415 | 234.0415 |  | 1.6 |
| 310.1454 | 310.1454 | C13H26N0O6P0S1Cl0 | 1.6 |
| 292.1197 | 292.1197 |  | 1.6 |
| 180.0311 | 180.0311 |  | 1.6 |
| 746.3918 | 746.3918 | C43H46N12O1P0S0Cl0 | 1.6 |
| 875.4004 | 875.4004 | C44H69N5O3P0S5Cl0 | 1.6 |
| 366.0743 | 366.0743 | C13H22N2O4P0S3Cl0 | 1.6 |
| 152.1202 | 152.1202 | C10H16N0O1P0S0Cl0 | 1.6 |
| 248.0571 | 248.0571 |  | 1.6 |
| 422.1464 | 422.1464 | C20H14N12O0P0S0Cl0 | 1.6 |
| 626.2460 | 626.2460 | C26H47N2O9P1S2Cl0 | 1.6 |
| 232.1827 | 232.1827 | C16H24N0O1P0S0Cl0 | 1.6 |
| 474.9923 | 474.9923 | C13H17N1O12P0S3Cl0 | 1.6 |
| 194.0103 | 194.0103 |  | 1.6 |
| 870.5649 | 870.5649 | C39H74N12O10P0S0Cl0 | 1.6 |
| 260.0936 | 260.0936 |  | 1.6 |
| 572.0899 | 572.0899 | C15H28N10O4P0S5Cl0 | 1.6 |
| 882.7673 | 882.7673 | C54H94N10O0P0S0Cl0 | 1.6 |
| 179.9947 | 179.9947 |  | 1.6 |
| 288.1245 | 288.1245 |  | 1.6 |
| 444.0785 | 444.0785 | C11H24N0O16P0S1Cl0 | 1.6 |
| 411.0563 | 411.0563 | C9H25N5O3P0S5Cl0 | 1.6 |
| 201.0848 | 201.0848 |  | 1.6 |
| 246.0779 | 246.0779 |  | 1.6 |
| 576.5115 | 576.5115 | C37H68N0O4P0S0Cl0 | 1.7 |
| 910.4780 | 910.4780 | C42H66N14O5P0S2Cl0 | 1.7 |
| 298.1088 | 298.1088 | C11H22N0O7P0S1Cl0 | 1.7 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 796.4455 | 796.4455 | C44H74N0O4P1S2Cl1 | 1.7 |
| 293.9899 | 293.9899 | C8H11N2O4P1S2Cl0 | 1.7 |
| 302.1401 | 302.1401 | C13H23N2O4P1S0Cl0 | 1.7 |
| 876.7218 | 876.7218 | C50H104N2O3P0S3Cl0 | 1.7 |
| 854.7375 | 854.7375 | C55H98N0O6P0S0Cl0 | 1.7 |
| 266.0917 | 266.0917 | C13H10N6O1P0S0Cl0 | 1.7 |
| 452.9327 | 452.9327 | C6H19N3O6P0S7Cl0 | 1.7 |
| 148.0051 | 148.0051 | | 1.7 |
| 150.0381 | 150.0381 | | 1.7 |
| 213.0824 | 213.0824 | C10H15N1O2P0S1Cl0 | 1.8 |
| 342.0625 | 342.0625 | C12H22N0O5P0S3Cl0 | 1.8 |
| 332.1507 | 332.1507 | C14H25N2O5P1S0Cl0 | 1.8 |
| 290.1040 | 290.1040 | | 1.8 |
| 346.8964 | 346.8964 | C10H6N1O3P1S4Cl0 | 1.8 |
| 206.0469 | 206.0469 | | 1.8 |
| 373.0998 | 373.0998 | C20H15N5O1P0S1Cl0 | 1.8 |
| 580.3651 | 580.3651 | C30H60N0O4P0S3Cl0 | 1.8 |
| 178.0328 | 178.0328 | | 1.8 |
| 763.1941 | 763.1941 | C30H43N3O14P2S1Cl0 | 1.9 |
| 596.1004 | 596.1004 | C19H25N4O16P1S0Cl0 | 1.9 |
| 583.4490 | 583.4490 | C31H61N5O3P0S1Cl0 | 1.9 |
| 981.4864 | 981.4864 | C61H67N5O5P0S1Cl0 | 1.9 |
| 232.0981 | 232.0981 | C9H17N2O3P1S0Cl0 | 1.9 |
| 276.0886 | 276.0886 | | 1.9 |
| 542.1670 | 542.1670 | C27H26N8O1P0S2Cl0 | 1.9 |
| 594.3811 | 594.3811 | C31H62N0O4P0S3Cl0 | 1.9 |
| 560.1263 | 560.1263 | C19H33N2O11P1S2Cl0 | 1.9 |
| 346.1108 | 346.1108 | C11H22N0O12P0S0Cl0 | 1.9 |
| 364.9068 | 364.9068 | C9H4N1O9P1S2Cl0 | 1.9 |
| 674.2713 | 674.2713 | C35H34N10O5P0S0Cl0 (not found . . . ) | 1.9 |
| Mean_Mass | Mean_Mass | Formulae | Fold change by GDH |
| 280.0630 | 280.0630 | C11H12N4O3P0S1Cl0 | 2.0 |
| 206.0104 | 206.0104 | C7H3N6O0P0S0Cl0 | 2.0 |
| 324.0360 | 324.0360 | C9H13N2O9P1S0Cl0 | 2.0 |
| 479.2148 | 479.2148 | C18H34N5O8P1S0Cl0 (not found . . . ) | 2.0 |
| 310.1460 | 310.1460 | C14H30N0O1P0S3Cl0 (not found . . . ) | 2.0 |
| 457.0529 | 457.0529 | C9H16N9O9P1S1Cl0 (not found . . . ) | 2.0 |
| 326.1401 | 326.1401 | C13H26N0O7P0S1Cl0 (not found . . . ) | 2.0 |
| 284.1749 | 284.1749 | C15H20N6O0P0S0Cl0 | 2.0 |
| 328.2611 | 328.2611 | C19H36N0O4P0S0Cl0 (Propylene Glycol Dicaprylate) | 2.0 |
| 292.2166 | 292.2166 | C15H33N0O3P1S0Cl0 (Tri-neo-pentylphosphite;Diamyl amyl phosphonate) | 2.0 |
| 278.2245 | 278.2245 | C18H30N0O2P0S0Cl0 | 2.1 |
| 316.0464 | 316.0464 | C9H16N0O10P0S1Cl0 (not found . . . ) | 2.1 |
| 346.1302 | 346.1302 | C12H26N0O9P0S1Cl0 (not found . . . ) | 2.1 |
| 277.9627 | 277.9627 | | 2.1 |
| 234.1232 | 234.1232 | C10H14N6O1P0S0Cl0 (4-(5-amino-1,2,4-triazol-3-yl)-N-(2-methoxyethyl)-2-pyridineamine) | 2.1 |
| 918.2544 | 918.2544 | C33H62N10O2P0S9Cl0 (not found) | 2.2 |
| 362.9091 | 362.9091 | C3H10N3O7P0S4Cl1 (not found . . . ) | 2.2 |
| 245.9817 | 245.9817 | | 2.2 |
| 288.0154 | 288.0154 | C7H12N0O10P0S1Cl0 (not found . . . ) | 2.2 |
| 306.0989 | 306.0989 | | 2.2 |
| 280.2401 | 280.2401 | C18H32N0O2P0S0Cl0 (9,12-Octadecadienoic acid;Geranyl caprylate;Hexadecadien-1-ol,acetate,(Z,E)-;Hexadecadien-1-ol, acetate, (Z,Z)-;cis-7,trans-11-hexadecadienyl acetate;11-Hexadecynyl acetate;Linoleic acid) | 2.2 |
| 112.1016 | 112.1016 | | 2.2 |
| 596.1019 | 596.1019 | C13H29N10O9P1S3Cl0 (not found . . . ) | 2.3 |
| 229.9828 | 229.9828 | C4H7N0O9P1S0Cl0 | 2.3 |
| 262.0731 | 262.0731 | C8H14N4O4P0S1Cl0 (not found) | 2.3 |
| 166.0060 | 166.0060 | | 2.3 |
| 264.1209 | 264.1209 | C11H20N0O7P0S0Cl0 | 2.3 |
| 244.1002 | 244.1002 | C17H12N2O0P0S0Cl0 | 2.3 |
| 272.1600 | 272.1600 | C18H24N0O0P0S1Cl0 (not found) | 2.3 |
| 688.2090 | 688.2090 | C20H46N6O12P2S2Cl0 (not found) | 2.4 |
| 208.0080 | 208.0080 | | 2.5 |
| 362.9083 | 362.9083 | C5H15N1O3P1S5Cl1 (not found . . . ) | 2.6 |
| 248.0936 | 248.0936 | | 2.6 |
| 288.0885 | 288.0885 | C10H24N0O3P0S3Cl0 | 2.7 |
| 228.0312 | 228.0312 | C7H16N0O2P0S3Cl0 (not found) | 2.7 |

TABLE 7-continued

Metabolites altered in abundance in roots of *Zea mays* showing resistance to *Fusarium virguliforme*.

| Mean_Mass | Mean_Mass | CHNOPSCl | SIU06 vs SIU08 |
|---|---|---|---|
| 779.1409 | 779.1409 | C30H25N19O0P0S4Cl0 (not found) | 2.7 |
| 236.0572 | 236.0572 | | 2.7 |
| 310.0093 | 310.0093 | C9H11N0O10P1S0Cl0 | 2.7 |
| 306.1354 | 306.1354 | | 2.9 |
| 250.0728 | 250.0728 | | 3.0 |
| 274.0727 | 274.0727 | C8H18N0O8P0S1Cl0 (not found) | 3.0 |
| 270.1232 | 270.1232 | C10H23N0O6P1S0Cl0 (not found . . . ) | 3.0 |
| 262.0363 | 262.0363 | C7H18N0O4P0S3Cl0 (not found . . . ) | 3.0 |
| 318.1356 | 318.1356 | C12H22N4O4P0S1Cl0 | 3.1 |
| 362.1037 | 362.1037 | C10H19N8O3P1S1Cl0 (not found) | 3.1 |
| 1218.1476 | 1218.1476 | C44H38N10O30P0S1Cl0 (not found) | 3.3 |
| 260.1025 | 260.1025 | C11H12N6O2P0S0Cl0 | 3.4 |
| 246.0707 | 246.0707 | C6H10N6O5P0S0Cl0 | 4.7 |
| 274.1094 | 274.1094 | | 5.2 |
| 218.0468 | 218.0468 | | 5.6 |

What is claimed is:

1. A method for reducing aflatoxin accumulation in a crop plant, the method comprising:
   a. selecting a crop plant line susceptible to infection with *Aspergillus flavus*; and
   b. transforming a plant from the selected plant line with a DNA sequence encoding a bacterial NADP-specific glutamate dehydrogenase enzyme so that the plant expresses the bacterial NADP-specific glutamate dehydrogenase enzyme in an amount sufficient to reduce aflatoxin accumulation in comparison to an amount of aflatoxin accumulation in an untransformed plant from the *A. flavus* susceptible plant line.

2. The method of claim 1 wherein the plant line is a food crop plant line.

3. The method of claim 2 wherein the plant line is a cereal plant line.

4. The method of claim 2 wherein the plant line is selected from the group consisting of maize, sorghum, pearl millet, rice, wheat.

5. The method of claim 2 wherein the plant line is an oilseeds plant line.

6. The method of claim 2 wherein the plant line is selected from the group consisting of peanut, soybean, sunflower, and cotton.

7. The method of claim 1 further comprising growing the plant in conditions associated with *A. flavus* infection of the plant.

8. The method of claim 1 wherein the DNA sequence comprises the Kozac consensus sequences.

9. A method of using a transgenic gdhA+ plant line, the method comprising:
   a. controlling aflatoxin contamination of a food crop, wherein the transgenic gdhA+ plant line is a food crop plant line susceptible to *A. flavus* infection, by growing a plant of the transgenic gdhA+ plant line in conditions associated with *A. flavus* infection;
   b. measuring the amount of aflatoxin accumulation in the plant; and
   c. comparing the amount of aflatoxin accumulation in the plant to the amount of aflatoxin accumulation in a gdhA− plant from the food crop plant line of (a).

10. The method of claim 9, wherein the plant line is a cereal plant line.

11. The method of claim 9, wherein the plant line is selected from the group consisting of maize, sorghum, pearl millet, rice, wheat.

12. The method of claim 9, wherein the plant line is an oilseeds plant line.

13. The method of claim 9, wherein the plant line is selected from the group consisting of peanut, soybean, sunflower, and cotton.

14. The method of claim 9, wherein the DNA sequence comprises the Kozac consensus sequences.

15. A method of controlling aflatoxin contamination of a crop comprising:
   a. selecting an *A. flavus* susceptible crop plant line;
   b. transforming a plant from the selected plant line with a DNA sequence encoding a bacterial NADP-specific glutamate dehydrogenase enzyme to produce a transgenic gdhA+ plant line; and
   c. growing a plant of the transgenic gdhA+ plant line in conditions associated with *A. flavus* infection.

16. The method of claim 15, wherein the plant line is a food crop plant line.

17. The method of claim 16, wherein the plant line is a cereal plant line.

18. The method of claim 16, wherein the plant line is selected from the group consisting of maize, sorghum, pearl millet, rice, wheat.

19. The method of claim 16, wherein the plant line is an oilseeds plant line.

20. The method of claim 16, wherein the plant line is selected from the group consisting of peanut, soybean, sunflower, and cotton.

21. The method of claim 15, wherein the DNA sequence comprises the Kozac consensus sequences.

22. A method of controlling root rot in plants infected with *Fusarium virguliforme*, the method comprising:
   a. selecting a *F. virguliforme* susceptible plant line; and
   b. transforming a plant from the selected plant line with a DNA sequence encoding a bacterial NADP-specific glutamate dehydrogenase enzyme so that the plant expresses the bacterial NADP-specific glutamate dehydrogenase enzyme in an amount sufficient to reduce root rot in comparison to root rot in an untransformed plant from the *F. virguliforme* susceptible plant line.

23. The method of claim 22, wherein the plant line is a food crop plant line.

24. The method of claim 23, wherein the plant line is a cereal plant line.

25. The method of claim 23, wherein the plant line is selected from the group consisting of maize, sorghum, pearl millet, rice, wheat.

26. The method of claim 23, wherein the plant line is an oilseeds plant line.

27. The method of claim 23, wherein the plant line is selected from the group consisting of peanut, soybean, sunflower, and cotton.

28. The method of claim 22, wherein the plant line is a tobacco plant line.

29. The method of claim 22, further comprising growing the plant in conditions associated with *F. virguliforme* infection of the plant.

30. The method of claim 22, wherein the DNA sequence comprises the Kozac consensus sequences.

31. A method of using a transgenic gdhA+ plant line, the method comprising:
   a. controlling root rot in a crop plant, wherein the transgenic gdhA+ plant line is derived from a crop plant line susceptible to *Fusarium virguliforme* infection, by growing a plant of the transgenic gdhA+ plant line in conditions associated with *F. virguliforme* infection;
   b. measuring the amount of root rot in the plant; and
   c. comparing the amount of root rot in the plant to the amount of root rot in a gdhA− plant from the *F. virguliforme* susceptible crop plant line of (a).

32. The method of claim 31, wherein the plant line is a cereal plant line.

33. The method of claim 32, wherein the plant line is selected from the group consisting of maize, sorghum, pearl millet, rice, wheat.

34. The method of claim 31, wherein the plant line is an oilseeds plant line.

35. The method of claim 34, wherein the plant line is selected from the group consisting of peanut, soybean, sunflower, and cotton.

36. The method of claim 31, wherein the plant line is a tobacco plant line.

37. The method of claim 31, wherein the DNA sequence comprises the Kozac consensus sequences.

38. A method of controlling root rot in a crop comprising:
   a. selecting a *Fusarium virguliforme* susceptible crop plant line;

b. transforming a plant from the selected plant line with a DNA sequence encoding a bacterial NADP-specific glutamate dehydrogenase enzyme to produce a transgenic gdhA+ plant line; and c. growing a plant of the transgenic gdhA+ plant line in conditions associated with *F. virguliforme* infection.

39. The method of claim 38, wherein the plant line is a food crop plant line.

40. The method of claim 39, wherein the plant line is a cereal plant line.

41. The method of claim 40, wherein the plant line is selected from the group consisting of maize, sorghum, pearl millet, rice, wheat.

42. The method of claim 39, wherein the plant line is an oilseeds plant line.

43. The method of claim 42, wherein the plant line is selected from the group consisting of peanut, soybean, sunflower, and cotton.

44. The method of claim 38, wherein the plant line is a tobacco plant line.

45. The method of claim 38, wherein the DNA sequence comprises the Kozac consensus sequences.

46. A method of screening a crop for plants transformed with a gdhA gene, the method comprising:

a. exposing a plurality of putatively transformed plants to *Aspergillus flavus* or to *Fusarium. virguliforme;* b. selecting the plants that show resistance to the effects of the *A. flavus* or *F. virguliforme.*

47. The method of claim 46, wherein the plant line is a cereal plant line.

48. The method of claim 47, wherein the plant line is selected from the group consisting of maize, sorghum, pearl millet, rice, wheat.

49. The method of claim 46, wherein the plant line is an oilseeds plant line.

50. The method of claim 49, wherein the plant line is selected from the group consisting of peanut, soybean, sunflower, and cotton.

51. The method of claim 46, wherein the plant line is a tobacco plant line.

52. The method of claim 46, wherein the DNA sequence comprises the Kozac consensus sequences.

53. The method of claim 46, wherein the plurality of plants are exposed to *A. flavus* and wherein selecting the plants that show resistance to the effects of the *A. flavus* comprises selecting plants that show a decreased level of aflatoxin accumulation relative to a reference plant untransformed with the gdhA gene.

54. The method of claim 46, wherein the plurality of plants are exposed to *A. flavus*, and wherein selecting the plants that show resistance to the effects of the *A. flavus* comprises selecting plants that show a decreased level of ear rot relative to a reference plant untransformed with the gdhA gene.

55. The method of claim 46, wherein the plurality of plants are exposed to *F. virguliforme*, and wherein selecting the plants that show resistance to the effects of the *F. virguliforme* comprises selecting plants that show a decreased level of root rot relative to a reference plant untransformed with the gdhA gene.

* * * * *